United States Patent [19]

Takase et al.

[11] Patent Number: 5,677,465

[45] Date of Patent: Oct. 14, 1997

[54] BENZALDEHYDE OXIME DERIVATIVES, PRODUCTION AND USE THEREOF

[75] Inventors: Akira Takase, Otsu; Hiroyuki Kai, Yamatokoriyama; Kuniyoshi Nishida, Koka-gun; Koichi Morita, Koka-gun; Michio Masuko, Koka-gun; Kinya Ide; Yoshito Ueyama, both of Kusatsu, all of Japan

[73] Assignee: Shionogi & Co., Ltd., Osaka-fu, Japan

[21] Appl. No.: 472,282

[22] Filed: Jun. 7, 1995

Related U.S. Application Data

[62] Division of Ser. No. 271,941, Jul. 8, 1994, Pat. No. 5,466,661.

[30] Foreign Application Priority Data

Jul. 9, 1993 [JP] Japan ..................... 7-170235

[51] Int. Cl.$^6$ .................................. C07D 233/88
[52] U.S. Cl. ..................... 548/336.1; 548/267.4
[58] Field of Search ................. 548/336.1, 267.4

[56] References Cited

U.S. PATENT DOCUMENTS

| | | | |
|---|---|---|---|
| 4,599,348 | 7/1986 | Schmetzer et al. | 514/383 |
| 5,366,988 | 11/1994 | Toriyabe et al. | 514/383 |

FOREIGN PATENT DOCUMENTS

| | | |
|---|---|---|
| 0142653 | 5/1985 | European Pat. Off. . |
| 0513397 | 11/1992 | European Pat. Off. . |
| 1-308260 | 12/1989 | Japan . |
| 3-68559 | 3/1991 | Japan . |
| 5-1046 | 1/1993 | Japan . |
| 5-331012 | 12/1993 | Japan . |
| 5-331011 | 12/1993 | Japan . |
| 2250511 | 6/1992 | United Kingdom . |

OTHER PUBLICATIONS

Munro et al. CA 104:202322, 1986.

*Chemical Abstracts*, vol. 116, No. 1, 6 Jan. 1992, Columbus, Ohio, U.S.; Abstract No. 2318x, Hokari Hiroshi et al., "Preparation Of Hydroximoylimidazoles Or–Triazoles As Insecticides".

*Chemical Abstracts*, vol. 112, No. 23, 4 Jun. 1990, Columbus, Ohio, U.S.; Abstract No. 216938r, Hokari Hiroshi et al., "Preparation Of N–Benzoylazole O–Alkyloxime Derivatives As Insecticides".

*Primary Examiner*—Jane Fan
*Attorney, Agent, or Firm*—Wenderoth, Lind & Ponack

[57] ABSTRACT

The present invention relates to novel benzaldehyde derivatives, specifically α-azolyl-2-substituted benzaldehyde oxime derivatives, their production, and fungicidal, herbicidal and growth regulating compositions containing them.

24 Claims, No Drawings

BENZALDEHYDE OXIME DERIVATIVES, PRODUCTION AND USE THEREOF

This is a divisional application of Ser. No. 08/271,941 filed Jul. 8, 1994, now U.S. Pat. No. 5,466,661.

FIELD OF THE INVENTION

The present invention relates to novel benzaldehyde oxime derivatives, specifically α-azolyl-2-substituted benzaldehyde oxime derivatives, their production, and fungicidal, herbicidal and growth regulating compositions containing them.

BACKGROUND OF THE INVENTION

U.S. Pat. No. 4,599,348 (JP-A 60-87269), JP-A 1-308260, JP-A 3-68559, JP-A 5-1046 and WO92/09581 disclose α-azolylbenzaldehyde oxime derivatives and their insecticidal and fungicidal activities. There is still a need for compounds having superior activity, utility, etc., as well as low toxicity.

OBJECTS OF THE INVENTION

The main object of the present invention is to provide novel compounds having excellent fungicidal, herbicidal and growth regulating activities.

Another object of the present invention is to provide processes for producing the above novel compounds.

Another object of the present invention is to provide novel fungicidal, herbicidal and growth regulating compositions.

These objects as well as other objects and advantages of the present invention will become apparent to those skilled in the art from the following description.

SUMMARY OF THE INVENTION

The present inventors have intensively studied to achieve the above objects. As a result, it has been found that novel benzaldehyde oxime derivatives having various groups attached to their 2-position via an oxygen atom or sulfur atom, specifically α-azolyl-2-substituted benzaldehyde oxime derivatives, have excellent herbicidal activity, growth regulating activity, particularly growth inhibiting activity, as well as excellent fungicidal activity.

That is, the present invention provides a compound of the formula (I):

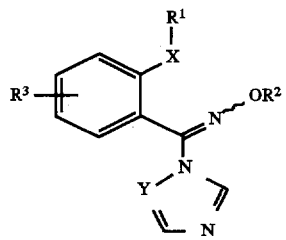

wherein $R^1$ is alkoxycarbonylalkyl, optionally substituted acylalkyl, optionally substituted phenyl, optionally substituted phenylalkyl, optionally substituted phenoxyalkyl, an optionally substituted heterocyclic group or optionally substituted heterocyclic alkyl; $R^2$ is hydrogen, alkyl, alkenyl, alkynyl, halogenated alkyl, halogenated alkenyl, halogenated alkynyl, cycloalkyl, optionally substituted phenyl, optionally substituted benzyl, an optionally substituted heterocyclic group or optionally substituted heterocyclic alkyl; $R^3$ is hydrogen, alkyl, alkoxy or halogen; X is O or S; Y is CH or N; and ~ represents any configuration of the E-isomer, Z-isomer or a mixture of E- and Z-isomers; provided that, when X is O, $R^1$ is not optionally substituted phenyl, and that when X is O, $R^1$ is not unsubstituted benzyl; or a salt thereof.

The present invention also provides a fungicidal composition comprising as an active ingredient a compound of the formula (I) and an inert carrier or diluent.

The present invention also provides a herbicidal composition comprising as an active ingredient a compound of the formula (I) and an inert carrier or diluent.

The present invention also provides a growth regulating composition comprising as an active ingredient a compound of the formula (I) and an inert carrier or diluent.

The present invention also provides a process for producing a compound of the formula (I):

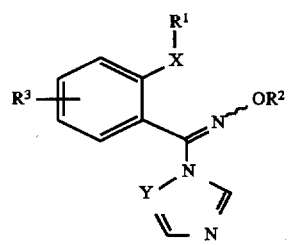

wherein each symbol is as defined above, which comprises reacting a compound of the formula (XIII):

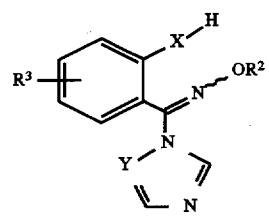

wherein each symbol is as defined for the formula (I), with a compound of the formula (III):

$$R^1\text{—}L \qquad (III)$$

wherein L is halogen, alkylsulfonyl, alkylsulfonyloxy or arylsulfonyloxy and $R^1$ is as defined for the formula (I), in the presence of a base.

The present invention also provides a process for producing a compound of the formula (I):

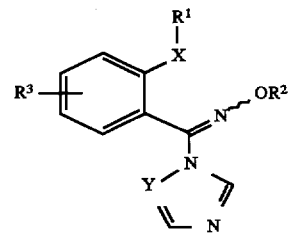

wherein each symbol is as defined above, which comprises reacting a compound of the formula (XI):

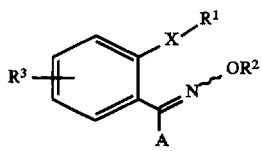 (XI)

wherein A is halogen and the other symbol is as defined for the formula (I), with a compound of the formula (XII):

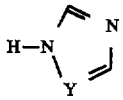 (XII)

wherein Y is as defined for the formula (I), and then, if necessary, reacting the resulting compound with a compound of the formula (XXII):

$R^2$—L (XXII)

wherein L is halogen, alkylsulfonyl, alkylsulfonyloxy or arylsulfonyloxy and $R^2$ is as defined for the formula (I) except that $R^2$ is not hydrogen, in the presence of a base.

The present invention also provides a process for producing a compound of the formula (I):

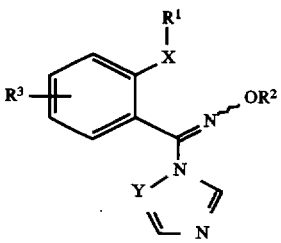 I wherein each symbol is as defined above, which comprises reacting a compound of the formula (X):

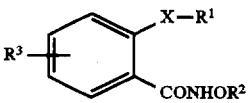 X wherein each symbol is as defined for the formula (I), with a compound of the formula (XIV):

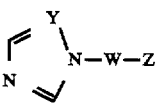 XIV wherein W is carbonyl or sulfinyl, Z is chlorine bromine or

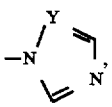, and Y is as defined for the formula (I).

The present invention also provides a process for producing a compound of the formula (I):

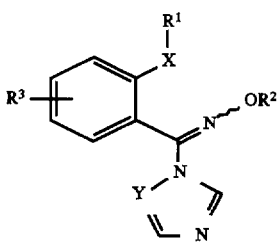 I wherein each symbol is as defined above, which comprises reacting a compound of the formula (XIII):

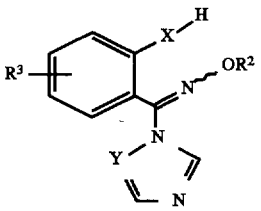 XIII wherein each symbol is as defined for the formula (I), with a compound of the formula (XXIII):

$R^1$—OH (XXIII)

wherein $R^1$ is as defined for the formula (I).

DETAILED DESCRIPTION OF THE INVENTION

Examples of the alkoxycarbonylalkyl represented by $R^1$ include alkoxycarbonylalkyl composed of alkoxycarbonyl having 2 to 6 carbon atoms and alkyl having 1 to 3 carbon atoms, such as methoxycarbonylmethyl, methoxycarbonylethyl, ethoxycarbonylmethyl, ethoxycarbonylethyl, etc. In particular, methoxycarbonylmethyl is preferred.

Examples of the optionally substituted acylalkyl represented by $R^1$ include acylalkyl composed of acyl having 1 to 8 carbon atoms (e.g., formyl, acetyl, propionyl, benzoyl, nicotinoyl, etc.) and alkyl having 1 to 3 carbon atoms, such as acetylmethyl, acetylethyl, benzoylmethyl, benzoylethyl, etc. When the acylalkyl is substituted, the substituent is selected from the same substituents as those of the optionally substituted phenyl represented by $R^1$ described below. The optionally substituted acylalkyl is preferably benzoylmethyl.

The optionally substituted phenyl represented by $R^1$ includes unsubstituted phenyl and substituted phenyl. The substituted phenyl has 1 to 5 substituents selected from $C_{1-5}$ alkyl (e.g., methyl, ethyl, isopropyl, tert-butyl, etc.), $C_{1-4}$ alkoxy (e.g., methoxy, ethoxy, propoxy, etc.), phenyl, phenoxy, benzyloxy, $C_{1-4}$ alkylthio (e.g., methylthio, ethylthio, propylthio, etc.), $C_{1-3}$ alkylsulfonyl (e.g., methylsulfonyl, ethylsulfonyl, propylsulfonyl, etc.), cyano, nitro, halogen (e.g., fluorine, chlorine, bromine, iodine), halogenated $C_{1-3}$ alkyl (e.g., trifluoromethyl, trichloromethyl, etc.) and halogenated $C_{1-3}$ alkoxy (e.g., trifluoromethyloxy, trichloromethyloxy, etc.). These substituents may be at any possible position in the phenyl. When X is O, $R^1$ is not optionally substituted phenyl.

Examples of the optionally substituted phenylalkyl represented by $R^1$ include that composed of the above optionally substituted phenyl and alkyl having 1 to 6 carbon atoms, such as phenylmethyl, phenylethyl, phenylpropyl, phenylbutyl, etc., each of which may optionally be substituted. Preferred examples of the optionally substituted phenylalkyl include optionally substituted 1-phenylalkyl (e.g., benzyl, 1-phenylethyl, 1-phenylpropyl, etc.), optionally substituted phenethyl, optionally substituted 3-phenylpropyl, etc. When X is O, the optionally substituted phenylalkyl is not unsubstituted benzyl.

Examples of the optionally substituted phenoxyalkyl represented by $R^1$ include that composed of optionally substituted phenoxy and alkyl having 1 to 6 carbon atoms, such as phenoxymethyl, phenoxyethyl, phenoxypropyl, phenoxybutyl, etc., each of which may optionally be substituted. Preferred examples of the optionally substituted phenoxyalkyl include 2-phenoxyethyl, 3-phenoxypropyl and 4-phenoxybutyl each of which may optionally be substituted.

The above optionally substituted phenyl or optionally substituted phenoxy may be attached to any possible position of the alkyl. When the phenylalkyl or phenoxyalkyl is substituted, the substituent is selected from the same substituents as those of the optionally substituted phenyl represented by $R^1$, and the substituent may be at any possible position in the phenyl ring. Preferably, the substituent is selected from $C_{1-5}$ alkyl (e.g., methyl, ethyl, isopropyl, tert-butyl, etc.), $C_{1-4}$ alkoxy (e.g., methoxy, ethoxy, propoxy, etc.), halogen (e.g., fluorine, chlorine, bromine, iodine), halogenated $C_{1-3}$ alkyl (e.g., trifluoromethyl, trichloromethyl, etc.) and halogenated $C_{1-3}$ alkoxy (e.g., trifluoromethyloxy, trichloromethyloxy, etc.).

Examples of the heterocyclic group of the optionally substituted heterocyclic group represented by $R^1$ include thienyl (e.g., 2-thienyl, etc.), pyridyl (e.g., 2-pyridyl, etc.), isoxazolyl (e.g., isoxazol-3-yl, isoxazol-5-yl, etc.), benzoxazolyl (e.g., benzoxazol-2-yl, etc.), thiazolyl (e.g., thiazol-2-yl, etc.), benzothiazolyl (e.g., benzothiazol-2-yl, etc.), pyrimidinyl (e.g., pyrimidin-2-yl, pyrimidin-4-yl, etc.), thiadiazolyl (e.g., 1,3,4-thiadiazol-2-yl, etc.), 1,3-dioxolanyl (e.g., 1,3-dioxolan-2-yl, etc.), quinolyl (e.g., 2-quinolyl, etc.), quinoxalinyl (e.g., quinoxalin-2-yl, etc.), etc. In particular, 2-pyridyl is preferred. When the heterocyclic group is substituted, the substituent is selected from the same substituents as those of the optionally substituted phenyl represented by $R^1$ described above. These substituents may be at any possible position in the heterocyclic group.

Examples of the optionally substituted heterocyclic alkyl represented by $R^1$ include that composed of the above optionally substituted heterocyclic group represented by $R^1$ and alkyl having 1 to 4 carbon atoms, such as heterocyclic methyl, heterocyclic ethyl, heterocyclic propyl, etc., each of which may optionally be substituted. In particular, optionally substituted heterocyclic methyl is preferred. The optionally substituted heterocyclic group may be at any possible position in the alkyl. When the heterocyclic group is substituted, the substituent is selected from the same substituens as those of the above optionally substituted phenyl represented by $R^1$. These substituents may be at any possible position in the heterocyclic group.

$R^1$ is preferably optionally substituted phenylalkyl, optionally substituted phenoxyalkyl, optionally substituted heterocyclic group or optionally substituted heterocyclic alkyl.

Examples of the alkyl represented by $R^2$ include alkyl having 1 to 6 carbon atoms such as methyl, ethyl, n-propyl, isopropyl, isobutyl, etc.

Examples of the alkenyl represented by $R^2$ include alkenyl having 2 to 6 carbon atoms such as vinyl, allyl, crotyl, etc. In particular, allyl is preferred.

Examples of the alkynyl represented by $R^2$ include alkynyl having 2 to 6 carbon atoms such as ethynyl, propynyl, butynyl, etc.

Examples of the halogenated alkyl, halogenated alkenyl and halogenated alkynyl represented by $R^2$ include alkyl, alkenyl and alkynyl represented by $R^2$ each of which is substituted with at least one halogen (e.g., fluorine, chlorine, bromine, iodine).

Examples of the cycloalkyl represented by $R^2$ include cycloalkyl having 3 to 8 carbon atoms such as cyclopropyl, cyclobutyl, cyclopentyl, cyclohexyl, etc.

Examples of the optionally substituted phenyl, optionally substituted benzyl, optionally substituted heterocyclic group and optionally substituted heterocyclic alkyl represented by $R^2$ include the same groups as those represented by $R^1$.

$R^2$ is preferably alkyl or alkenyl, more preferably methyl, ethyl or allyl.

Examples of the alkyl represented by $R^3$ include alkyl having 1 to 4 carbon atoms such as methyl, ethyl, propyl, butyl, etc.

Examples of the alkoxy represented by $R^3$ include alkoxy having 1 to 4 carbon atoms such as methoxy, ethoxy, propoxy, butoxy, etc.

Examples of the halogen represented by $R^3$ include fluorine, chlorine, bromine and iodine.

$R^3$ is preferably hydrogen, alkyl, alkoxy or halogen, more preferably hydrogen, methyl, methoxy, fluorine or chlorine. $R^3$ may be at any possible position in the phenyl, preferably at 5-position in the phenyl.

X is preferably O.

Y is preferably CH.

Preferred examples of the compounds of the formula (I) include those wherein $R^1$ is optionally substituted phenylalkyl, optionally substituted phenoxyalkyl or optionally substituted pyridyl; $R^2$ is alkyl; $R^3$ is hydrogen, alkyl, alkoxy or halogen; X is O; and Y is CH.

More preferred examples of the compounds of the formula (I) include:

a compound of the formula (I) wherein $R^1$ is 4-methylphenylmethyl, $R^2$ is methyl, $R^3$ is hydrogen, X is O, and Y is CH (Compound No. 3);

a compound of the formula (I) wherein $R^1$ is 2-chlorophenylmethyl, $R^2$ is methyl, $R^3$ is hydrogen, X is O, and Y is CH (Compound No. 7);

a compound of the formula (I) wherein $R^1$ is 4-methylphenylmethyl, $R^2$ is ethyl, $R^3$ is 5-methyl, X is O, and Y is CH (Compound No. 995);

a compound of the formula (I) wherein $R^1$ is 1-phenylethyl, $R^2$ is methyl, $R^3$ is hydrogen, X is O, and Y is CH (Compound No. 491);

a compound of the formula (I) wherein $R^1$ is 1-phenylethyl, $R^2$ is methyl, $R^3$ is 5-fluoro, X is O, and Y is CH (Compound No. 1101);

a compound of the formula (I) wherein $R^1$ is 5-trifluoromethyl-2-pyridyl, $R^2$ is ethyl, $R^3$ is hydrogen, X is O, and Y is CH (Compound No. 183);

a compound of the formula (I) wherein $R^1$ is 5-trifluoromethyl-2-pyridyl, $R^2$ is methyl, $R^3$ is hydrogen, X is O, and Y is CH (Compound No. 83);

a compound of the formula (I) wherein $R^1$ is 5-trifluoromethyl-2-pyridyl, $R^2$ is methyl, $R^3$ is 5-chloro, X is O, and Y is CH (Compound No. 583);

a compound of the formula (I) wherein $R^1$ is 5-trifluoromethyl-2-pyridyl, $R^2$ is methyl, $R^3$ is 5-fluoro, X is O, and Y is CH (Compound No. 783);

a compound of the formula (I) wherein $R^1$ is 3,5-dichloro-2-pyridyl, $R^2$ is methyl, $R^3$ is 5-chloro, X is O, and Y is CH (Compound No. 581);

a compound of the formula (I) wherein $R^1$ is 3-phenylpropyl, $R^2$ is methyl, $R^3$ is hydrogen, X is O, and Y is CH (Compound No. 497);

a compound of the formula (I) wherein $R^1$ is 2-phenoxylethyl, $R^2$ is methyl, $R^3$ is 5-chloro, X is O, and Y is CH (Compound No. 552);

a compound of the formula (I) wherein $R^1$ is 2-(4-chlorophenoxy)ethyl, $R^2$ is methyl, $R^3$ is hydrogen, X is O, and Y is CH (Compound No. 863);

a compound of the formula (I) wherein $R^1$ is 4-phenoxybutyl, $R^2$ is methyl, $R^3$ is hydrogen, X is O, and Y is CH (Compound No. 495); and a compound of the formula (I) wherein $R^1$ is 4-phenoxybutyl, $R^2$ is ethyl, $R^3$ is hydrogen, X is O, and Y is CH (Compound No. 876). These compound Nos. are those described in Examples hereinafter.

Each compound of the present invention exists as E- or Z-isomer and includes both of the isomers and mixtures thereof in any mixing ratios. This is indicated by the wave line ~ in this specification.

The compound of the present invention also includes its hydrochloric acid salt, sulfuric acid salt, nitric acid salt, oxalic acid salt and p-toluenesulfonic acid salt.

The compound of the formula (I) of the present invention can be prepared, for example, according to the following synthetic routes.

Route 1

Scheme 1

$$R^3 \underset{COOR^4}{\overset{X-H}{\bigcirc}} + R^1-L \xrightarrow{\text{Base}}$$

II     III $$R^3 \underset{COOR^4}{\overset{X-R^1}{\bigcirc}}$$

IV wherein L is halogen, alkylsulfonyl, alkylsulfonyloxy or arylsulfonyloxy; $R^4$ is hydrogen, alkyl or optionally substituted benzyl; and $R^1$, $R^3$ and X are as defined above.

Examples of the halogen represented by L include chlorine, bromine, iodine, etc. Examples of the alkylsulfonyl represented by L include $C_{1-5}$ alkylsulfonyl such as methanesulfonyl, ethanesulfonyl, etc. Examples of the alkylsulfonyloxy represented by L include alkylsulfonyloxy having optionally halogenated $C_{1-5}$ alkyl, such as methanesulfonyloxy, ethanesulfonyloxy, trichloromethanesulfonyloxy, etc. Examples of the arylsulfonyloxy represented by L include optionally substituted benzenesulfonyloxy such as p-toluenesulfonyloxy, benzenesulfonyloxy, etc. Examples of the alkyl represented by $R^4$ include alkyl having 1 to 5 carbon atoms such as methyl, ethyl, isopropyl, etc. Examples of the optionally substituted benzyl represented by $R^4$ include benzyl optionally substituted with the same substituent(s) as those of the above optionally substituted phenyl represented by $R^1$, such as benzyl, 4-chlorobenzyl, 4-methylbenzyl, etc.

The compound (IV) can be prepared by reacting the compound (II) with the compound (III) in the presence of a base in the absence of a solvent or in an appropriate solvent.

The amount of the compound (III) to be used is 1 mol or more, preferably 1 to 3 mol per mol of the compound (II).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydride, etc.), amines (e.g., pyridine, triethylamine, etc.), etc. The amount of the base to be used is 1 mol or more, preferably 1 to 3 mol per mol of the compound (II).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvents can be used alone or in combination thereof.

The reaction temperature is normally -10° C. to 200° C., preferably 0° C. to 180° C. The reaction time varies with the compounds but is generally 0.5 to 48 hours.

The compound (IV) thus obtained can be used in the next step as the reaction mixture or crude product, or after purification by conventional methods (e.g., chromatography, recrystallization, etc.).

Alternatively, the compound (IV) can also be prepared by the following reaction.

Route 1 (continued)

Scheme 2

$$R^3 \underset{COOR^4}{\overset{L}{\bigcirc}} + R^1-XH \xrightarrow{\text{Base}}$$

V     VI $$R^3 \underset{COOR^4}{\overset{X-R^1}{\bigcirc}}$$

IV wherein each symbol is as defined above.

That is, the compound (IV) can be prepared by reacting the compound (V) with the compound (VI) in the presence of a base in the absence of a solvent or in an appropriate solvent.

The amount of the compound (VI) to be used is 1 mol or more, preferably 1 to 3 mol per mol of the compound (V).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydride, etc.), amines (e.g., pyridine, triethylamine, etc.), etc. The amount of the base to be used is 1 mol or more, preferably 1 to 3 mol per mol of the compound (II).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvents can be used alone or in combination thereof.

The reaction temperature is normally −10° C. to 200° C., preferably 0° C. to 180° C. The reaction time varies with the compounds but is generally 0.5 to 48 hours.

The compound (IV) thus obtained can be used in the next step as the reaction mixture or crude product, or after purification by conventional methods (e.g., chromatography, recrystallization, etc.).

Route 1 (continued)

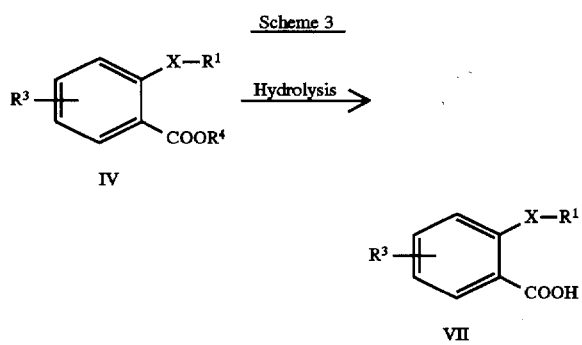

wherein each symbol is as defined above.

The compound (VII) can be prepared by reacting the compound (IV) with a base or acid in an appropriate solvent to hydrolyze the compound (IV).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), etc. Examples of the acid include hydrochloric acid, sulfuric acid, hydrobromic acid, p-toluenesulfonic acid, etc. The amount of the base or acid to be used is 1 mol or more, preferably 1 to 3 mol per mol of the compound (IV).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclethanol, isopropanol,), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvents can be used alone or in combination thereof.

The reaction temperature is normally −10° C. to 150° C., preferably 0° C. to 120° C. The reaction time varies with the compounds but is generally 0.1 to 48 hours.

The compound (VII) thus obtained can be used in the next step as the reaction mixture or crude product, or after purification by conventional methods (e.g., chromatography, recrystallization, etc.).

Route 1 (continued)

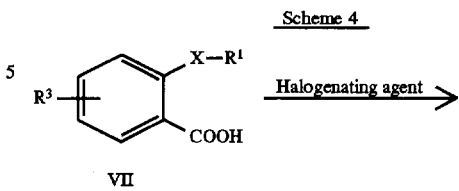

wherein A is halogen, and the other symbols are as defined above.

Examples of the halogen represented by A include fluorine, chlorine, bromine and iodine. It is preferably chlorine or bromine.

The compound (VIII) can be prepared by reacting the compound (VII) with a halogenating agent in the absence of a solvent or in an appropriate solvent in the presence or absence of a catalyst.

Examples of the halogenating agent include thionyl halides (e.g., thionyl chloride, thionyl bromide, etc.), phosphoryl halides (e.g., phosphoryl chloride, phosphoryl bromide, etc.), phosphorus halides (e.g., phosphorus pentachloride, phosphorus trichloride, phosphorus pentabromide, phosphorus tribromide, etc.), phosgene, oxalyl halides (e.g., oxalyl chloride, etc.), etc. The amount of the halogenating agent to be used is 1 mol or more, preferably 1 to 10 mol per mol of the compound (VII).

Examples of the catalyst include DMF, DMSO, HMPA, pyridine, triethylamine, iodine, zinc chloride, Vilsmeier reagent, etc. The amount of the catalyst to be used is 0.005 to 3 mol, preferably 0.01 to 1 mol per mol of the compound (VII).

Examples of the reaction solvent include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), etc. These solvents can be used alone or in combination thereof.

The reaction temperature is normally −10° C. to 150° C., preferably 0° C. to 120° C. The reaction time varies with the compounds but is generally 0.1 to 48 hours.

The compound (VIII) thus obtained can be used in the next step as the reaction mixture or crude product, or after purification by conventional methods (e.g., chromatography, recrystallization, etc.).

Route 1 (continued)

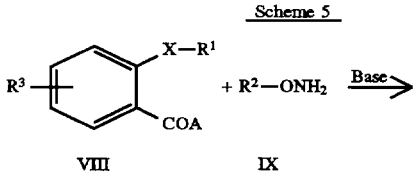

-continued
Scheme 5

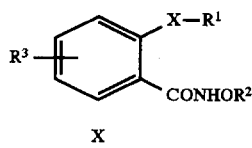

wherein each symbol is as defined above.

The compound (X) can be prepared by reacting the compound (VIII) with the compound (IX) or a salt thereof (e.g., hydrochloric acid salt, sulfuric acid salt, etc.) in the presence of a base in the absence of a solvent or in an appropriate solvent.

The amount of the compound (IX) to be used is 1 mol or more, preferably 1 to 3 mol per mol of the compound (VIII).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), amines (e.g., pyridine, triethylamine, etc.), etc. The amount of the base to be used is 1 mol or more, preferably 1 to 3 mol per mol of the compound (VIII).

Examples of the solvent include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), ethers (e.g., THF, dioxane, etc.), water, etc. These solvents can be used alone or in combination thereof.

The reaction temperature is normally $-30°$ C. to $150°$ C., preferably $-10°$ C. to $100°$ C. The reaction time varies with the compounds but is generally 0.5 to 48 hours.

The compound (X) thus obtained can be used in the next step as the reaction mixture or crude product, or after purification by conventional methods (e.g., chromatography, recrystallization, etc.).

Route 1 (continued)

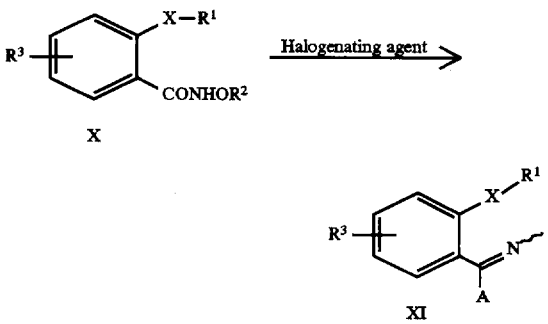

wherein each symbol is as defined above.

The compound (XI) can be prepared by reacting the compound (X) with a halogenating agent in the absence of a solvent or in an appropriate solvent.

Examples of the halogenating agent include thionyl halides (e.g., thionyl chloride, thionyl bromide, etc.), phosphoryl halides (e.g., phosphoryl chloride, phosphoryl bromide, etc.), phosphorus halides (e.g., phosphorus pentachloride, phosphorus trichloride, phosphorus pentabromide, phosphorus tribromide, etc.), phosgene, oxalyl halides (e.g., oxalyl chloride, etc.), triphenylphosphine/carbon tetrachloride, triphenylphosphine/carbon tetrabromide, etc. The amount of the halogenating agent to be used is 1 mol or more, preferably 1 to 10 mol per mol of the compound (X).

Examples of the solvent include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), nitriles (e.g., acetonitrile, propionitrile, etc.), etc. These solvents can be used alone or in combination thereof.

The reaction temperature is normally $-30°$ C. to $150°$ C., preferably $-10°$ C. to $120°$ C. The reaction time varies with the compounds but is generally 0.1 to 48 hours.

The compound (XI) thus obtained can be used in the next step as the reaction mixture or crude product, or after purification by conventional methods (e.g., chromatography, recrystallization, etc.).

Route 1 (continued)

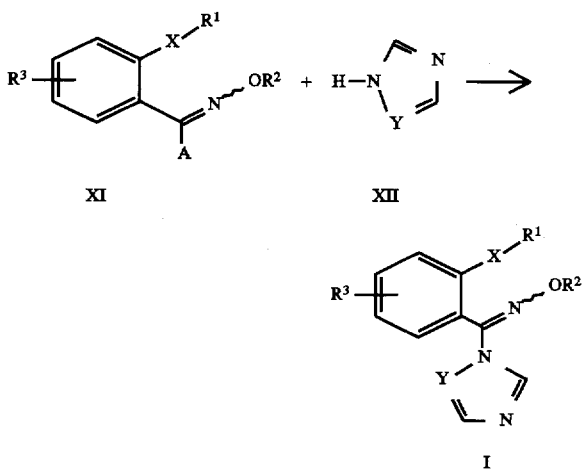

wherein each symbol is as defined above.

The compound of the formula (I) of the present invention can be prepared by reacting the compound (XI) with the compound (XII) in the presence or absence of a base in the absence of a solvent or in an appropriate solvent.

The amount of the compound (XII) to be used is 1 mol or more, preferably 1 to 6 mol per mol of the compound (XI).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydrides, etc.), amines (e.g., triethylamine, etc.), etc. The amount of the base to be used is 1 mol or more, preferably 1 to 3 mol per mol of the compound (XI).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvents can be used alone or in combination thereof.

The reaction temperature is normally $-10°$ C. to $200°$ C., preferably $0°$ C. to $180°$ C. The reaction time varies with the compounds but is generally 0.5 to 48 hours.

The desired compound (I) thus obtained can be purified by conventional methods (e.g., chromatography, recrystallization, etc.).

Alternatively, the compound (I) of the present invention can be prepared by the following route.

Route 2

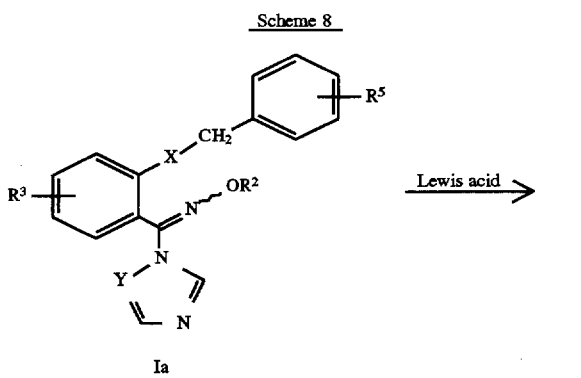

Scheme 8

Ia wherein $R^5$ is hydrogen, $C_{1-5}$ alkyl (e.g., methyl, ethyl, isopropyl, etc.) or halogen (e.g., fluorine, chlorine, bromine, iodine), and the other symbols are as defined above.

The compound (XIII) can be prepared by treating the compound (Ia) with a Lewis acid in an appropriate solvent.

Examples of the Lewis acid include aluminium chloride, aluminium bromide, boron trifluoride, boron tribromide, boron trichloride, ferric chloride, etc. In particular, aluminium chloride is preferred. The amount of the Lewis acid to be used is 1 mol or more, preferably 1 to 3 mol per mol of the compound (Ia).

Examples of the solvent include anisole, nitromethane, nitroethene, etc. These solvents can be used alone or in combination thereof.

The reaction temperature is normally −50° C. to 150° C., preferably, −20° C. to 100° C. The reaction time varies with the compounds but is generally 0.5 to 48 hours.

The compound (XIII) thus obtained can be used in the next step as the reaction mixture or crude product, or after purification by conventional methods (e.g., chromatography, recrystallization, etc.).

Route 2 (continued)

Scheme 9-1

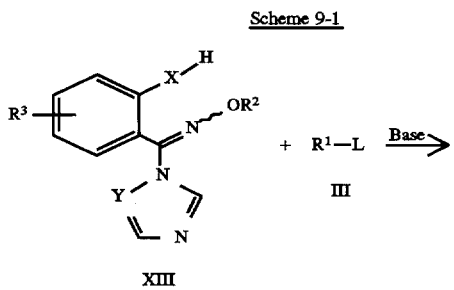

XIII

-continued
Scheme 9-1

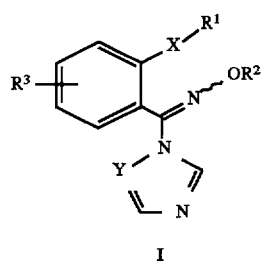

I wherein each symbol is as defined above.

The compound of the formula (I) of the present invention can be prepared by reacting the compound (XIII) with the compound (III) in the presence of a base in the absence of a solvent or in an appropriate solvent.

The amount of the compound (III) to be used is 1 mol or more, preferably 1 to 3 mol per mol of the compound (XIII).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydrides, etc.), amines (e.g., pyridine, triethylamine, etc.), etc. The amount of the base to be used is 1 mol or more, preferably 1 to 3 mol per mol of the compound (XIII).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvents can be used alone or in combination thereof.

The reaction temperature is normally −10° C. to 200° C., preferably 0° C. to 180° C. The reaction time varies with the compounds but is generally 0.5 to 48 hours.

The desired compound (I) thus obtained can be purified by conventional methods (e.g., chromatography, recrystallization, etc.).

Route 2 (continued)

Scheme 9-2

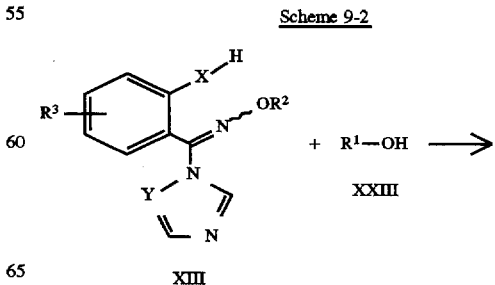

XIII

-continued
Scheme 9-2

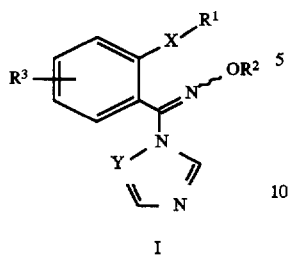

I wherein each symbol is as defined above.

The compound of the formula (I) of the present invention can be prepared by reacting the compound (XIII) with the compound (XXIII) in the presence of triphenylphosphine and diethyl azodicarboxylate or dimethyl azodicarboxylate in the absence of a solvent or in an appropriate solvent.

The amount of the compound (XXIII) to be used is 1 mol or more, preferably 1 to 3 mol per mol of the compound (XIII). The amount of the triphenylphosphine to be used is 1 to 5 mol, preferably 1 to 3 mol per mol of the compound (XIII). The amount of the diethyl azodicarboxylate or dimethyl azodicarboxylate to be used is 1 to 5 mol, preferably 1 to 3 mol per mol of the compound (XIII).

Examples of the solvent include aromatic hydrocarbons (e.g., toluene, benzene, xylene, etc.), saturated hydrocarbons (e.g., cyclohexane, hexane, etc.), ethers (e.g., tetrahydrofuran (THF), dioxane, etc.), nitriles (e.g., acetonitrile, etc.), etc. These solvents can be used alone or in combination thereof.

The reaction temperature is normally −10° C. to 200° C., preferably 0° C. to 120° C. The reaction time varies with the compounds but is generally 0.5 to 72 hours.

The desired compound (I) thus obtained can be purified by conventional methods (e.g., chromatography, recrystallization, etc.).

Alternatively, the compound (I) of the present invention can be prepared in one step from the intermediate (X) in the above Route 1 (Scheme 6) by the following reaction.

Route 3

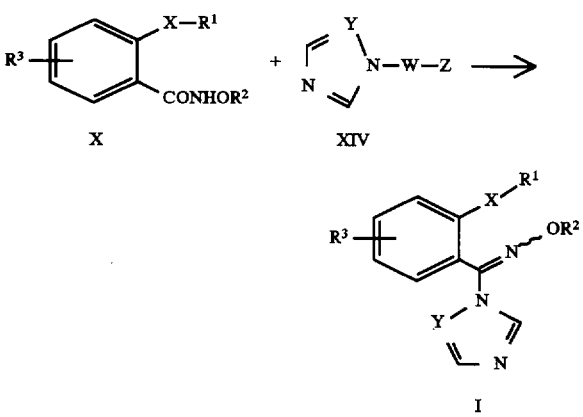

wherein W is carbonyl or sulfinyl, Z is chlorine, bromine or

and the other symbols are as defined above.

The compound of the formula (I) of the present invention can be prepared by reacting the compound (X) with the compound (XIV) in the absence of a solvent or in an appropriate solvent.

The amount of the compound (XIV) to be used is 1 mol or more, preferably 1 to 3 mol per mol of the compound (X).

Examples of the solvent include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), etc. These solvents can be used alone or in combination thereof.

The reaction temperature is normally −30° C. to 150° C., preferably −10° C. to 120° C. The reaction time varies with the compounds but is generally 0.1 to 48 hours.

The desired compound (I) thus obtained can be purified by conventional methods (e.g., chromatography, recrystallization, etc.).

The compound (XIII) in above Route 2 (Scheme 9) can also be prepared by the following reaction.

Scheme 11

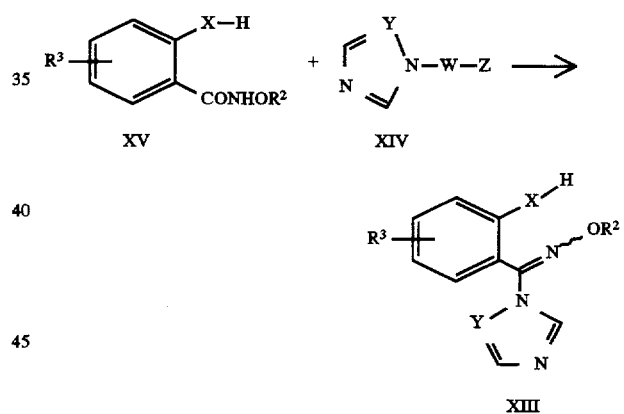

wherein each symbol is as defined above.

The compound (XIII) can be prepared by reacting the compound (XV) with the compound (XIV) in the absence of a solvent or in an appropriate solvent.

The amount of the compound (XIV) to be used is 1 mol or more, preferably 1 to 3 mol per mol of the compound (XV).

Examples of the solvent include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, etc.), etc. These solvents can be used alone or in combination thereof.

The reaction temperature is normally −30° C. to 150° C., preferably −10° C. to 120° C. The reaction time varies with the compounds but is generally 0.1 to 48 hours.

Alternatively, the compound (I) of the present invention can be prepared by the following route.

Route 5

Scheme 12

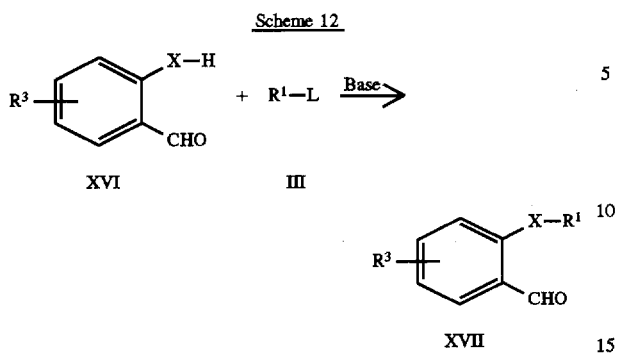

wherein each symbol is as defined above.

The compound (XVII) can be prepared by reacting the compound (XVI) with the compound (III) in the presence of a base in the absence of a solvent or in an appropriate solvent.

The amount of the compound (III) to be used is 1 mol or more, preferably 1 to 3 mol per mol of the compound (XVI).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydrides, etc.), amines (e.g., pyridine, triethylamine, etc.), etc. The amount of the base to be used is 1 mol or more, preferably 1 to 3 mol per mol of the compound (XVI).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvents can be used alone or in combination thereof.

The reaction temperature is normally −10° C. to 200° C., preferably 0° C. to 180° C. The reaction time varies with the compounds but is generally 0.5 to 48 hours.

The compound (XVII) thus obtained can be used in the next step as the reaction mixture or crude product, or after purification by conventional methods (e.g., chromatography, recrystallization, etc.).

Alternatively, the compound (XVII) can also be prepared by the following reaction.

Route 5 (continued)

Scheme 13

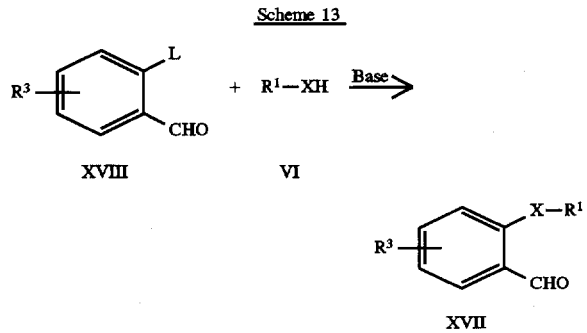

wherein each symbol is as defined above.

The compound (XVII) can be prepared by reacting the compound (XVIII) with the compound (VI) in the presence of a base in the absence of a solvent or in an appropriate solvent.

The amount of the compound (VI) to be used is 1 mol or more, preferably 1 to 3 mol per mol of the compound (XVIII).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydrides, etc.), amines (e.g., pyridine, triethylamine, etc.), etc. The amount of the base to be used is 1 mol or more, preferably 1 to 3 mol per mol of the compound (XVIII).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvents can be used alone or in combination thereof.

The reaction temperature is normally −10° C. to 200° C., preferably 0° C. to 180° C. The reaction time varies with the compounds but is generally 0.5 to 48 hours.

The compound (XVII) thus obtained can be used in the next step as the reaction mixture or crude product, or after purification by conventional methods (e.g., chromatography, recrystallization, etc.).

Route 5 (continued)

Scheme 14

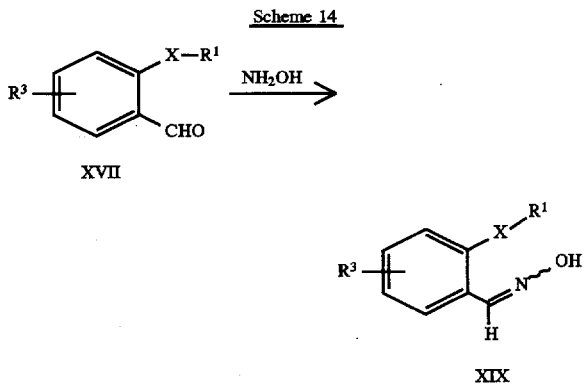

wherein each symbol is as defined above.

The compound (XIX) can be prepared by reacting the compound (XVII) with hydroxylamine or a salt thereof (e.g., hydrochloric acid salt, sulfuric acid salt, etc.) in the presence or absence of a base in the absence of a solvent or in an appropriate solvent.

The amount of the hydroxylamine to be used is 1 mol or more, preferably 1 to 3 mol per mol of the compound (XVII).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), amines (e.g., pyridine, triethylamine, etc.), etc. The amount of the base to be used is 1 mol or more, preferably 1 to 3 mol per mol of the compound (XVII).

Examples of the solvent include aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), water, etc. These solvents can be used alone or in combination thereof.

The reaction temperature is normally −30° C. to 150° C., preferably −10° C. to 100° C. The reaction time varies with the compounds but is generally 0.5 to 48 hours.

The compound (XIX) thus obtained can be used in the next step as the reaction mixture or crude product, or after purification by conventional methods (e.g., chromatography, recrystallization, etc.).

Route 5 (continued)

Scheme 15

XIX

XX wherein each symbol is as defined above.

The compound (XX) can be prepared by reacting the compound (XIX) with a halogenating agent in the absence of a solvent or in an appropriate solvent.

Examples of the halogenating agent include halogen (e.g., chlorine, bromine, etc.), N-halosuccinimide (e.g., N-bromosuccinimide, N-chlorosuccinimide, etc.), etc. The amount of the halogenating agent to be used is 1 mol or more, preferably 1 to 3 mol per mol of the compound (XIX).

Examples of the solvent include aromatic hydrocarbons (e.g., toluene, benzene, xylene, etc.), saturated hydrocarbons (e.g., cyclohexane, hexane, etc.), halogenated hydrocarbons (e.g., dichloromethane, 1,2-dichloroethane, chloroform, carbon tetrachloride, etc.), ethers (e.g., diethyl ether, dioxane, tetrahydrofuran (THF), etc.), etc. These solvents can be used alone or in combination thereof.

The reaction temperature is normally −30° C. to 150° C., preferably −10° C. to 120° C. The reaction time varies with the compounds but is generally 0.1 to 48 hours.

The compound (XX) thus obtained can be used in the next step as the reaction mixture or crude product, or after purification by conventional methods (e.g., chromatography, recrystallization, etc.).

Route 5 (continued)

Scheme 16

XX    XII

-continued
Scheme 16

Ib wherein each symbol is as defined above.

The compound (Ib) of the present invention can be prepared by reacting the compound (XX) with the compound (XII) in the presence or absence of a base in the absence of a solvent or in an appropriate solvent.

The amount of the compound (XII) to be used is 1 mol or more, preferably 1 to 6 mol per mol of the compound (XX).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydrides, etc.), amines (e.g., triethylamine, etc.), etc. The amount of the base to be used is 1 mol or more, preferably 1 to 3 mol per mol of the compound (XX).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, methyl ethyl ketone, etc.), nitriles (e.g., acetonitrile, etc.), etc. These solvents can be used alone or in combination thereof.

The reaction temperature is normally −10° C. to 200° C., preferably 0° C. to 180° C. The reaction time varies with the compounds but is generally 0.5 to 48 hours.

The compound (Ib) can be purified by conventional methods (e.g., chromatography, recrystallization, etc.). When the compound (Ib) is used in the next step, it can be used as the reaction mixture or crude product, or after purification by conventional methods (e.g., chromatography, recrystallization, etc.).

Route 5 (continued)

Scheme 17

Ib    + R²—L    Base→

XXII

-continued
Scheme 17

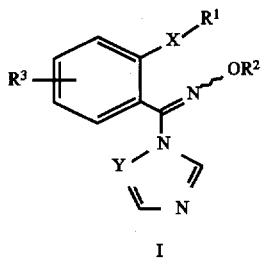

I wherein each symbol is as defined above.

The compound (I) of the present invention can be prepared by reacting the compound (Ib) with the compound (XXII) in the presence of a base in the absence of a solvent or in an appropriate solvent.

The amount of the compound (XXII) to be used is 1 mol or more, preferably 1 to 3 mol per mol of the compound (Ib).

Examples of the base include metal hydroxides (e.g., sodium hydroxide, potassium hydroxide, etc.), metal carbonates (e.g., sodium carbonate, potassium carbonate, etc.), metal alkoxides (e.g., sodium methoxide, sodium ethoxide, potassium tert-butoxide, etc.), metal hydrides (e.g., sodium hydrides, etc.), amines (e.g., pyridine, triethylamine, etc.), etc. The amount of the base to be used is 1 mol or more, preferably 1 to 3 mol per mol of the compound (Ib).

Examples of the solvent include N,N-dimethylformamide (DMF), dimethyl sulfoxide (DMSO), hexamethylphosphoric triamide (HMPA), aromatic hydrocarbons (e.g., toluene, benzene, xylene, etc.), saturated hydrocarbons (e.g., cyclohexane, hexane, etc.), alcohols (e.g., methanol, ethanol, isopropanol, butanol, etc.), ethers (e.g., tetrahydrofuran (THF), dioxane, etc.), halogenated hydrocarbons (e.g., dichloromethane, 1,2-dichloroethane, etc.), ketones (e.g., acetone, ethyl methyl ketone, etc.), nitriles (e.g., acetonitrile, etc.), water, etc. These solvent can be used alone or in combination thereof.

The reaction temperature is normally −10° C. to 200° C., preferably 0° C. to 180° C. The reaction time varies with the compounds but is generally 0.5 to 48 hours.

The desired compound (I) thus obtained can be purified by conventional methods (e.g., chromatography, recrystallization, etc.).

The compounds of the formula (I) of the present invention show a strong fungicidal activity against a wide variety of phytopathogenic fungi on crop plants (e.g., rice, wheat, barley, rye, corn, common millet, millet, buckwheat, soybean, redbean, peanut, etc.), fruit trees (e.g., citrus fruits, grape, apple, pear, peach, etc.), vegetables (e.g., cucumber, eggplant, tomato, pumpkin, kidney bean, etc.), etc. They also show fungicidal activity against phytopathogenic fungi in soil. Examples of the phytopathogenic fungi on which the compounds of the formula (I) of the present invention exert their fungicidal activity are *Pyricularia oryzae, Rhizoctonia solani, Erysiphe graminis, Sphaerotheca fuliginea, Erysiphe cichoracearum, Phytophthora infestans, Pseudoperonospora cubensis, Peronospora manshurica, Plasmopara viticola, Botrytis cinerea* of vegetables, grape, etc., *Pythium aphanidermatum, Sclerotinia sclerotiorum* of buckwheat, soybean, colza, etc., *Corticium rolfsii* of soybean, redbean, potato, peanut, etc., *Pseudocercosporella herpotrichoides*, etc. Therefore, the compounds (I) of the present invention are useful as agricultural fungicides.

Application of the compounds (I) of the present invention may be made to plants by any conventional procedure such as atomizing, scattering or spreading. Application may also be made through treatment of seeds of plants, soil where plants grow, paddy field for seedling or water for perfusion with the compounds (I). Application may be performed before and/or after the infection with phytopathogenic fungi on plants.

For the practical usage, the compounds (I) may be applied as such or in a formulation form suitable for agricultural fungicides such as solutions, wettable powders, emulsions, suspensions, concentrated liquid preparations, tablets, granules, aerosols, powders, pastes, dusts, etc. Such formulation can be prepared in a conventional manner by mixing at least one of the compounds (I) with an appropriate solid or liquid carrier(s) and, if necessary, an appropriate adjuvant (s) (e.g., surfactants, spreaders, dispersants, stabilizers, etc.) for improving the dispersibility and other properties of the active ingredient.

Examples of the solid carriers or diluents include botanical materials (e.g., flour, tobacco stalk powder, soybean powder, walnut-shell powder, vegetable powder, saw dust, bran, bark powder, cellulose powder, vegetable extract residue, etc.), fibrous materials (e.g., paper, corrugated cardboard, old rags, etc.), artificial plastic powders, clays (e.g., kaolin, bentonite, fuller's earth, etc.), talc, other inorganic materials (e.g., pyrophyllite, sericite, pumice, sulfur powder, active carbon, etc.), chemical fertilizers (e.g., ammonium sulfate, ammonium phosphate, ammonium nitrate, urea, ammonium chloride, etc.), etc.

Examples of the liquid carriers or diluents include water, alcohols (e.g., methanol, ethanol, etc.), ketones (e.g., acetone, ethyl methyl ketone, etc.), ethers (e.g., diethyl ether, dioxane, cellosolve, tetrahydrofuran, etc.), aromatic hydrocarbons (e.g., benzene, toluene, xylene, methylnaphthalene, etc.), aliphatic hydrocarbons (e.g., gasoline, kerosene, lamp oil, etc.), esters, nitriles, acid amides (e.g., N,N-dimethylformamide, N,N-dimethylacetamide, etc.), halogenated hydrocarbons (e.g., dichloroethane, carbon tetrachloride, etc.), etc.

Examples of the surfactants include alkyl sulfates, alkyl sulfonates, alkylaryl sulfonates, polyethylene glycol ethers, polyhydric alcohol esters, etc.

Examples of the spreaders or dispersants include casein, gelatin, starch powder, carboxymethyl cellulose, gum arabic, alginic acid, lignin, bentonite, molasses, polyvinyl alcohol, pine oil, agar, etc.

Examples of the stabilizers include PAP (a mixture of isopropylphosphate), tricresyl phosphate (TCP), tolu oil, epoxidized oil, surfactants, fatty acids and their esters, etc.

The composition of the present invention may contain other fungicides, insecticides, herbicides, fertilizers, etc., in addition to the above components.

When the compounds (I) are used as fungicidal compositions, each of such compositions contains at least one of the compounds (I) in a concentration of normally 0.1 to 95% by weight, preferably 2.0 to 80% by weight. These compositions can be used as such or in a diluted form. The concentration to be used depends upon a particular purpose, subject and plant to be treated, and it is generally in the range of about 1 to 50,000 ppm, preferably about 100 to 5,000 ppm. The amount of the compound (I) to be used is generally about 1.0 g to 5 kg/hectare, preferably about 2 g to 100 g/hectare.

Further, the compounds (I) of the present invention have excellent herbicidal activity against gramineous and broadleaved weeds such as *Digitaria ciliaris, Setaria viridis, Echinochloa crus-galli, Amaranthus lividus, Chenopodium album, Cyperus microiria, Mollugo stricta, Stellaria neglecta, Sagina japonica, Stellaria Alsine* GRIMM var.

undulata, *Capsella bursa-pastoris*, *Alopecurus aequalis* SOBOL var. *amurensis*, *Poa annua*, *Polygonum longisetum*, *Polygonum lapathifolium*, *Trigonotis peduncularis*, upland weeds such as *Gnaphalium affine*, paddy weeds such as *Echinochloa oryzicola*, *Monochoria vaginalis*, *Cyperus difformis*, *Rotala indica*, *Dopatrium junceum*, etc.

Further, the compounds (I) also have growth regulating activity (e.g., growth inhibiting activity) against gramineous and broad-leaved weeds, particularly lawns and balk weeds, and can inhibit the growth of grasses in paddy balks or lawns of golf courses for a long term.

The compounds (I) in certain amounts (e.g., 1 to 40 g/a) cause no or little damage to useful plants such as corn, sugarcane, sorghum, rice, wheat, barley, rye, soybean, peanut, cotton, etc. Even when the damage is caused, the damage is so slight that the damaged plants can readily recovered. Therefore, the compounds (I) can be used as selective or nonselective herbicides or growth regulating compositions (e.g., growth inhibiting compositions, compositions for reducing cutting frequency, and compositions for making felling easy, etc.) in arables such as plowed fields, paddy fields, fruit gardens, tea gardens, mulberry fields, arable lands not being used, pastures, and untillable lands such as railroads, roads, lawns, factory sites, riverbeds, housing lands, green tracts in parks, forests, created lands, vacant lands, etc.

The compounds (I) are harmless to humans, domestic animals and birds, and the toxicity to fishes is extremely low. Therefore the herbicides and growth regulating compositions are safe and the residual toxicity does not become a problem.

The compounds (I) can be used as herbicides or growth regulating compositions in various manners depending on the purpose, subject plants, term for use, etc. In general, treatment of soil or foliage application are preferred for the use as herbicides and foliage application is preferred for the use as growth regulating compositions. Each of such herbicidal compositions and growth regulating compositions contains at least one of the compounds (I) in a concentration of normally 0.1 to 95% by weight, preferably 2 to 80% by weight. These compositions can be used as such or in a diluted form. The concentration to be used depends upon a particular purpose, subject and plant to be treated, and it is generally in the range of about 1 to 50,000 ppm, preferably about 100 to 5,000 ppm. The amount of the compounds (I) to be used is generally about 10 g to 5 kg/hectare, preferably about 100 g to 1,000 g/hectare.

When the compounds (I) are used as herbicides or growth regulating compositions, the compounds (I) are used as such or in a formulation form such as powders, wettable powders, emulsions, etc., prepared by mixing various carriers depending on the sites where the compounds are applied. The carriers may be solid, liquid or combinations thereof. Examples of the solid carriers include clays, talc, diatomaceous earth, bentonite, etc. Examples of the liquid carriers include water, alcohols (e.g., methanol, ethanol, etc.), acetone, benzene, toluene, xylene, solvent naphtha, cyclohexane, etc. In addition, agriculturally acceptable emulsifying agents, stabilizers, dispersants, suspending agents, spreaders, penetrating agents, wetting agents, etc., can be formulated.

To increase the activity or obtain additive or synergistic action, the herbicides can be used in combination with other herbicides such as diuron, MCP, CNP, IPC, asulam, alachlor, trifluralin, etc. The herbicides or the growth regulating compositions of the present invention can also be used as a mixture with insecticides, fungicides, fertilizers, soil treating (improving) agents, etc.

Further, the benzaldehyde oxime derivatives of the present invention also have strong fungicidal activity against pathogenic fungi such as Candida, Aspergillus, Trichophyton, etc., and can be used as antifungal agents for treating such infectious diseases.

As described hereinabove, according to the present invention, there are provided novel benzaldehyde oxime derivatives, processes for producing them, and fungicidal, herbicidal and growth regulating compositions containing them as active ingredients.

The following examples and experiments further illustrate the present invention in detail, but are not to be construed to limit the scope thereof.

EXAMPLE 1

Synthesis of 2-(2,4-dichlorobenzyloxy)benzoic acid

Dimethylformamide (DMF)(100 ml), potassium carbonate (17.97 g) and 2,4-dichlorobenzyl chloride (21.50 g) were added to methyl salicylate (15.22 g), and the mixture was stirred at room temperature overnight. Ethyl acetate (1000 ml) was added to the reaction mixture, and the resulting mixture was washed with brine (700 ml) twice, dried over anhydrous magnesium sulfate and concentrated under reduced pressure to give crude methyl 2-(2,4-dichlorobenzyloxy)benzoate. Methanol (100 ml), THF (100 ml), water (20 ml) and 85% potassium hydroxide (7.92 g) were added to the crude product thus obtained, and the mixture was stirred at 60° C. for 2 hours. After completion of the reaction, the mixture was concentrated under reduced pressure. Water (300 ml) was added to the residue, and the pH of the mixture was adjusted to not more than 2, and the resulting crystals were separated by filtration, dried to give 2-(2,4-dichlorobenzyloxy)benzoic acid (29.30 g) as colorless crystals.

EXAMPLE 2

Synthesis of 2-(2,4-dichlorobenzyloxy)-N-methoxybenzamide

Dry dichloroethane (80 ml), thionyl chloride (3.16 ml) and DMF (0.2 ml) were added to 2-(2,4-dichlorobenzyloxy) benzoic acid (11.89 g), and the mixture was stirred under reflux for 1 hour. After completion of the reaction, the mixture was concentrated under reduced pressure, the residue was dissolved in dry methylene chloride (80 ml), the solution was added dropwise to a mixture of methoxyamine hydrochloride (6.68 g), pyridine (9.49 g) and methylene chloride (40 ml) under ice-cooling over 15 minutes, and the resulting mixture was stirred at room temperature for 1 hour. To the reaction mixture was added 1N hydrochloric acid (300 ml), and the resulting mixture was extracted with methylene chloride (150 ml) twice, dried over anhydrous magnesium sulfate and concentrated under reduced pressure. The resulting crude crystals were recrystallized from ethyl acetate/n-hexane to give 2-(2,4-dichlorobenzyloxy)-N-methoxybenzamide (10.81 g) as colorless crystals. mp 100°–101.5° C.

EXAMPLE 3

Synthesis of α-chloro-2-(2,4-dichlorobenzyloxy) benzaldehyde O-methyloxime 2-(2,4-Dichlorobenzyloxy)-N-methoxybenzamide (10.44 g) was dissolved in dry methylene chloride (100 ml), phosphorus pentachloride (6.66 g) was added under ice-cooling over about 3 minutes to the solution, and the mixture was stirred at 0° C. for 1 hour. After completion of the reaction, a saturated aqueous solution of sodium bicarbonate (150 ml) was added slowly, and the mixture was extracted with methylene chloride (150 ml) twice, dried over anhydrous magnesium sulfate and concentrated under reduced pressure. The resulting crude product was purified by silica gel chromatography to give α-chloro-2-(2,4-dichlorobenzyloxy)benzaldehyde O-methyloxime (9.52 g) as crystals. A part of the crystals was recrystallized from ethyl acetate/n-hexane to give colorless crystals. mp 91°–92° C.

EXAMPLE 4

Synthesis of 2-(2,4-dichlorobenzyloxy)-α-(1-imidazolyl)benzaldehyde O-methyloxime (Compound 31)

Imidazole (2.04 g) was dissolved in DMF (30 ml), and 60% sodium hydride (1.20 g) was added. The mixture was stirred at room temperature for 10 minutes, then α-chloro-2-(2,4-dichlorobenzyloxy)benzaldehyde O-methyloxime (5.17 g) was added, and the mixture was stirred at 120° C. for 2 hours. After completion of the reaction, ether (200 ml) was added, and the mixture was washed with brine (200 ml) twice, dried over anhydrous magnesium sulfate and concentrated under reduced pressure. The resulting crude product was purified by silica gel chromatography and recrystallized from ethyl acetate/n-hexane to give 2-(2,4-dichlorobenzyloxy)-α-(1-imidazolyl)benzaldehyde O-methyloxime (2.74 g) as colorless crystals. mp. 122°–123° C.

EXAMPLE 5

Synthesis of 2-(4-chlorobenzylthio)-α-(1-imidazolyl)benzaldehyde O-ethyloxime (Compound No. 155)

DMF (3 ml) and imidazole (0.41 g) were added to α-chloro-2-(4-chlorobenzylthio)benzaldehyde O-ethyloxime (0.68 g), and the mixture was stirred at 170° C. for 21 hours. After completion of the reaction, ether (100 ml) was added, and the mixture was washed with brine (80 ml) twice, dried over anhydrous magnesium sulfate and concentrated under reduced pressure. The resulting crude product was purified by silica gel chromatography and recrystallized from ethyl acetate/n-hexane to give 2-(4-chlorobenzylthio)-α-(1-imidazolyl)benzaldehyde O-ethyloxime (0.11 g) as colorless crystals. mp. 96.5°–97.5° C.

EXAMPLE 6

Synthesis of 2-hydroxy-α-(1-imidazolyl) benzaldehyde O-methyloxime

Dry anisole (6 ml) and aluminium chloride (0.59 g) were added to 2-(2,4-dichlorobenzyloxy)-α-(1-imidazolyl) benzaldehyde O-methyloxime (0.75 g), and the mixture was stirred under ice-cooling for 2 hours. After completion of the reaction, a half-saturated aqueous solution of sodium bicarbonate (100 ml) was added slowly, and the mixture was extracted with ether (50 ml) and ethyl acetate (50 ml), dried over anhydrous magnesium sulfate and concentrated under reduced pressure. The resulting crude product was purified by silica gel chromatography and recrystallized from ethyl acetate/n-hexane to give 2-hydroxy-α-(1-imidazolyl) benzaldehyde O-methyloxime (0.34 g) as colorless crystals. mp. 103.5°–104.5° C.

EXAMPLE 7

Synthesis of α-(1-imidazolyl)-2-(4-methylbenzyloxy) benzaldehyde O-methyloxime (Compound 3)

DMF (3 ml), potassium carbonate (0.22 g) and 4-methylbenzyl chloride (0.20 g) were added to 2-hydroxy-α-(1-imidazolyl)benzaldehyde O-methyloxime (0.26 g), and the mixture was stirred at room temperature overnight. After completion of the reaction, ether (100 ml) was added, and the mixture was washed with brine (80 ml) twice, dried over anhydrous magnesium sulfate and concentrated under reduced pressure. The resulting crude product was purified by silica gel chromatography and recrystallized from ethyl acetate/n-hexane to give α-(1-imidazolyl)-2-(4-methylbenzyloxy)benzaldehyde O-methyloxime (0.22 g) as colorless crystals. mp. 70.5°–72.0° C.

EXAMPLE 8

Synthesis of 2-(4-chlorobenzyloxy)-α-(1-imidazolyl)benzaldehyde O-methyloxime (Compound 9)

Thionyl chloride (0.16 ml) was added to a suspension of imidazole (0.63 g) and methylene chloride (6 ml) under ice-cooling, and the mixture was stirred under ice-cooling for 30 minutes. Then 2-(4-chlorobenzyloxy)-N-methoxybenzamide (0.44 g) was added, and the mixture was stirred under reflux for 2 hours. After completion of the reaction, water (100 ml) was added, and the mixture was extracted with methylene chloride (50 ml) twice, dried over anhydrous magnesium sulfate and concentrated under reduced pressure. The resulting crude product was purified by silica gel chromatography to give 2-(4-chlorobenzyloxy)-α-(1-imidazolyl)benzaldehyde O-methyloxime (0.01 g) as colorless crystals. mp. 92.5°–93.5° C.

EXAMPLE 9

Synthesis of 2-(4-chlorobenzyloxy)benzaldehyde oxime

Potassium carbonate (33.17 g) and DMF (180 ml) were added to salicylaldehyde (24.42 g), and the mixture was stirred at room temperature for 10 minutes. Then a mixture of 4-chlorobenzyl chloride (33.82 g) and DMF (20 ml) was added at room temperature over 15 minutes, and the mixture was stirred at 60° C. for 3 hours. After completion of the reaction, ether (500 ml) was added, and the mixture was washed with water (400 ml) three times, dried over anhydrous magnesium sulfate and concentrated under reduced pressure to give crude 2-(4-chlorobenzyloxy)benzaldehyde. The ethanol (200 ml) and hydroxylamine hydrochloride (27.80 g) was added to the crude product, and the mixture was stirred at 80° C. overnight. After completion of the reaction, water (400 ml) was added, and the mixture was extracted with methylene chloride (200 ml) three times, dried over anhydrous magnesium sulfate and concentrated under reduced pressure. The resulting crude product was recrystallized from ethyl acetate/n-hexane to give 2-(4-chlorobenzyloxy)benzaldehyde oxime (32.06 g) as colorless crystals. mp. 122.5°–123.5° C.

EXAMPLE 10

Synthesis of 2-(4-chlorobenzyloxy)-α-(1-imidazolyl)benzaldehyde oxime 2-(4-Chlorobenzyloxy)benzaldehyde oxime (26.17 g) was dissolved in ether (200 ml) and methylene chloride (50 ml), and chlorine (6.0 ml) was introduced at −10° C. or below, and then the temperature was raised from −10° C. to room temperature over 2 hours. After completion of the reaction, the mixture was concentrated under reduced pressure to give crude α-chloro-2-(4-chlorobenzyloxy) benzaldehyde oxime. The resulting crude product was dissolved in acetonitrile (150 ml), a mixture of imidazole (17.02 g) and acetonitrile (100 ml) was added at room temperature over 15 minutes, and then the resulting mixture was stirred at 65° to 70° C. for 2 hours. After completion of the reaction, water and methylene chloride were added. The resulting crystals were separated by filtration to give 2-(4-chlorobenzyloxy)-α-(1-imidazolyl)benzaldehyde oxime (11.05 g) as colorless crystals. mp. 196°–197° C.

EXAMPLE 11

Synthesis of 2-(4-chlorobenzyloxy)-α-(1-imidazolyl)benzaldehyde O-benzyloxime

Potassium carbonate (0.21 g), benzyl chloride (0.15 g) and DMF (2 ml) were added to 2-(4-chlorobenzyloxy)-α-(1-imidazolyl)benzaldehyde oxime (0.33 g), and the mixture was stirred at 60° C. for 2 hours. After completion of the reaction, ether (100 ml) was added, and the mixture was extracted with brine (80 ml) twice, dried over anhydrous magnesium sulfate and concentrated under reduced pressure. The resulting crude product was purified by silica gel chromatography to give 2-(4-chlorobenzyloxy)-α-(1-imidazolyl)benzaldehyde O-benzyloxime (0.38 g) as colorless crystals. mp. 94°–95.5° C.

EXAMPLE 12

Synthesis of α-(1-imidazolyl)-2-(1-phenylpropyloxy)benzaldehyde O-methyloxime

Thriphenylphosphine (1.05 g), 1-phenylpropyl alcohol 0.54 g) and THF (20 ml) were added to 2-hydroxy-α-(1-imidazolyl)benzaldehyde O-methyloxime (0.43 g), and diethyl azodicarboxylate (0.70 g) was added under ice-cooling over 10 minutes. then the mixture was stirred at room temperature for 2 hours. After completion of the reaction, ether (100 ml) was added, the mixture was washed with water (80 ml) twice, and the ether layer was concentrated under reduced pressure. the resulting crude product was purified by silica gel chromatography to α-(1-imidazolyl)-2-(1-phenylpropyloxy)benzaldehyde O-methyloxime (0.63 g) as a colorless oil.

EXAMPLE 13

According the same manner as that described above, the compounds in the following tables (Compound Nos. 1 to 1130) were prepared.

The physical properties of the representative compounds obtained are in Tables 1 to 156. In the tables, the physical properties of the compounds obtained in Examples 4, 5, 7 and 8 are also listed. In the tables, Me means methyl, Et means ethyl, n-Pr means n-propyl, i-Pr means isopropyl, i-Bu means isobutyl, t-Bu means t-butyl, Ph means phenyl, and Bn means benzyl.

The $^1$H-NMR values were determined on 270 MHz and are indicated in terms of δ values (ppm) using tetramethylsilane in $CDCl_3$ as the internal standared. The spin coupling constants (J) are indicated in terms of Hz. In the NMR data, s means a singlet, d means a doublet, t means a triplet, q means a quartet, quint means quintet, sext means a sextet, sept means a septet, and m menas a multiplet.

TABLE 1

| No | R¹ | R² | R³ | X | Y | mp(°C.) | ¹H-NMR(CDCl₃) |
|---|---|---|---|---|---|---|---|
| 1 | 2-Me-benzyl | Me | H | O | CH | | 2.18(3H, s), 4.02(3H, s), 4.94(2H, s), 6.94–7.50(10H, m), 7.96(1H, s) |
| 2 | 3-Me-benzyl | Me | H | O | CH | | |
| 3 | 4-Me-benzyl | Me | H | O | CH | 70.5–72 | 2.32(3H, s), 4.02(3H, s), (4.90(2H, s), 6.90–7.51(10H, m), 7.98(1H, s) |
| 4 | 2-F-benzyl | Me | H | O | CH | | |

TABLE 1-continued
| No | R¹ | R² | R³ | X | Y | mp(°C.) | ¹H-NMR(CDCl₃) |
|---|---|---|---|---|---|---|---|
| 5 | 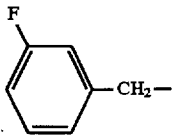 (F, CH₂—) | Me | H | O | CH | | |
| 6 | 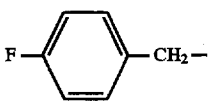 (F, CH₂—) | Me | H | O | CH | | |
| 7 | 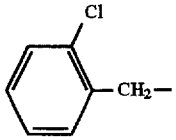 (Cl, CH₂—) | Me | H | O | CH | 91.5–92.5 | 4.05(3H, s), 5.07(2H, s), 6.89–7.54 (10H, m), 8.04(1H, s) |
TABLE 2
| No | R¹ | R² | R³ | X | Y | mp(°C.) | ¹H-NMR(CDCl₃) |
|---|---|---|---|---|---|---|---|
| 8 | 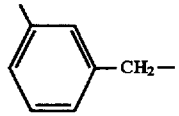 (Cl, CH₂—) | Me | H | O | CH | | |
| 9 | 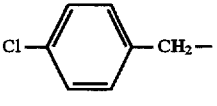 (Cl, CH₂—) | Me | H | O | CH | 92.5–93.5 | 4.03(3H, s), 4.90(2H, s), 6.93–7.54(10H, m), 7.96(1H, s) |
| 10 | 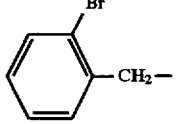 (Br, CH₂—) | Me | H | O | CH | | |
| 11 | 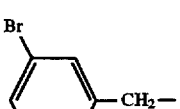 (Br, CH₂—) | Me | H | O | CH | | |
| 12 | 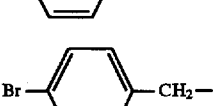 (Br, CH₂—) | Me | H | O | CH | | |
| 13 | 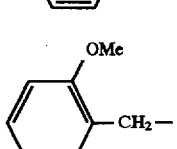 (OMe, CH₂—) | Me | H | O | CH | | |
| 14 | 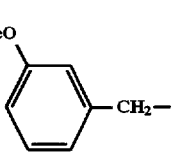 (MeO, CH₂—) | Me | H | O | CH | | |

TABLE 2-continued
| No | R¹ | R² | R³ | X | Y | mp(°C.) | ¹H-NMR(CDCl₃) |
|---|---|---|---|---|---|---|---|
| 15 |  | Me | H | O | CH | | 3.79(3H, s), 4.02((3H, s), 4.87(2H, s), 6.80–7.51(10H, m), 7.97(1H, s) |
TABLE 3
| No | R¹ | R² | R³ | X | Y | mp(°C.) | ¹H-NMR(CDCl₃) |
|---|---|---|---|---|---|---|---|
| 16 | 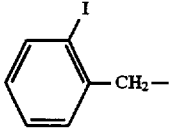 | Me | H | O | CH | | |
| 17 | 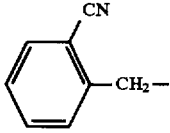 | Me | H | O | CH | | |
| 18 | 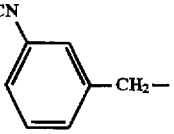 | Me | H | O | CH | | |
| 19 | 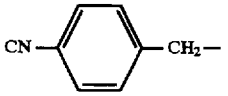 | Me | H | O | CH | | |
| 20 | 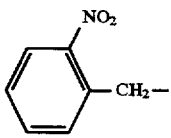 | Me | H | O | CH | | |
| 21 | 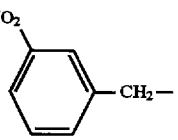 | Me | H | O | CH | | |
| 22 | 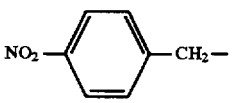 | Me | H | O | CH | | |
TABLE 4
| No | R¹ | R² | R³ | X | Y | mp(°C.) | ¹H-NMR(CDCl₃) |
|---|---|---|---|---|---|---|---|
| 23 | 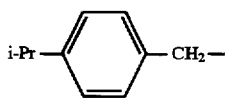 | Me | H | O | CH | | |

TABLE 4-continued
| No | R¹ | R² | R³ | X | Y | mp(°C.) | ¹H-NMR(CDCl₃) |
|----|----|----|----|---|---|---------|---------------|
| 24 | 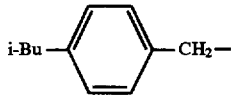 i-Bu—⟨⟩—CH₂— | Me | H | O | CH | | |
| 25 | 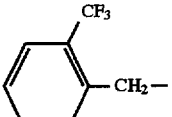 2-CF₃-C₆H₄-CH₂— | Me | H | O | CH | | |
| 26 | 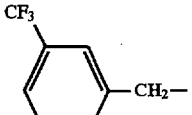 3-CF₃-C₆H₄-CH₂— | Me | H | O | CH | | 4.04(3H, s), 4.99(2H, s), 6.97–7.55(10H, m), 7.93(1H, s) |
| 27 | 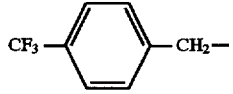 4-CF₃-C₆H₄-CH₂— | Me | H | O | CH | | |
| 28 | 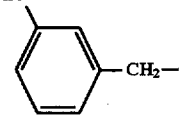 3-PhO-C₆H₄-CH₂— | Me | H | O | CH | | |
| 29 | 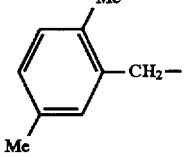 2,5-diMe-C₆H₃-CH₂— | Me | H | O | CH | | |
| 30 | 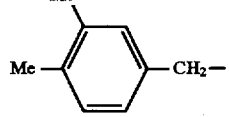 2,4-diMe-C₆H₃-CH₂— | Me | H | O | CH | | |
TABLE 5
| No | R¹ | R² | R³ | X | Y | mp(°C.) | ¹H-NMR(CDCl₃) |
|----|----|----|----|---|---|---------|---------------|
| 31 | 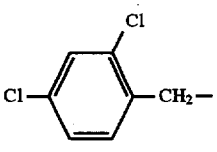 2,4-diCl-C₆H₃-CH₂— | Me | H | O | CH | 122–123 | 4.05(3H, s), 5.01(2H, s), 6.79–7.55(9H, m), 8.01(1H, s) |
| 32 | 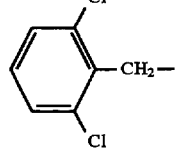 2,6-diCl-C₆H₃-CH₂— | Me | H | O | CH | 110.5–111.5 | 3.98(3H, s), 5.19(2H, s), 6.82(1H, s), 7.02–7.30(6H, m), 7.47–7.60(2H, m), 7.84(1H, s) |

TABLE 5-continued
| No | R¹ | R² | R³ | X | Y | mp(°C.) | ¹H-NMR(CDCl₃) |
|---|---|---|---|---|---|---|---|
| 33 | 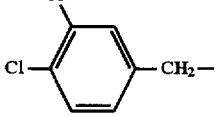 3,4-dichlorobenzyl | Me | H | O | CH | | |
| 34 | 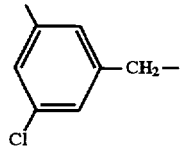 3,5-dichlorobenzyl | Me | H | O | CH | | |
| 35 | 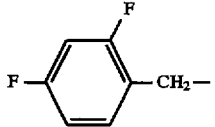 2,4-difluorobenzyl | Me | H | O | CH | | 4.03(3H, s), 4.96(2H, s), 6.74–6.88(3H, m), 7.00–7.20(4H, m), 7.45–7.54(2H, m), 7.95(1H, s) |
| 36 | 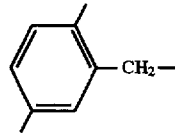 2,5-difluorobenzyl | Me | H | O | CH | | |
| 37 | 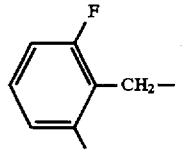 2,6-difluorobenzyl | Me | H | O | CH | | |
TABLE 6
| No | R¹ | R² | R³ | X | Y | mp(°C.) | ¹H-NMR(CDCl₃) |
|---|---|---|---|---|---|---|---|
| 38 | 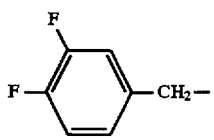 3,4-difluorobenzyl | Me | H | O | CH | | |
| 39 | 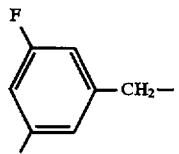 3,5-difluorobenzyl | Me | H | O | CH | | |
| 40 | 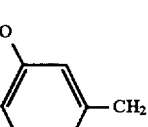 3-BnO-benzyl | Me | H | O | CH | | |

TABLE 6-continued

| No | R¹ | R² | R³ | X | Y | mp(°C.) | ¹H-NMR(CDCl₃) |
|---|---|---|---|---|---|---|---|
| 41 | BnO-C₆H₄-CH₂- (4-BnO-benzyl) | Me | H | O | CH | | |
| 42 | 2,3-(MeO)₂-C₆H₃-CH₂- | Me | H | O | CH | | |
| 43 | 2,4-(MeO)₂-C₆H₃-CH₂- | Me | H | O | CH | | |
| 44 | 2,5-(MeO)₂-C₆H₃-CH₂- | Me | H | O | CH | | |
| 45 | 3,4-(MeO)₂-C₆H₃-CH₂- | Me | H | O | CH | | |

TABLE 7

| No | R¹ | R² | R³ | X | Y | mp(°C.) | ¹H-NMR(CDCl₃) |
|---|---|---|---|---|---|---|---|
| 46 | 3,5-(MeO)₂-C₆H₃-CH₂- | Me | H | O | CH | | |
| 47 | 4-MeS-C₆H₄-CH₂- | Me | H | O | CH | | |
| 48 | 4-CF₃O-C₆H₄-CH₂- | Me | H | O | CH | | |
| 49 | 2,4,6-Me₃-C₆H₂-CH₂- | Me | H | O | CH | 118–119 | 2.13(6H, s), 2.25(3H, s), 3.96(3H, s), 4.91(2H, s), 6.81(2H, s), 6.88(1H, s), 7.04–7.14(2H, m), 7.43–7.54(2H, m), 7.82(1H, s) |
| 50 | 4-MeSO₂-C₆H₄-CH₂- | Me | H | O | CH | | |

TABLE 7-continued

| No | R¹ | R² | R³ | X | Y | mp(°C.) | ¹H-NMR(CDCl₃) |
|---|---|---|---|---|---|---|---|
| 51 | biphenyl-CH₂— | Me | H | O | CH | 128–129 | 4.03(3H, s), 4.99(2H, s), 7.00–7.10(5H, m), 7.24–7.59(10H, m), 8.01(1H, s) |
| 52 | PhOCH₂CH₂— | Me | H | O | CH |  | 3.94(2H, t, J=4.3), 4.02(3H, s), 4.17 (2H, t, J=4.3), 6.82–7.54(11H, m), 7.88(1H, s) |

TABLE 8

| No | R¹ | R² | R³ | X | Y | mp(°C.) | ¹H-NMR(CDCl₃) |
|---|---|---|---|---|---|---|---|
| 53 | MeOCOCH₂— | Me | H | O | CH |  | 3.72(3H, s), 4.05(3H, s), 4.50(2H, s), 6.78–7.53(6H, m), 8.03(1H, s) |
| 54 | PhCOCH₂— | Me | H | O | CH |  | 4.04(3H, s), 5.15(2H, s), 6.79–7.86(11H, m), 8.04(1H, s) |
| 55 | 4-Cl-C₆H₄-CH₂— | Me | H | S | CH |  | 3.95(2H, s), 4.05(3H, s), 7.03–7.43(10H, m), 7.97(1H, s) |
| 56 | C₆H₅— | Me | H | S | CH |  |  |
| 57 | 4-Me-C₆H₄-CH₂— | Me | H | S | CH |  |  |
| 58 | C₆H₅-CH₂— | Me | H | S | CH | 74.5–75.5 |  |
| 59 | 4-Cl-C₆H₄— | Me | H | S | CH |  |  |
| 60 | 3-Cl-4-CF₃-C₆H₃— | Me | H | S | CH |  |  |

TABLE 9

| No | R¹ | R² | R³ | X | Y | mp(°C.) | ¹H-NMR(CDCl₃) |
|---|---|---|---|---|---|---|---|
| 61 | 4-NO₂-C₆H₄— | Me | H | S | CH |  |  |
| 62 | 5-Cl-thiophen-2-yl-CH₂— | Me | H | O | N | 91.5–92.5 |  |

TABLE 9-continued

| No | R¹ | R² | R³ | X | Y | mp(°C.) | ¹H-NMR(CDCl₃) |
|---|---|---|---|---|---|---|---|
| 63 | 4-CF₃-pyridin-2-yl | Me | H | O | N | 124–125 | |
| 64 | 3-Me-isoxazol-5-yl-CH₂– | Me | H | O | N | | |
| 65 | 4-Cl-C₆H₄-CH₂– | Me | H | O | N | | 4.09(3H, s), 4.89(2H, s), 6.93–7.57(8H, m), 7.91(1H, s), 9.05(1H, s) |
| 66 | 2,4-diCl-C₆H₃-CH₂– | Me | H | O | N | 130–131 | 4.11(3H, s), 5.00(2H, s), 6.87(1H, d, J=8.5), 6.94(1H, d, J=8.5), 7.08–7.57(5H, m), 7.89(1H, s), 9.10(1H, s) |
| 67 | thiophen-2-yl-CH₂– | Me | H | O | CH | | |
| 68 | 5-Cl-thiophen-2-yl-CH₂– | Me | H | O | CH | | 4.04(3H, s), 4.99(2H, s), 6.63(1H, d, J=3.7), 6.74(1H, d, J=3.7), 6.98–7.51(6H, m), 7.96(1H, s) |

TABLE 10

| No | R¹ | R² | R³ | X | Y | mp(°C.) | ¹H-NMR(CDCl₃) |
|---|---|---|---|---|---|---|---|
| 69 | isoxazol-5-yl-CH₂– | Me | H | O | CH | | |
| 70 | 3-Me-isoxazol-5-yl-CH₂– | Me | H | O | CH | 75.5–76.5 | 2.38(3H, s), 4.05(3H, s), 4.98(2H, s), 5.58(1H, s), 7.02–7.53(6H, m), 7.99(1H, s) |
| 71 | 3-Ph-isoxazol-5-yl-CH₂– | Me | H | O | CH | 147–148 | 4.05(3H, s), 5.06(2H, s), 6.03(1H, s)7.05–7.80(11H, m), 8.05(1H, s) |
| 72 | 3-i-Bu-isoxazol-5-yl-CH₂– | Me | H | O | CH | 76–77 | 0.95(6H, d, J=6.7), 2.04(1H, sept, J=6.7), 2.58(2H, d, J=6.7), 4.04(3H, s), 4.99(2H, s), 5.57(1H, s), 7.05–7.54(6H, m), 7.98(1H, s). |
| 73 | 3-t-Bu-isoxazol-5-yl-CH₂– | Me | H | O | CH | | |
| 74 | 3-Ph-isoxazol-5-yl | Me | H | O | CH | | |
| 75 | 3-CF₃-isoxazol-5-yl | Me | H | O | CH | | |

TABLE 11
| No | R¹ | R² | R³ | X | Y | mp(°C.) | ¹H-NMR(CDCl₃) |
|---|---|---|---|---|---|---|---|
| 76 | 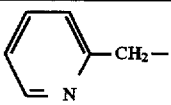 | Me | H | O | CH | 42–49 | 4.06(3H, s), 5.09(2H, s), 6.83(1H, d, J=7.9), 6.99–7.65(8H, m), 8.08(1H, s), 8.51(1H, d, J=4.3) |
| 77 | 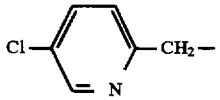 | Me | H | O | CH | | |
| 78 | 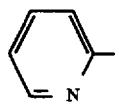 | Me | H | O | CH | | |
| 79 | 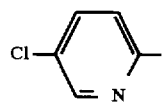 | Me | H | O | CH | 80–81 | 3.93(3H, s), 6.67(1H, d, J=8.6), 6.93(1H, s), 7.10(1H, s), 7.22–7.34(2H, m), 7.50–7.57 (3H, m), 7.90(1H, s), 7.98(1H, d, J=2.4) |
| 80 | 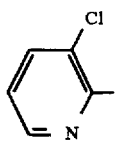 | Me | H | O | CH | | |
| 81 | 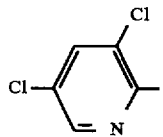 | Me | H | O | CH | | 3.92(3H, s), 6.93(1H, s), 7.09(1H, s), 7.25–7.59(4H, m), 7.67(1H, d, J=2.4), 7.84(1H, d, J=2.4), 7.88(1H, s) |
| 82 | 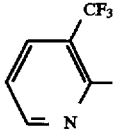 | Me | H | O | CH | | 3.82(3H, s), 6.89(1H, s), 7.03(1H, dd, J=6.7, 4.9), 7.15(1H, s), 7.26–7.60(4H, m), 7.90(1H, d, J=4.9), 7.91 (1H, s), 8.15(1H, dd, J=4.9, 1.2) |
TABLE 12
| No | R¹ | R² | R³ | X | Y | mp(°C.) | ¹H-NMR(CDCl₃) |
|---|---|---|---|---|---|---|---|
| 83 | 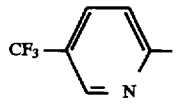 | Me | H | O | CH | 94.5–95.5 | 3.90(3H, s), 6.80(1H, d, J=8.5), 6.91(1H, s), 7.08(1H, s), 7.25–7.61(4H, m), 7.82(1H, dd, J=8.5, 2.5), 7.89(1H, s), 8.31(1H, d, J=1.8) |
| 84 | 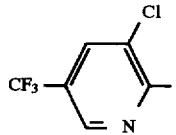 | Me | H | O | CH | | |
| 85 | 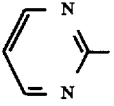 | Me | H | O | CH | | |

TABLE 12-continued

| No | R¹ | R² | R³ | X | Y | mp(°C.) | ¹H-NMR(CDCl₃) |
|----|----|----|----|---|---|---------|---------------|
| 86 | 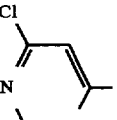 Cl-pyrimidinyl | Me | H | O | CH | | 3.89(3H, s), 6.78(1H, s), 6.98(1H, s), 7.11(1H, s), 7.24–7.63(4H, m), 7.87(1H, s), 8.47(1H, s) |
| 87 | benzoxazol-2-yl | Me | H | O | CH | | 3.87(3H, s), 6.97(1H, s), 7.12(1H, s), 7.21–7.64(8H, m), 7.98(1H, s) |
| 88 | Cl-benzoxazol-2-yl | Me | H | O | CH | | |
| 89 | benzothiazol-2-yl | Me | H | O | CH | | 3.93(3H, s), 6.97(1H, s), 7.17(1H, s), 7.22–7.66(8H, m), 7.99(1H, s) |
| 90 | Cl-benzothiazol-2-yl | Me | H | O | CH | | |

TABLE 13

| No | R¹ | R² | R³ | X | Y | mp(°C.) | ¹H-NMR(CDCl₃) |
|----|----|----|----|---|---|---------|---------------|
| 91 | 1,3-dioxolan-2-yl-CH₂– | Me | H | O | CH | | |
| 92 | thiazol-2-yl | Me | H | O | CH | | 3.98(3H, s), 6.77(1H, d, J=3.7), 6.98(1H, s), 7.10–7.13(2H, m), 7.31–7.68(4H, m), 7.97(1H, s) |
| 93 | Me-1,3,4-thiadiazol-2-yl | Me | H | O | CH | | |
| 94 | t-Bu-1,3,4-thiadiazol-2-yl | Me | H | O | CH | | |
| 95 | CF₃-1,3,4-thiadiazol-2-yl | Me | H | O | CH | | |
| 96 | quinolin-2-yl | Me | H | O | CH | | 3.86(3H, s), 6.86(1H, s), 6.86(1H, d, J=8.5), 7.14(1H, d, J=1.2), 7.30–7.73(8H, m), 7.92(1H, s), 8.03(1H, d, J=8.5) |
| 97 | quinoxalin-2-yl | Me | H | O | CH | | |

TABLE 14

| No | R¹ | R² | R³ | X | Y | mp(°C.) | ¹H-NMR(CDCl₃) |
|---|---|---|---|---|---|---|---|
| 98 | 4-Cl, 6-Me, 2-Me pyrimidinyl | Me | H | O | CH | | 2.58(3H, s), 3.88(3H, s), 6.94(1H, s), 7.08(1H, s), 7.28–7.62(4H, m), 7.88(1H, s), 8.37(1H, s) |
| 99 | 4-Cl, 6-Me, 2-Et pyrimidinyl | Me | H | O | CH | | |
| 100 | 5-Cl, 3-CF₃, 2-pyridyl | Me | H | O | CH | | |

TABLE 15

| No | R¹ | R² | R³ | X | Y | mp(°C.) | ¹H-NMR(CDCl₃) |
|---|---|---|---|---|---|---|---|
| 101 | 2-Me-benzyl | Et | H | O | CH | | 1.34(3H, t, J=7.3), 2.18(3H, s), 4.27(2H, q, J=7.3), 4.95(2H, s), 6.97–7.49(10H, m), 8.04(1H, s) |
| 102 | 3-Me-benzyl | Et | H | O | CH | | |
| 103 | 4-Me-benzyl | Et | H | O | CH | 80–82 | 1.33(3H, t, J=7.3), 2.32(3H, s), 4.27(2H, q, J=7.3), 4.90(2H, s), 6.91–7.50(10H, m), 8.04(1H, s) |
| 104 | 2-F-benzyl | Et | H | O | CH | | 1.36(3H, t, J=7.3), 4.29(2H, q, J=7.3), 5.03(2H, s), 6.89–7.52(10H, m), 8.04(1H, s) |
| 105 | 3-F-benzyl | Et | H | O | CH | | |
| 106 | 4-F-benzyl | Et | H | O | CH | 77–79 | 1.35(3H, t, J=7.3), 4.28(2H, q, J=7.3), 4.89(2H, s), 6.94–7.52(10H, m), 8.00(1H, s) |

TABLE 15-continued

| No | R¹ | R² | R³ | X | Y | mp(°C.) | ¹H-NMR(CDCl₃) |
|----|----|----|----|---|---|---------|----------------|
| 107 | 2-Cl-C₆H₄-CH₂- | Et | H | O | CH | 67-70 | 1.37(3H, t, J=7.3), 4.30(2H, q, J=7.3), 5.07(2H, s), 6.90-7.53(10H, m), 8.09(1H, s) |

TABLE 16

| No | R¹ | R² | R³ | X | Y | mp(°C.) | ¹H-NMR(CDCl₃) |
|----|----|----|----|---|---|---------|----------------|
| 108 | 3-Cl-C₆H₄-CH₂- | Et | H | O | CH | 73.5-75 | 1.37(3H, t, J=7.3), 4.31(2H, q, J=7.3), 4.91(2H, s), 6.90-7.54(10H, m), 8.09(1H, s) |
| 109 | 4-Cl-C₆H₄-CH₂- | Et | H | O | CH | 99.5-100.5 | 1.37(3H, t, J=7.3), 4.30(2H, q, J=7.3), 5.03(2H, s), 6.77-7.53(10H, m), 8.09(1H, s) |
| 110 | 2-Br-C₆H₄-CH₂- | Et | H | O | CH | | 1.37(3H, t, J=7.3), 4.30(2H, q, J=7.3), 5.03(2H, s), 6.77-7.53(10H, m), 8.09(1H, s) |
| 111 | 3-Br-C₆H₄-CH₂- | Et | H | O | CH | | |
| 112 | 4-Br-C₆H₄-CH₂- | Et | H | O | CH | | |
| 113 | 2-OMe-C₆H₄-CH₂- | Et | H | O | CH | | |
| 114 | 3-MeO-C₆H₄-CH₂- | Et | H | O | CH | | |
| 115 | 4-MeO-C₆H₄-CH₂- | Et | H | O | CH | | 1.35(3H, t, J=7.3), 3.79(3H, s), 4.27(2H, q, J=7.3), 4.87(2H, s), 6.80-7.51(10H, m), 8.02(1H, s) |

TABLE 17

| No | R¹ | R² | R³ | X | Y | mp(°C.) | ¹H-NMR(CDCl₃) |
|---|---|---|---|---|---|---|---|
| 116 | 2-I-C₆H₄-CH₂- | Et | H | O | CH | | |
| 117 | 2-CN-C₆H₄-CH₂- | Et | H | O | CH | | |
| 118 | 3-CN-C₆H₄-CH₂- | Et | H | O | CH | | 1.37(3H, t, J=7.3), 4.30(2H, q, J=7.3), 4.96(2H, s), 6.98–7.58(10H, m), 7.94(1H, s) |
| 119 | 4-CN-C₆H₄-CH₂- | Et | H | O | CH | | |
| 120 | 2-NO₂-C₆H₄-CH₂- | Et | H | O | CH | 104.5–106.5 | 1.39(3H, t, J=7.3), 4.32(2H, q, J=7.3), 5.39(2H, s), 7.01–8.16(11H, m), |
| 121 | 3-NO₂-C₆H₄-CH₂- | Et | H | O | CH | | |
| 122 | 4-NO₂-C₆H₄-CH₂- | Et | H | O | CH | | |

TABLE 18

| No | R¹ | R² | R³ | X | Y | mp(°C.) | ¹H-NMR(CDCl₃) |
|---|---|---|---|---|---|---|---|
| 123 | 4-i-Pr-C₆H₄-CH₂- | Et | H | O | CH | | |
| 124 | 4-i-Bu-C₆H₄-CH₂- | Et | H | O | CH | | 1.30(9H, s), 1.36(3H, t, J=7.3), 4.28(2H, q, J=7.3), 4.92(2H, s), 6.74–7.51(10H, m), 8.08(1H, s) |
| 125 | 2-CF₃-C₆H₄-CH₂- | Et | H | O | CH | | |

TABLE 18-continued
| No | R¹ | R² | R³ | X | Y | mp(°C.) | ¹H-NMR(CDCl₃) |
|---|---|---|---|---|---|---|---|
| 126 | 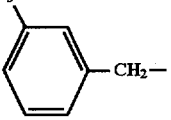 | Et | H | O | CH | | 1.36(3H, t, J=7.3), 4.29(2H, q, J=7.3), 4.99(2H, s), 6.96–7.54(10H, m), 7.98(1H, s) |
| 127 | 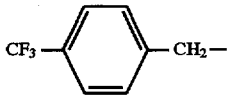 | Et | H | O | CH | 88.0–89.5 | |
| 128 | 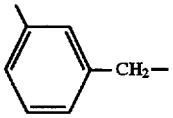 | Et | H | O | CH | | 1.35(3H, t, J=7.3), 4.27(2H, q, J=7.3), 4.93(2H, s), 6.76–7.50(10H, m), 7.98(1H, s) |
| 129 | 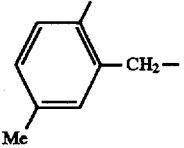 | Et | H | O | CH | 72–73.5 | 1.35(3H, t, J=7.3), 2.14(3H, s), 2.28(3H, s), 4.27(2H, q, J=7.3), 4.91(2H, s), 6.79(1H, s), 7.00–7.50(8H, m), 8.03(1H, s) |
| 130 | 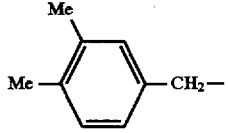 | Et | H | O | CH | | |
TABLE 19
| No | R¹ | R² | R³ | X | Y | mp(°C.) | ¹H-NMR(CDCl₃) |
|---|---|---|---|---|---|---|---|
| 131 | 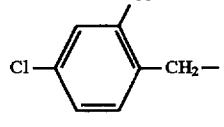 | Et | H | O | CH | 106.5–107.5 | 1.38(3H, t, J=7.3), 4.30(2H, q, J=7.3), 5.01(2H, s), 6.79–7.55(9H, m), 8.07(1H, s) |
| 132 | 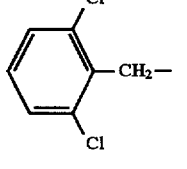 | Et | H | O | CH | 97–98 | 1.30(3H, t, J=7.3), 4.23(2H, q, J=7.3), 5.19(2H, s), 6.83(1H, s), 7.03–7.54(8H, m), 7.90(1H, s) |
| 133 | 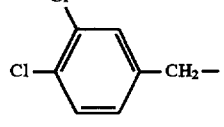 | Et | H | O | CH | 113–114 | 1.37(3H, t, J=7.3), 4.29(2H, q, J=7.3), 4.88(2H, s), 6.83–7.54(9H, m), 7.98(1H, s) |
| 134 | 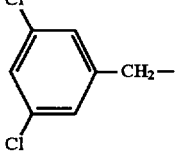 | Et | H | O | CH | | |

TABLE 19-continued
| No | R¹ | R² | R³ | X | Y | mp(°C.) | ¹H-NMR(CDCl₃) |
|---|---|---|---|---|---|---|---|
| 135 | 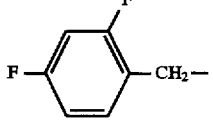 | Et | H | O | CH | | |
| 136 | 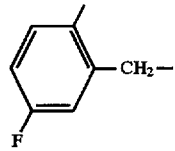 | Et | H | O | CH | | |
| 137 | 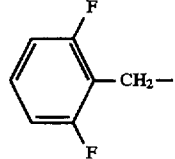 | Et | H | O | CH | | |
TABLE 20
| No | R¹ | R² | R³ | X | Y | mp(°C.) | ¹H-NMR(CDCl₃) |
|---|---|---|---|---|---|---|---|
| 138 | 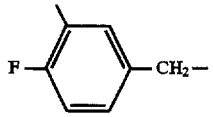 | Et | H | O | CH | | |
| 139 | 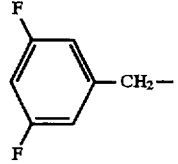 | Et | H | O | CH | | |
| 140 | 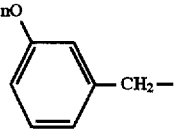 | Et | H | O | CH | | |
| 141 | 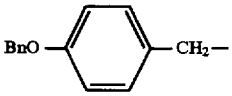 | Et | H | O | CH | | |
| 142 | 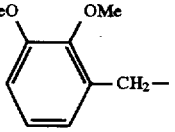 | Et | H | O | CH | | |
| 143 | 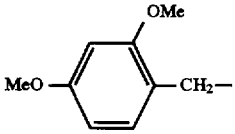 | Et | H | O | CH | | |

TABLE 20-continued
| No | R¹ | R² | R³ | X | Y | mp(°C.) | ¹H-NMR(CDCl₃) |
|---|---|---|---|---|---|---|---|
| 144 | 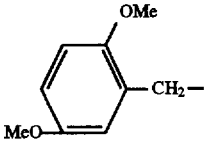 | Et | H | O | CH | | |
| 145 | 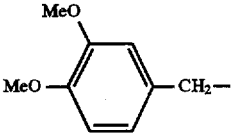 | Et | H | O | CH | | |
TABLE 21
| No | R¹ | R² | R³ | X | Y | mp (°C.) | ¹H-NMR (CDCl₃) |
|---|---|---|---|---|---|---|---|
| 146 | 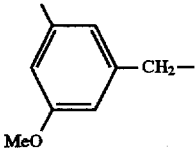 | Et | H | O | CH | | |
| 147 | 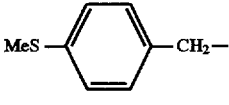 | Et | H | O | CH | | |
| 148 |  | Et | H | O | CH | | |
| 149 | 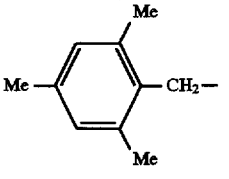 | Et | H | O | CH | 84.5–85.5 | 1.29(3H, t, J=7.3), 2.13(6H, s), 2.25(3H, s), 4.21(2H, q, J=7.3), 4.91(2H, s), 6.80(2H, s), 6.88(1H, s), 7.04–7.53(5H, m), 7.88(1H, s) |
| 150 | 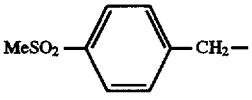 | Et | H | O | CH | | |
| 151 | 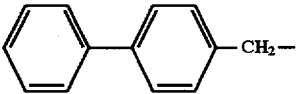 | Et | H | O | CH | | |
| 152 | PhOCH₂CH₂— | Et | H | O | CH | | 1.35(3H, t, J=7.3), 3.95(3H, t, J=5.5), 4.18(2H, t, J=5.5), 4.27(2H, q, J=7.3), 6.82–7.53(11H, m), 7.93(1H, s) |

TABLE 22
| No | R¹ | R² | R³ | X | Y | mp (°C.) | ¹H-NMR (CDCl₃) |
|----|----|----|----|----|----|----|----|
| 153 | 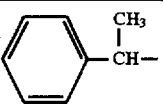 | Et | H | O | CH | | 1.31(3H, d, J=6.1), 1.40(3H, t, J=7.3), 4.32(2H, q, J=7.3), 5.15(1H, q, J=6.1), 6.72(1H, d, J=7.9, 6.93–7.49(10H, m), 8.04(1H, s) |
| 154 | PhCOCH₂— | Et | H | O | CH | | |
| 155 | 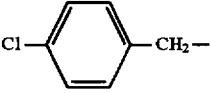 | Et | H | S | CH | 96.5–97.5 | 1.41(3H, t, J=7.3), 3.96(2H, s), 4.30(2H, q, J=7.3), 7.03–7.42(10H, m), 8.02(1H, s) |
| 156 | 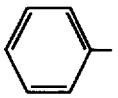 | Et | H | S | CH | | |
| 157 | 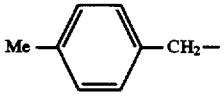 | Et | H | S | CH | | |
| 158 | 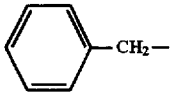 | Et | H | S | CH | | |
| 159 | 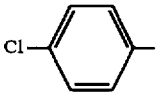 | Et | H | S | CH | | |
| 160 | 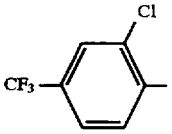 | Et | H | S | CH | | |
TABLE 23
| No | R¹ | R² | R³ | X | Y | mp (°C.) | ¹H-NMR (CDCl₃) |
|----|----|----|----|----|----|----|----|
| 161 | 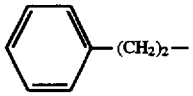 | Et | H | O | CH | | 1.38(3H, t, J=6.7), 2.75(2H, t, J=7.3), 4.03(2H, t, J=7.3), 4.29(2H, q, J=6.7), 6.88(1H, d, J=7.9), 7.00–7.49(10H, m), 8.02(1H, s) |
| 162 | PhO(CH₂)₃— | Et | H | O | CH | | |
| 163 | 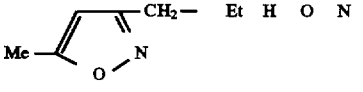 | Et | H | O | N | | |
| 164 | 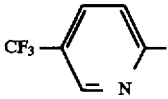 | Et | H | O | N | | |
| 165 | 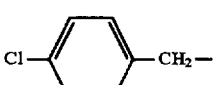 | Et | H | O | N | | 1.38(3H, t, J=6.8), 4.35(2H, q, J=6.8), 4.89(2H, s), 6.92–7.56(8H, m), 7.92(1H, s), 9.11(1H, s) |

TABLE 23-continued
| No | R¹ | R² | R³ | X | Y | mp (°C.) | ¹H-NMR (CDCl₃) |
|---|---|---|---|---|---|---|---|
| 166 | 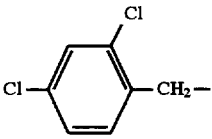 | Et | H | O | N | | |
| 167 | 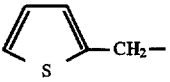 | Et | H | O | CH | | |
| 168 | 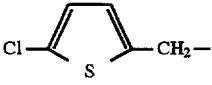 | Et | H | O | CH | | 1.37(3H, t, J=6.7), 4.29(2H, t, J=6.7)), 4.99(2H, s), 6.63(1H, d, J=3.7), 6.74(1H, d, J=3.7), 6.98–7.51(6H, m), |
TABLE 24
| No | R¹ | R² | R³ | X | Y | mp (°C.) | ¹H-NMR (CDCl₃) |
|---|---|---|---|---|---|---|---|
| 169 | 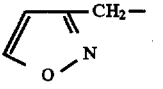 | Et | H | O | CH | | |
| 170 | 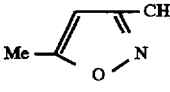 | Et | H | O | CH | 65–66 | 1.38(3H, t, J=7.3), 2.38(3H, s), 4.30(2H, t, J=7.3), 4.98(2H, s), 5.59(1H, s), 7.01–7.53(6H, m), 8.04(1H, s) |
| 171 | 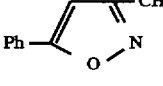 | Et | H | O | CH | 131–132.5 | 1.37(3H, t, J=7.3), 4.30(2H, t, J=7.3), 5.06(2H, s), 6.02(1H, s), 7.05–7.80(11H, m), 8.10(1H, s) |
| 172 | 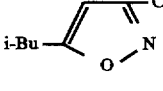 | Et | H | O | CH | 81–82 | 0.95(6H, d, J=6.7), 1.37(3H, t, J=7.3), 2.01(1H, sept, J=6.7), 2.58(2H, d, J=6.7), 4.30(2H, t, 7.3), 4.99(2H, s), 5.57(1H, s), 7.02–7.53(6H, m), 8.03(1H, s). |
| 173 | 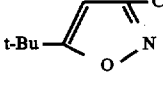 | Et | H | O | CH | | |
| 174 | 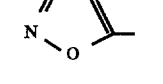 | Et | H | O | CH | | |
| 175 | 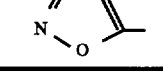 | Et | H | O | CH | | |
TABLE 25
| No | R¹ | R² | R³ | X | Y | mp (°C.) | ¹H-NMR (CDCl₃) |
|---|---|---|---|---|---|---|---|
| 176 | 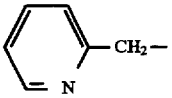 | Et | H | O | CH | | |

TABLE 25-continued
| No | R¹ | R² | R³ | X | Y | mp (°C.) | ¹H-NMR (CDCl₃) |
|---|---|---|---|---|---|---|---|
| 177 | 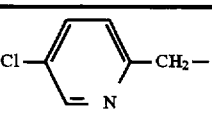 | Et | H | O | CH | | |
| 178 | 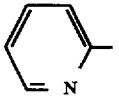 | Et | H | O | CH | | 1.24(3H, t, J=6.7), 4.16(2H, q, J=6.7), 6.68–8.06(11H, m) |
| 179 | 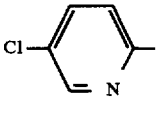 | Et | H | O | CH | | 1.26(3H, t, J=7.3), 4.17(2H, q, J=7.3), 6.65(1H, d, J=7.9), 6.92(1H, s), 7.11(1H, s), 7.21–7.57(5H, m), 7.95(1H, s), 8.00(1H, d, J=2.4) |
| 180 | 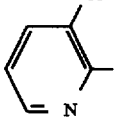 | Et | H | O | CH | | |
| 181 | 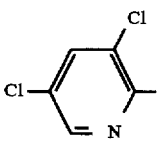 | Et | H | O | CH | | 1.26(3H, t, J=7.3), 4.17(2H, q, J=7.3), 6.93(1H, s), 7.11(1H, s), 7.24–7.59(4H, m), 7.67(1H, d, J=2.4), 7.84(1H, d, J=2.4), 7.93(1H, s) |
| 182 | 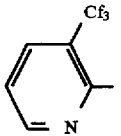 | Et | H | O | CH | | |
TABLE 26
| No | R¹ | R² | R³ | X | Y | mp (°C.) | ¹H-NMR(CDCl₃) |
|---|---|---|---|---|---|---|---|
| 183 | 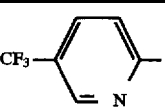 | Et | H | O | CH | | 1.23(3H, t, J=6.7), 4.14(2H, q, J=6.7), 6.78–7.83(8H, m), 7.93(1H, s), 8.32(1H, s) |
| 184 | 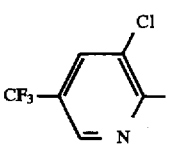 | Et | H | O | CH | | 1.22(3H, t, J=7.3), 4.13(2H, q, J=7.3), 6.92(1H, s), 7.09(1H, s), 7.26–7.91(6H, m), 8.16(1 H, d, J=1.2), |
| 185 | 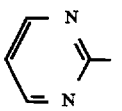 | Et | H | O | CH | | |
| 186 | 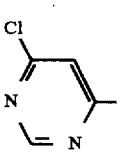 | Et | H | O | CH | 71–73 | 1.24(3H, t, J=7.3), 4.12(2H. q. J=7.3), 6.78(1H, s), 6.98(1H, s), 7.12(1H, s), 7.24–7.62(4H, m), 7.91(1H, s), 8.48(1H, s) |

TABLE 26-continued
| No | R¹ | R² | R³ | X | Y | mp (°C.) | ¹H-NMR(CDCl₃) |
|---|---|---|---|---|---|---|---|
| 187 | 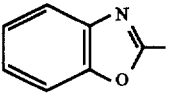 | Et | H | O | CH | | 1.20(3H, t, J=6.7), 4.12(2H. q, J=6.7), 6.97(1H, s), 7.13(1H, s), 7.20–7.66(8, m), 8.02(1H, s) |
| 188 | 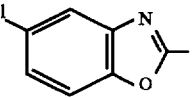 | Et | H | O | CH | | |
| 189 | 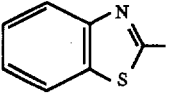 | Et | H | O | CH | | 1.24(3H, t, J=7.3), 4.15(2H. q, J=7.3), 6.97(1H, s), 7.13(1H, s), 7.22–7.65(8H, m), 8.03(1H, s) |
| 190 | 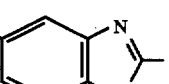 | Et | H | O | CH | | |
TABLE 27
| No | R¹ | R² | R³ | X | Y | mp (°C.) | ¹H-NMR(CDCl₃) |
|---|---|---|---|---|---|---|---|
| 191 | 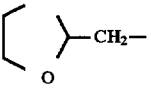 | Et | H | O | CH | 60–62.5 | 1.37(3H, t, J=7.3), 3.84(4H, s), 3.90(2H, d, J=3.7), 4.29(2H. q, J=7.3), 6.93–7.50(6H, m, 8.06(1H, s) |
| 192 | 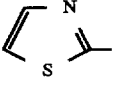 | Et | H | O | CH | | 1.31(3H, t, J=7.3), 4.23(2H, q), J=7.3), 6.76(1H, d, J=3.7), 6.98(1H, s), 7.11–7.59 (6H, m), 8.02(1H, s) |
| 193 | 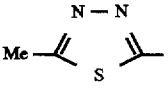 | Et | H | O | CH | | |
| 194 | 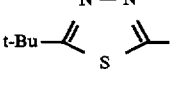 | Et | H | O | CH | | |
| 195 | 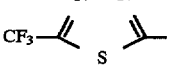 | Et | H | O | CH | | |
| 196 | 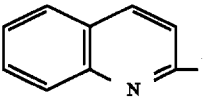 | Et | H | O | CH | | 1.19(3H, t, J=7.3), 4.12(2H. q, J=7.3), 6.85(1H, d, J=6.7), 6.87(1H, s), 7.15(1H, s), 7.30–7.73(8H, m), 7.96(1H, s), 8.03(1H, d, J=8.5) |
| 197 | 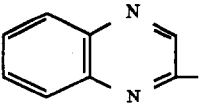 | Et | H | O | CH | | |

TABLE 28
| No | R¹ | R² | R³ | X | Y | mp (°C.) | ¹H-NMR(CDCl₃) |
|---|---|---|---|---|---|---|---|
| 198 | 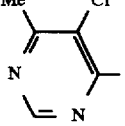 | Et | H | O | CH | | |
| 199 | 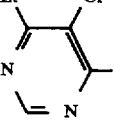 | Et | H | O | CH | | 1.22(3H, t, J=7.3), 1.29(3H, t, J=7.9), 2.92(2H, q, J=7.9), 4.12(2H, q, J=7.3), 6.94(1H, s), 7.09(1H, s), 7.28–7.62(4H, m), 7.92(1H, s), 8.41(1H, s) |
| 200 | 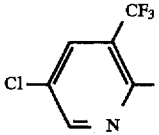 | Et | H | O | CH | | |
TABLE 29
| No | R¹ | R² | R³ | X | Y | mp (°C.) | ¹H-NMR(CDCl₃) |
|---|---|---|---|---|---|---|---|
| 201 | 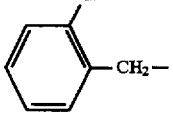 | Allyl | H | O | CH | | |
| 202 | 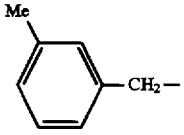 | Allyl | H | O | CH | | |
| 203 | 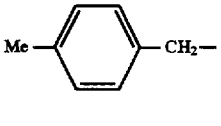 | Allyl | H | O | CH | | 2.32(3H, s), 4.72(2H, dd, J=4.3, 1.2), 4.90 (2H, s), 5.24–5.39(2H, m), 5.97–6.11(1H, m), 6.91–7.50(10H, m), 8.02(1H, s) |
| 204 | 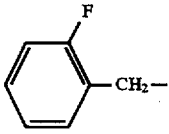 | Allyl | H | O | CH | | |
| 205 | 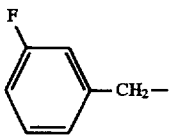 | Allyl | H | O | CH | | |
| 206 | 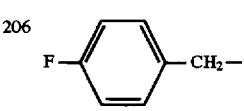 | Allyl | H | O | CH | | |

TABLE 29-continued
| No | R¹ | R² | R³ | X | Y | mp (°C.) | ¹H-NMR(CDCl₃) |
|----|----|----|----|---|---|----------|---------------|
| 207 | 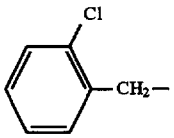 2-Cl-C₆H₄-CH₂- | Allyl | H | O | CH | | 4.73–4.76(2H, m), 5.06(2H, s), 5.25–5.40(2H, m), 5.98–6.12(1H, m), 6.90–7.53 (10H, m), 8.06(1H, m) |
TABLE 30
| No | R¹ | R² | R³ | X | Y | mp (°C.) | ¹H-NMR(CDCl₃) |
|----|----|----|----|---|---|----------|---------------|
| 208 | 2-Cl-C₆H₄-CH₂- | Allyl | H | O | CH | | |
| 209 | 4-Cl-C₆H₄-CH₂- | Allyl | H | O | CH | 68–69 | 4.72(2H, dd, J=7.3, 1.2), 4.90(2H, s), 5.24–5.39(2H, m), 5.97–6.11(1H, s), 6.94–7.52 (10H, m), 7.98(1H, s) |
| 210 | 2-Br-C₆H₄-CH₂- | Allyl | H | O | CH | | |
| 211 | 3-Br-C₆H₄-CH₂- | Allyl | H | O | CH | | |
| 212 | 4-Br-C₆H₄-CH₂- | Allyl | H | O | CH | | |
| 213 | 2-MeO-C₆H₄-CH₂- | Allyl | H | O | CH | | |
| 214 | 3-MeO-C₆H₄-CH₂- | Allyl | H | O | CH | | |
| 215 | 4-MeO-C₆H₄-CH₂- | Allyl | H | O | CH | | |

TABLE 31

| No | R¹ | R² | R³ | X | Y | mp (°C.) | ¹H—NMR (CDCl₃) |
|----|----|----|----|----|----|----|----|
| 216 | 2-I-C₆H₄-CH₂— | Allyl | H | O | CH | | |
| 217 | 2-CN-C₆H₄-CH₂— | Allyl | H | O | CH | | |
| 218 | 3-CN-C₆H₄-CH₂— | Allyl | H | O | CH | | |
| 219 | 4-CN-C₆H₄-CH₂— | Allyl | H | O | CH | | |
| 220 | 2-NO₂-C₆H₄-CH₂— | Allyl | H | O | CH | | |
| 221 | C₆H₅-CH₂— (with NO₂) | Allyl | H | O | CH | | |
| 222 | 4-NO₂-C₆H₄-CH₂— | Allyl | H | O | CH | | |

TABLE 32

| No | R¹ | R² | R³ | X | Y | mp (°C.) | ¹H—NMR (CDCl₃) |
|----|----|----|----|----|----|----|----|
| 223 | 4-i-Pr-C₆H₄-CH₂— | Allyl | H | O | CH | | |
| 224 | 4-t-Bu-C₆H₄-CH₂— | Allyl | H | O | CH | | |
| 225 | 2-CF₃-C₆H₄-CH₂— | Allyl | H | O | CH | | |

TABLE 32-continued

| No | R¹ | R² | R³ | X | Y | mp (°C.) | ¹H—NMR (CDCl₃) |
|---|---|---|---|---|---|---|---|
| 226 | 3-CF₃-C₆H₄-CH₂— | Allyl | H | O | CH | | 4.72–4.98(2H, m), 4.98(2H, s), 5.24–5.39 (2H, m), 5.97–6.12(1H, m), 6.96–7.55(10H, m), 7.96(1H, s) |
| 227 | 4-CF₃-C₆H₄-CH₂— | Allyl | H | O | CH | | |
| 228 | 3-PhO-C₆H₄-CH₂— | Allyl | H | O | CH | | |
| 229 | 2,4-diMe-C₆H₃-CH₂— | Allyl | H | O | CH | | |
| 230 | 2,4-diMe-C₆H₃-CH₂— (2-Me,4-Me) | Allyl | H | O | CH | | |

TABLE 33

| No | R¹ | R² | R³ | X | Y | mp (°C.) | ¹H—NMR(CDCl₃) |
|---|---|---|---|---|---|---|---|
| 231 | 2,4-diCl-C₆H₃-CH₂— | Allyl | H | O | CH | | |
| 232 | 2,6-diCl-C₆H₃-CH₂— | Allyl | H | O | CH | | |
| 233 | 3,4-diCl-C₆H₃-CH₂— | Allyl | H | O | CH | 92.5–93.5 | 4.72–4.75(2H, m), 4.88(2H, s), 5.25–5.40 (2H, m), 5.98–6.12(1H, m), 6.85(1H, dd, J=8.6, 2.4), 6.94(1H, d, J=8.5), 7.06–7.54 (7H, m), 7.96(1H, s) |
| 234 | 3,5-diCl-C₆H₃-CH₂— | Allyl | H | O | CH | | |

TABLE 33-continued
| No | R¹ | R² | R³ | X | Y | mp (°C.) | ¹H—NMR(CDCl₃) |
|---|---|---|---|---|---|---|---|
| 235 | 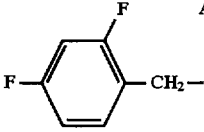 2,4-difluorobenzyl | Allyl | H | O | CH | | |
| 236 | 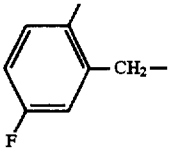 2,5-difluorobenzyl | Allyl | H | O | CH | | |
| 237 | 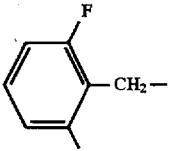 2,6-difluorobenzyl | Allyl | H | O | CH | | |
TABLE 34
| No | R¹ | R² | R³ | X | Y | mp (°C.) | ¹H—NMR(CDCl₃) |
|---|---|---|---|---|---|---|---|
| 238 | 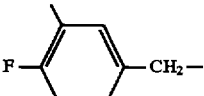 3,4-difluorobenzyl | Allyl | H | O | CH | | |
| 239 | 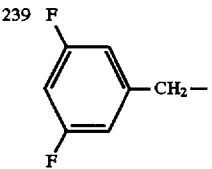 3,5-difluorobenzyl | Allyl | H | O | CH | | |
| 240 | 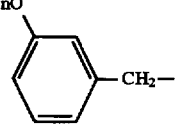 3-BnO-benzyl | Allyl | H | O | CH | | |
| 241 | 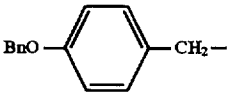 4-BnO-benzyl | Allyl | H | O | CH | | |
| 242 | 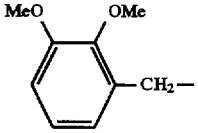 2,3-dimethoxybenzyl | Allyl | H | O | CH | | |
| 243 | 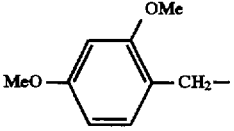 2,4-dimethoxybenzyl | Allyl | H | O | CH | | |

TABLE 34-continued
| No | R¹ | R² | R³ | X | Y | mp (°C.) | ¹H—NMR(CDCl₃) |
|---|---|---|---|---|---|---|---|
| 244 | 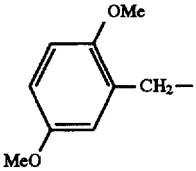 | Allyl | H | O | CH | | |
| 245 | 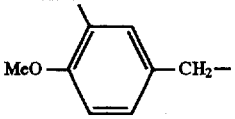 | Allyl | H | O | CH | | |
TABLE 35
| No | R¹ | R² | R³ | X | Y | mp (°C.) | ¹H—NMR(CDCl₃) |
|---|---|---|---|---|---|---|---|
| 246 | 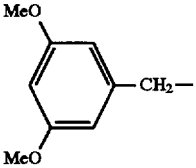 | Allyl | H | O | CH | | |
| 247 | 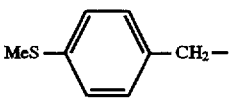 | Allyl | H | O | CH | | |
| 248 | 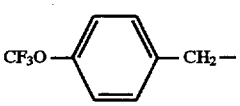 | Allyl | H | O | CH | | |
| 249 | 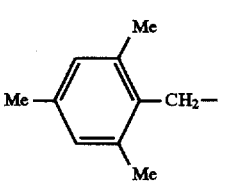 | Allyl | H | O | CH | | |
| 250 | 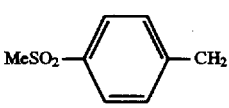 | Allyl | H | O | CH | | |
| 251 | 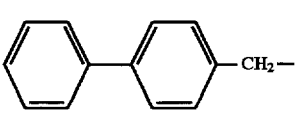 | Allyl | H | O | CH | | |
| 252 | PhOCH₂CH₂— | Allyl | H | O | CH | | |

TABLE 36

| No | R¹ | R² | R³ | X | Y | mp (°C.) | ¹H—NMR(CDCl₃) |
|---|---|---|---|---|---|---|---|
| 253 | Ph-CH(CH₃)- | | Allyl | H | O | CH | 72.5–73.5 | 1.31 (3H, d, J = 6.1), 4.76(2H, dd, J = 4.3, 1.2), 5.15(1H, q, J = 6.1), 5.27–5.42(2H, m), 6.00–6.15(1H, m), 6.71(1H, d, J = 8.6), 6.92–7.48(10H, m), 8.02(1H, s) |
| 254 | PhCOCH₂- | | Allyl | H | O | CH | | |
| 255 | 4-Cl-C₆H₄-CH₂- | | Allyl | H | S | CH | | |
| 256 | C₆H₅- | | Allyl | H | S | CH | | |
| 257 | 4-Me-C₆H₄-CH₂- | | Allyl | H | S | CH | | |
| 258 | C₆H₅-CH₂- | | Allyl | H | S | CH | | |
| 259 | 4-Cl-C₆H₄- | | Allyl | H | S | CH | | |
| 260 | 4-CF₃-2-Cl-C₆H₃- | | Allyl | H | S | CH | | |

TABLE 37

| No | R¹ | R² | R³ | X | Y | mp (°C.) | ¹H—NMR(CDCl₃) |
|---|---|---|---|---|---|---|---|
| 261 | C₆H₅-(CH₂)₂- | | Allyl | H | O | CH | | |
| 262 | PhO(CH₂)₃- | | Allyl | H | O | CH | | |
| 263 | 5-Me-isoxazol-3-yl-CH₂- | | Allyl | H | O | N | | |
| 264 | 4-CF₃-pyridin-2-yl- | | Allyl | H | O | N | | |
| 265 | 4-Cl-C₆H₄-CH₂- | | Allyl | H | O | N | | |

TABLE 37-continued
| No | R¹ | R² | R³ | X | Y | mp (°C.) | ¹H—NMR(CDCl₃) |
|----|----|----|----|---|---|----------|---------------|
| 266 | 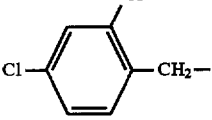 | Allyl | H | O | N | | |
| 267 | 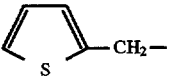 | Allyl | H | O | CH | | |
TABLE 38
| NO | R¹ | R² | R³ | X | Y | mp (°C.) | ¹H—NMR(CDCl₃) |
|----|----|----|----|---|---|----------|---------------|
| 268 | 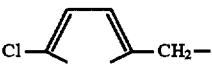 | Allyl | H | O | CH | | |
| 269 | 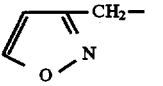 | Allyl | H | O | CH | | |
| 270 | 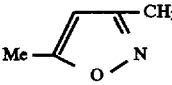 | Allyl | H | O | CH | 57–58 | 2.38(3H, s), 4.74(2H, dd, J = 4.3, 1.2), 4.98 (2H, s), 5.26–5.40(2H, m), 5.59(1H, s), 5.99 –6.13(1H, m), 7.02–7.52(6H, m), 8.02(1H, s) |
| 271 | 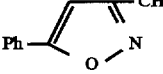 | Allyl | H | O | CH | | |
| 272 | 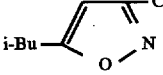 | Allyl | H | O | CH | | |
| 273 | 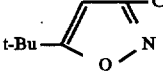 | Allyl | H | O | CH | | |
| 274 | 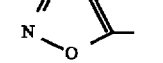 | Allyl | H | O | CH | | |
| 275 | 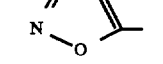 | Allyl | H | O | CH | | |
TABLE 39
| No | R¹ | R² | R³ | X | Y | mp (°C.) | ¹H—NMR(CDCl₃) |
|----|----|----|----|---|---|----------|---------------|
| 276 | 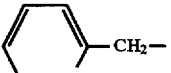 | Allyl | H | O | CH | | |

TABLE 39-continued

| No | R¹ | R² | R³ | X | Y | mp (°C.) | ¹H—NMR(CDCl₃) |
|---|---|---|---|---|---|---|---|
| 277 | 5-Cl-pyridin-2-yl-CH₂— | Allyl | H | O | CH | | |
| 278 | pyridin-2-yl | Allyl | H | O | CH | | |
| 279 | 5-Cl-pyridin-2-yl | Allyl | H | O | CH | | |
| 280 | 3-Cl-pyridin-2-yl | Allyl | H | O | CH | | |
| 281 | 3,5-diCl-pyridin-2-yl | Allyl | H | O | CH | | 4.60–4.62(2H, m), 5.18–5.28(2H, m), 5.85–5.99(1H, m), 6.93(1H, s), 7.12(1H, s), 7.24–7.84(6H, m), 7.92(1H, s) |
| 282 | 3-CF₃-pyridin-2-yl | Allyl | H | O | CH | | |

TABLE 40

| No | R¹ | R² | R³ | X | Y | mp (°C.) | ¹H—NMR(CDCl₃) |
|---|---|---|---|---|---|---|---|
| 283 | 5-CF₃-pyridin-2-yl | Allyl | H | O | CH | | 4.58(2H, dd, J=7.3, 1.2), 5.16–5.25(2H, m), 5.83–5.95(1H, m), 6.79(1H, d, J=9.2), 6.93(1H, s), 7.11(1H, s), 7.24–7.61(4H, m), 7.82(1H, dd, J=8.6, 2.4), 7.92(1H, s), 8.31(1H, d, J=1.8) |
| 284 | 3-Cl-5-CF₃-pyridin-2-yl | Allyl | H | O | CH | | |
| 285 | pyrimidin-2-yl | Allyl | H | O | CH | | |
| 286 | 3-Cl-pyrazin-2-yl | Allyl | H | O | CH | | 4.55–4.58(2H, m), 5.19–5.25(2H, m), 5.81–5.95(1H, m), 6.78(1H, s), 6.99(1H, s), 7.14(1H, s), 7.24–7.62(4H, m), 7.91(1H, s), 8.47(1H, s) |

TABLE 40-continued
| No | R¹ | R² | R³ | X | Y | mp (°C.) | ¹H—NMR(CDCl₃) |
|---|---|---|---|---|---|---|---|
| 287 | 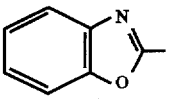 | Allyl | H | O | CH | | |
| 288 | 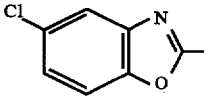 | Allyl | H | O | CH | | |
| 289 | 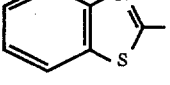 | Allyl | H | O | CH | | |
| 290 | 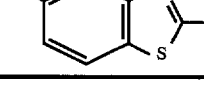 | Allyl | H | O | CH | | |
TABLE 41
| No | R¹ | R² | R³ | X | Y | mp (°C.) | ¹H—NMR(CDCl₃) |
|---|---|---|---|---|---|---|---|
| 291 | 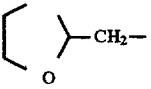 | Allyl | H | O | CH | | |
| 292 | 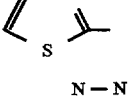 | Allyl | H | O | CH | | |
| 293 | 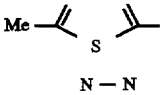 | Allyl | H | O | CH | | |
| 294 | 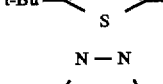 | Allyl | H | O | CH | | |
| 295 | 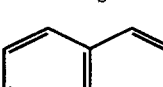 | Allyl | H | O | CH | | |
| 296 | 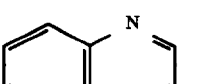 | Allyl | H | O | CH | | |
| 297 |  | Allyl | H | O | CH | | |

TABLE 42

| No | R¹ | R² | R³ | X | Y | mp (°C.) | ¹H—NMR(CDCl₃) |
|---|---|---|---|---|---|---|---|
| 298 | (4-Me, 5-Cl pyrimidinyl) | | Allyl | H | O | CH | | 2.58(3H, s), 4.55–4.58(2H, m), 5.16–5.25 (2H, m), 5.81–5.96(1H, m), 6.95(1H, s), 7.11 (1H, s), 7.27–7.62(4H, m), 7.92(1H, s), 8.37(1H, s) |
| 299 | (4-Et, 5-Cl pyrimidinyl) | | Allyl | H | O | CH | | |
| 300 | (5-Cl, 3-CF₃ pyridinyl) | | Allyl | H | O | CH | | |

TABLE 43

| No | R¹ | R² | R³ | X | Y | mp (°C.) | ¹H—NMR(CDCl₃) |
|---|---|---|---|---|---|---|---|
| 301 | 2-Me-C₆H₄-CH₂— | | i-Bu | H | O | CH | | |
| 302 | 3-Me-C₆H₄-CH₂— | | i-Bu | H | O | CH | | |
| 303 | 4-Me-C₆H₄-CH₂— | | i-Bu | H | O | CH | 84–86 | 0.97(6H, d, J = 6.7), 2.08(1H, sept, J = 6.7), 2.32(3H, s), 4.00(2H, d, J = 6.7), 4.91(2H, s), 6.92–7.50(10H, s), 8.03(1H, s) |
| 304 | 2-F-C₆H₄-CH₂— | | i-Bu | H | O | CH | | |
| 305 | 3-F-C₆H₄-CH₂— | | i-Bu | H | O | CH | | |
| 306 | 4-F-C₆H₄-CH₂— | | i-Bu | H | O | CH | 73–74 | 0.96(6H, d, J = 6.7), 2.08(1H, sept, J = 6.7), 4.01(2H, d, J = 6.7), 4.90(2H, s), 6.96–7.49(10H, m), 7.99(1H, s) |

TABLE 43-continued
| No | R¹ | R² | R³ | X | Y | mp (°C.) | ¹H—NMR(CDCl₃) |
|----|----|----|----|---|---|----------|---------------|
| 307 | 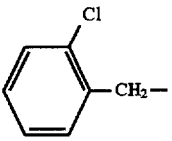 2-Cl-C₆H₄-CH₂- | i-Bu | H | O | CH | | 0.98(6H, d, J = 6.7), 2.10(1H, sept, J = 6.7), 4.03(2H, d, J = 6.7), 5.07(2H, s), 6.92–7.52(10H, m), 8.09(1H, s) |
TABLE 44
| No | R¹ | R² | R³ | X | Y | mp (°C.) | ¹H—NMR(CDCl₃) |
|----|----|----|----|---|---|----------|---------------|
| 308 | 3-Cl-C₆H₄-CH₂- | i-Bu | H | O | CH | | |
| 309 | 4-Cl-C₆H₄-CH₂- | i-Bu | H | O | CH | 84–85 | 0.97(6H, d, J = 6.7), 2.09(1H, sept, J = 6.7), 4.01(2H, d, J = 6.7), 4.90(2H, s), 6.94–7.52(10H, m), 8.01(1H, s) |
| 310 | 2-Br-C₆H₄-CH₂- | i-Bu | H | O | CH | | |
| 311 | 3-Br-C₆H₄-CH₂- | i-Bu | H | O | CH | | |
| 312 | 4-Br-C₆H₄-CH₂- | i-Bu | H | O | CH | | |
| 313 | 2-OMe-C₆H₄-CH₂- | i-Bu | H | O | CH | | |
| 314 | 3-MeO-C₆H₄-CH₂- | i-Bu | H | O | CH | | |
| 315 | 4-MeO-C₆H₄-CH₂- | i-Bu | H | O | CH | | 0.96(6H, d, J = 6.7), 2.08(1H, sept, J = 6.7), 3.79(3H, s), 4.00(2H, d, J = 6.7), 4.87(2H, s), 6.80–7.50(10H, m), 8.02(1H, s) |

TABLE 45

| No | R¹ | R² | R³ | X | Y | mp (°C.) | ¹H—NMR(CDCl₃) |
|---|---|---|---|---|---|---|---|
| 316 | 2-I-C₆H₄-CH₂- | i-Bu | H | O | CH | | |
| 317 | 2-CN-C₆H₄-CH₂- | i-Bu | H | O | CH | | |
| 318 | 3-CN-C₆H₄-CH₂- | i-Bu | H | O | CH | | |
| 319 | 4-CN-C₆H₄-CH₂- | i-Bu | H | O | CH | | |
| 320 | 2-NO₂-C₆H₄-CH₂- | i-Bu | H | O | CH | | |
| 321 | 3-NO₂-C₆H₄-CH₂- | i-Bu | H | O | CH | | |
| 322 | 4-NO₂-C₆H₄-CH₂- | i-Bu | H | O | CH | | |

TABLE 46

| No | R¹ | R² | R³ | X | Y | mp(°C.) | ¹H-NMR(CDCl₃) |
|---|---|---|---|---|---|---|---|
| 323 | 4-i-Pr-C₆H₄-CH₂- | i-Bu | H | O | CH | | |
| 324 | 4-t-Bu-C₆H₄-CH₂- | i-Bu | H | O | CH | | |
| 325 | 2-CF₂-C₆H₄-CH₂- | i-Bu | H | O | CH | | |

TABLE 46-continued
| No | R¹ | R² | R³ | X | Y | mp(°C.) | ¹H-NMR(CDCl₃) |
|---|---|---|---|---|---|---|---|
| 326 | 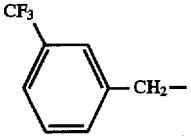 | i-Bu | H | O | CH | 81–82 | 0.97(6H, d, J=6.7), 2.09(1H, sept, J=6.7), 4.02(2H, d, J=6.7), 4.99(2H, s), 6.96–7.55(10H, m), 7.98(1H, s) |
| 327 | 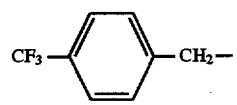 | i-Bu | H | O | CH | | |
| 328 | 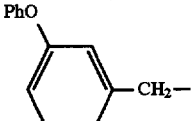 | i-Bu | H | O | CH | | |
| 329 | 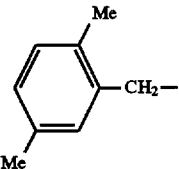 | i-Bu | H | O | CH | | |
| 330 | 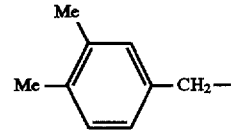 | i-Bu | H | O | CH | | |
TABLE 47
| No | R¹ | R² | R³ | X | Y | mp(°C.) | ¹H-NMR(CDCl₃) |
|---|---|---|---|---|---|---|---|
| 331 | 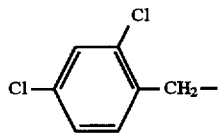 | i-Bu | H | O | CH | | |
| 332 | 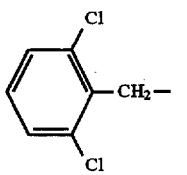 | i-Bu | H | O | CH | | |
| 333 | 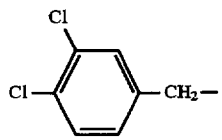 | i-Bu | H | O | CH | 95.5–96.5 | 0.98(6H, d, J=6.7), 2.09(1H, sept, J=6.7), 4.02(2H, d, J=6.7), 4.88(2H, s), 6.83–7.53 (9H, m), 7.98(1H, s) |
| 334 | 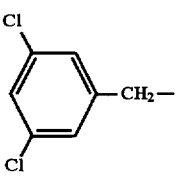 | i-Bu | H | O | CH | | |

TABLE 47-continued
| No | R¹ | R² | R³ | X | Y | mp(°C.) | ¹H-NMR(CDCl₃) |
|---|---|---|---|---|---|---|---|
| 335 | 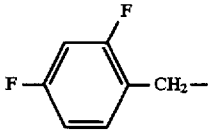 2,4-difluorobenzyl | i-Bu | H | O | CH | | |
| 336 | 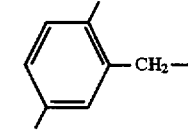 2,5-difluorobenzyl | i-Bu | H | O | CH | | |
| 337 |  2,6-difluorobenzyl | i-Bu | H | O | CH | | |
TABLE 48
| No | R¹ | R² | R³ | X | Y | mp(°C.) | ¹H-NMR(CDCl₃) |
|---|---|---|---|---|---|---|---|
| 338 | 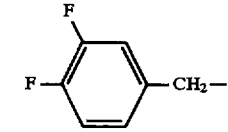 3,4-difluorobenzyl | i-Bu | H | O | CH | | |
| 339 | 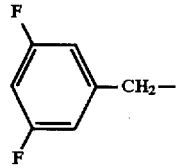 3,5-difluorobenzyl | i-Bu | H | O | CH | | |
| 340 | 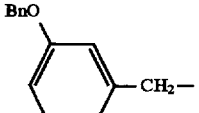 3-BnO-benzyl | i-Bu | H | O | CH | | |
| 341 |  4-BnO-benzyl | i-Bu | H | O | CH | | |
| 342 | 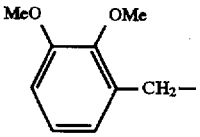 2,3-dimethoxybenzyl | i-Bu | H | O | CH | | |
| 343 | 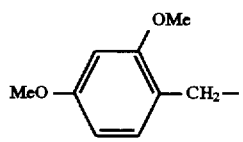 2,4-dimethoxybenzyl | i-Bu | H | O | CH | | |

TABLE 48-continued

| No | R¹ | R² | R³ | X | Y | mp(°C.) | ¹H-NMR(CDCl₃) |
|---|---|---|---|---|---|---|---|
| 344 | 4-OMe, 2-(MeO)-benzyl (OMe at 4, MeO at 2-position, CH₂—) | i-Bu | H | O | CH | | |
| 345 | 3,4-(MeO)₂-benzyl-CH₂— | i-Bu | H | O | CH | | |

TABLE 49

| No | R¹ | R² | R³ | X | Y | mp(°C.) | ¹H-NMR(CDCl₃) |
|---|---|---|---|---|---|---|---|
| 346 | 3,5-(MeO)₂-benzyl-CH₂— | i-Bu | H | O | CH | | |
| 347 | 4-(MeS)-benzyl-CH₂— | i-Bu | H | O | CH | | |
| 348 | 4-(CF₃O)-benzyl-CH₂— | i-Bu | H | O | CH | | |
| 349 | 2,4,6-Me₃-benzyl-CH₂— | i-Bu | H | O | CH | | |
| 350 | 4-(MeSO₂)-benzyl-CH₂— | i-Bu | H | O | CH | | |
| 351 | 4-Ph-benzyl-CH₂— | i-Bu | H | O | CH | | |
| 352 | PhOCH₂CH₂— | i-Bu | H | O | CH | | |

TABLE 50

| No | R¹ | R² | R³ | X | Y | mp(°C.) | ¹H-NMR(CDCl₃) |
|---|---|---|---|---|---|---|---|
| 353 | PhCH(CH₃)— | i-Bu | H | O | CH | | |
| 354 | PhCOCH₂— | i-Bu | H | O | CH | | |
| 355 | 4-Cl-C₆H₄-CH₂— | i-Bu | H | S | CH | | |
| 356 | Ph— | i-Bu | H | S | CH | | |
| 357 | 4-Me-C₆H₄-CH₂— | i-Bu | H | S | CH | | |
| 358 | PhCH₂— | i-Bu | H | S | CH | | |
| 359 | 4-Cl-C₆H₄— | i-Bu | H | S | CH | | |
| 360 | 2-Cl-4-CF₃-C₆H₃— | i-Bu | H | S | CH | | |

TABLE 51

| No | R¹ | R² | R³ | X | Y | mp(°C.) | ¹H-NMR(CDCl₃) |
|---|---|---|---|---|---|---|---|
| 361 | Ph(CH₂)₂— | i-Bu | H | O | CH | | |
| 362 | PhO(CH₂)₃— | i-Bu | H | O | CH | | |
| 363 | 5-Me-isoxazol-3-yl-CH₂— | i-Bu | H | O | N | | |
| 364 | 4-CF₃-pyridin-2-yl— | i-Bu | H | O | N | | |
| 365 | 4-Cl-C₆H₄-CH₂— | i-Bu | H | O | N | | |

TABLE 51-continued
| No | R¹ | R² | R³ | X | Y | mp(°C.) | ¹H-NMR(CDCl₃) |
|---|---|---|---|---|---|---|---|
| 366 | 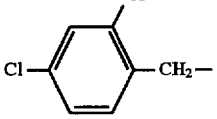 | i-Bu | H | O | N | | |
| 367 | 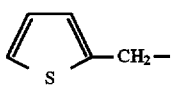 | i-Bu | H | O | CH | | |
TABLE 52
| No | R¹ | R² | R³ | X | Y | mp(°C.) | ¹H-NMR(CDCl₃) |
|---|---|---|---|---|---|---|---|
| 368 | 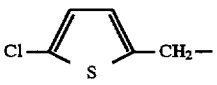 | i-Bu | H | O | CH | | |
| 369 | 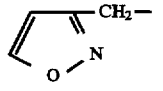 | i-Bu | H | O | CH | | |
| 370 | 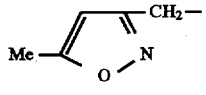 | i-Bu | H | O | CH | 92–93 | 0.98(6H, d, J=6.7), 2.10(1H, sept, J=6.7), 2.38(3H, s), 4.02(2H, d, J=6.7), 4.98(2H, s), 5.59(1H, s), 7.01–7.52(6H, m), 8.09(1H, s) |
| 371 | 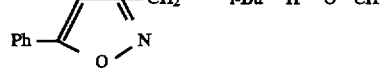 | i-Bu | H | O | CH | | |
| 372 | 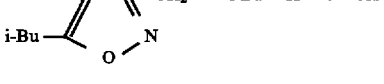 | i-Bu | H | O | CH | | |
| 373 | 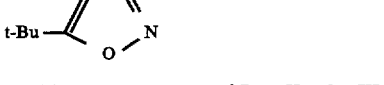 | i-Bu | H | O | CH | | |
| 374 | 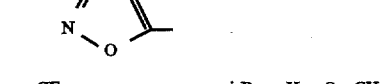 | i-Bu | H | O | CH | | |
| 375 | 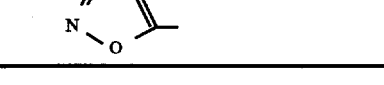 | i-Bu | H | O | CH | | |
TABLE 53
| No | R¹ | R² | R³ | X | Y | mp(°C.) | ¹H-NMR(CDCl₃) |
|---|---|---|---|---|---|---|---|
| 376 | 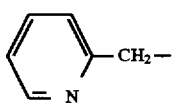 | i-Bu | H | O | CH | | 0.99(6H, d, J=6.7), 2.12(1H, sept, J=6.7), 4.04(2H, d, J=6.7), 5.09(2H, s), 6.84(1H, d, J=7.9), 6.99–7.65(8H, m), 8.12(1H, s), 8.51(1H, d, J=4.3) |

TABLE 53-continued

| No | R¹ | R² | R³ | X | Y | mp(°C.) | ¹H-NMR(CDCl₃) |
|---|---|---|---|---|---|---|---|
| 377 | 5-Cl, 2-pyridyl-CH₂— | i-Bu | H | O | CH | | |
| 378 | 2-pyridyl | i-Bu | H | O | CH | | |
| 379 | 5-Cl-2-pyridyl | i-Bu | H | O | CH | | |
| 380 | 3-Cl-2-pyridyl | i-Bu | H | O | CH | | |
| 381 | 3,5-diCl-2-pyridyl | i-Bu | H | O | CH | | 0.87(6H, d, J=6.7), 1.93(1H, sept, J=6.7), 3.87(2H, d, J=6.7), 6.94(1H, s), 7.11(1H, s), 7.25–7.59(4H, m), 7.66(1H, d, J=2.4), 7.83(1H, d, J=2.4), 7.93(1H, s) |
| 382 | 3-CF₃-2-pyridyl | i-Bu | H | O | CH | | |

TABLE 54

| No | R¹ | R² | R³ | X | Y | mp(°C.) | ¹H-NMR(CDCl₃) |
|---|---|---|---|---|---|---|---|
| 383 | 5-CF₃-2-pyridyl | i-Bu | H | O | CH | | 0.84(6H, d, J=6.7), 1.89(1H, sept, J=6.7), 3.84(2H, d, J=6.7), 6.79(1H, d, J=5.9), 6.94(1H, s), 7.10(1H, s), 7.25–7.60(4H, m), 7.81(1H, dd, J=8.6, 2.4), 7.93(1H, s), 8.31(1H, d, J=2.4) |
| 384 | 3-Cl-5-CF₃-2-pyridyl | i-Bu | H | O | CH | | |
| 385 | pyrazinyl | i-Bu | H | O | CH | | |
| 386 | 3-Cl-pyrazin-2-yl | i-Bu | H | O | CH | 81.5–82.5 | 0.87(6H, d, J=6.7), 1.90(1H, spet, J=6.7), 3.83(2H, d, J=6.7), 6.78(1H, s), 6.99(1H, s), 7.13(1H, s), 7.25–7.65(4H, m), 7.92(1H, s), 8.47(1H, s) |

TABLE 54-continued
| No | R¹ | R² | R³ | X | Y | mp(°C.) | ¹H-NMR(CDCl₃) |
|---|---|---|---|---|---|---|---|
| 387 | 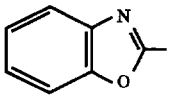 | i-Bu | H | O | CH | | |
| 388 | 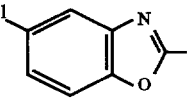 | i-Bu | H | O | CH | | |
| 389 | 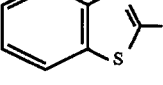 | i-Bu | H | O | CH | | |
| 390 | 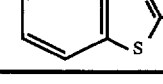 | i-Bu | H | O | CH | | |
TABLE 55
| No | R¹ | R² | R³ | X | Y | mp(°C.) | ¹H-NMR(CDCl₃) |
|---|---|---|---|---|---|---|---|
| 391 | 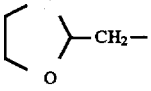 | i-Bu | H | O | CH | | |
| 392 | 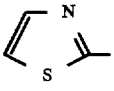 | i-Bu | H | O | CH | | |
| 393 | 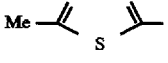 | i-Bu | H | O | CH | | |
| 394 | 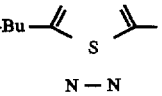 | i-Bu | H | O | CH | | |
| 395 | 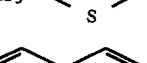 | i-Bu | H | O | CH | | |
| 396 | 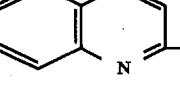 | i-Bu | H | O | CH | | |
| 397 | 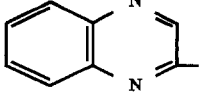 | i-Bu | H | O | CH | | |

TABLE 56

| No | R¹ | R² | R³ | X | Y | mp(°C.) | ¹H-NMR(CDCl₃) |
|---|---|---|---|---|---|---|---|
| 398 | 4-Me, 5-Cl, 6-Me pyrimidinyl | i-Bu | H | O | CH | | |
| 399 | 4-Et, 5-Cl, 6-Me pyrimidinyl | i-Bu | H | O | CH | | |
| 400 | 5-Cl, 3-CF₃, 2-Me pyridinyl | i-Bu | H | O | CH | | |

TABLE 57

| No | R¹ | R² | R³ | X | Y | mp(°C.) | ¹H-NMR(CDCl₃) |
|---|---|---|---|---|---|---|---|
| 401 | 2-Me-benzyl | Me | 4-MeO | O | CH | 97.5–98.5 | 2.17(3H, s), 3.84(3H, s), 4.00(3H, s), 4.90(2H, s), 6.55–7.43(9H, m), 7.93(1H, s) |
| 402 | 3-Me-benzyl | Me | 4-MeO | O | CH | | |
| 403 | 4-Me-benzyl | Me | 4-MeO | O | CH | 79.5–80.5 | 2.32(3H, s), 3.83(3H, s), 4.00(3H, s), 4.86(2H, s), 6.52–7.43(9H,m), 7.95(1H, s) |
| 404 | 2-F-benzyl | Me | 4-MeO | O | CH | | |
| 405 | 3-F-benzyl | Me | 4-MeO | O | CH | | |
| 406 | 4-F-benzyl | Me | 4-MeO | O | CH | 71–72 | 3.84(3H, s), 4.00(3H, s), 4.84(2H, s), 6.50–7.04(7H, m), 7.22(1H, s), 7.44(1H, d, J=8.5), 7.91 (1H, s) |

TABLE 57-continued
| No | R¹ | R² | R³ | X | Y | mp(°C.) | ¹H-NMR(CDCl₃) |
|----|----|----|----|----|----|----|----|
| 407 | 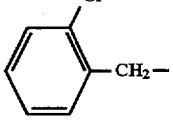 | Me | 4-MeO | O | CH | 121.5–122.5 | 3.84(3H, s), 4.03(3H, s), 5.02(2H, s), 6.55–6.89(3H, m), 7.00(1H, s), 7.17–7.33(4H, m), 7.44(1H, d, J=8.5), 8.00(1H, s) |
TABLE 58
| No | R¹ | R² | R³ | X | Y | mp(°C.) | ¹H-NMR(CDCl₃) |
|----|----|----|----|----|----|----|----|
| 408 | 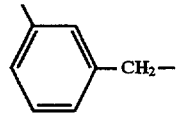 | Me | 4-MeO | O | CH | | |
| 409 | 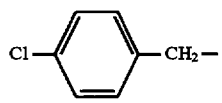 | Me | 4-MeO | O | CH | 106–107 | 3.84(3H, s), 4.01(3H, s), 4.85(2H, s), 6.49–7.28(8H, m), 7.44(1H, d, J=8.5), 7.93(1H, s) |
| 410 | 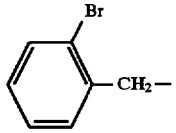 | Me | 4-MeO | O | CH | | |
| 411 | 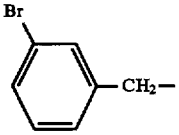 | Me | 4-MeO | O | CH | | |
| 412 | 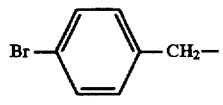 | Me | 4-MeO | O | CH | | |
| 413 | 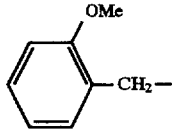 | Me | 4-MeO | O | CH | | |
| 414 | 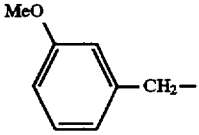 | Me | 4-MeO | O | CH | | |
| 415 | 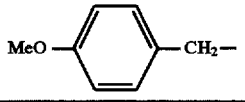 | Me | 4-MeO | O | CH | | 3.79(3H, s), 3.83(3H, s), 4.00(3H, s), 4.82(2H, s), 6.52–7.44(9H, m), 7.94(1H, s) |

TABLE 59

| No  | R¹ | R² | R³ | X | Y | mp(°C.) | ¹H-NMR(CDCl₃) |
|-----|----|----|----|---|---|---------|----------------|
| 416 | 2-I-C₆H₄-CH₂- | Me | 4-MeO | O | CH | | |
| 417 | 2-CN-C₆H₄-CH₂- | Me | 4-MeO | O | CH | | |
| 418 | 3-CN-C₆H₄-CH₂- | Me | 4-MeO | O | CH | | |
| 419 | 4-CN-C₆H₄-CH₂- | Me | 4-MeO | O | CH | | |
| 420 | 2-NO₂-C₆H₄-CH₂- | Me | 4-MeO | O | CH | | |
| 421 | 3-NO₂-C₆H₄-CH₂- | Me | 4-MeO | O | CH | | |
| 422 | 4-NO₂-C₆H₄-CH₂- | Me | 4-MeO | O | CH | | |
| 423 | 4-i-Pr-C₆H₄-CH₂- | Me | 4-MeO | O | CH | | |

TABLE 60

| No  | R¹ | R² | R³ | X | Y | mp(°C.) | ¹H-NMR(CDCl₃) |
|-----|----|----|----|---|---|---------|----------------|
| 424 | 4-t-Bu-C₆H₄-CH₂- | Me | 4-MeO | O | CH | | |
| 425 | 2-CF₃-C₆H₄-CH₂- | Me | 4-MeO | O | CH | | |

TABLE 60-continued

| No | R¹ | R² | R³ | X | Y | mp(°C.) | ¹H-NMR(CDCl₃) |
|---|---|---|---|---|---|---|---|
| 426 | CF₃-phenyl-CH₂- | Me | 4-MeO | O | CH | 108.5–109.5 | 3.85(3H, s), 4.02(3H, s), 4.94(2H, s), 6.52(1H, d, J=1.8), 6.60(1H, dd, J=8.6, 2.5), 7.02(1H, s), 7.15–7.55(5H, m), 7.90(1H, s) |
| 427 | CF₃-phenyl-CH₂- | Me | 4-MeO | O | CH | | |
| 428 | PhO-phenyl-CH₂- | Me | 4-MeO | O | CH | | |
| 429 | 2,4-diMe-phenyl-CH₂- | Me | 4-MeO | O | CH | | |
| 430 | 3,4-diMe-phenyl-CH₂- | Me | 4-MeO | O | CH | | |

TABLE 61

| No | R¹ | R² | R³ | X | Y | mp(°C.) | ¹H-NMR(CDCl₃) |
|---|---|---|---|---|---|---|---|
| 431 | 2,4-diCl-phenyl-CH₂- | Me | 4-MeO | O | CH | | |
| 432 | 2,6-diCl-phenyl-CH₂- | Me | 4-MeO | O | CH | | |
| 433 | 3,4-diCl-phenyl-CH₂- | Me | 4-MeO | O | CH | 110–111 | 3.85(3H, s), 4.02(3H, s), 4.83(2H, s), 6.47(1H, d, J=1.8), 6.60(1H, dd, J=8.6, 2.6), 6.82(1H, dd, J=8.5, 2.4), 7.06(1H, s), 7.14(1H, d, J=1.8), 7.28(1H, s), 7.37(1H, d, J=7.9), 7.46(1H, d, J=7.9), 7.90(1H, s) |
| 434 | 3,5-diCl-phenyl-CH₂- | Me | 4-MeO | O | CH | | |

TABLE 61-continued
| No | R¹ | R² | R³ | X | Y | mp(°C.) | ¹H-NMR(CDCl₃) |
|----|----|----|----|---|---|---------|----------------|
| 435 | 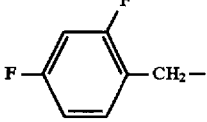 | Me | 4-MeO | O | CH | | |
| 436 | 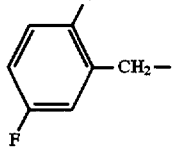 | Me | 4-MeO | O | CH | | |
| 437 | 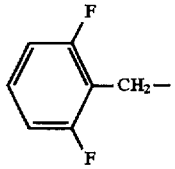 | Me | 4-MeO | O | CH | | |
TABLE 62
| No | R¹ | R² | R³ | X | Y | mp(°C.) | ¹H-NMR(CDCl₃) |
|----|----|----|----|---|---|---------|----------------|
| 438 | 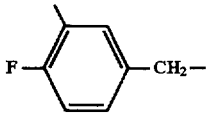 | Me | 4-MeO | O | CH | | |
| 439 | 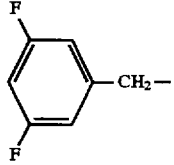 | Me | 4-MeO | O | CH | | |
| 440 | 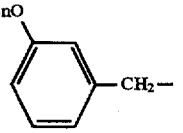 | Me | 4-MeO | O | CH | | |
| 441 | 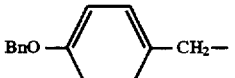 | Me | 4-MeO | O | CH | | |
| 442 | 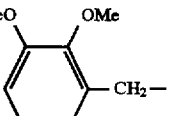 | Me | 4-MeO | O | CH | | |
| 443 | 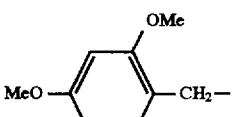 | Me | 4-MeO | O | CH | | |

TABLE 62-continued

| No | R¹ | R² | R³ | X | Y | mp(°C.) | ¹H-NMR(CDCl₃) |
|---|---|---|---|---|---|---|---|
| 444 | 2-OMe, 4-MeO-benzyl (CH₂–) | Me | 4-MeO | O | CH | | |
| 445 | 2-MeO, 3-MeO-benzyl (CH₂–) | Me | 4-MeO | O | CH | | |

TABLE 63

| No | R¹ | R² | R³ | X | Y | mp(°C.) | ¹H-NMR(CDCl₃) |
|---|---|---|---|---|---|---|---|
| 446 | 3,5-(MeO)₂-benzyl (CH₂–) | Me | 4-MeO | O | CH | | |
| 447 | 4-MeS-benzyl (CH₂–) | Me | 4-MeO | O | CH | | |
| 448 | 4-CF₃O-benzyl (CH₂–) | Me | 4-MeO | O | CH | | |
| 449 | 2,4,6-Me₃-benzyl (CH₂–) | Me | 4-MeO | O | CH | | |
| 450 | 4-MeSO₂-benzyl (CH₂–) | Me | 4-MeO | O | CH | | |
| 451 | 4-biphenylmethyl (CH₂–) | Me | 4-MeO | O | CH | | |
| 452 | PhOCH₂CH₂— | Me | 4-MeO | O | CH | | 3.85(3H, s), 3.92(2H, t, J=4.9), 4.00(3H, s), 4.15(2H, t, J=4.9), 6.51–7.33(9H, m), 7.46(1H, d, J=8.5), 7.84(1H, s) |

TABLE 64

| No | R¹ | R² | R³ | X | Y | mp(°C.) | ¹H-NMR(CDCl₃) |
|---|---|---|---|---|---|---|---|
| 453 | MeOCOCH₂— | Me | 4-MeO | O | CH | | |
| 454 | PhCOCH₂— | Me | 4-MeO | O | CH | | |

TABLE 64-continued
| No | R¹ | R² | R³ | X | Y | mp(°C.) | ¹H-NMR(CDCl₃) |
|---|---|---|---|---|---|---|---|
| 455 | 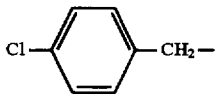 4-Cl-C₆H₄-CH₂- | Me | 4-MeO | S | CH | | |
| 456 | 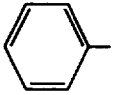 C₆H₅- | Me | 4-MeO | S | CH | | |
| 457 | 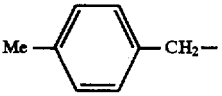 4-Me-C₆H₄-CH₂- | Me | 4-MeO | S | CH | | |
| 458 | 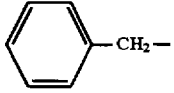 C₆H₅-CH₂- | Me | 4-MeO | S | CH | | |
| 459 | 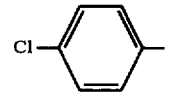 4-Cl-C₆H₄- | Me | 4-MeO | S | CH | | |
| 460 | 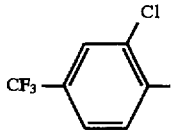 2-Cl-4-CF₃-C₆H₃- | Me | 4-MeO | S | CH | | |
TABLE 65
| No | R¹ | R² | R³ | X | Y | mp(°C.) | ¹H-NMR(CDCl₃) |
|---|---|---|---|---|---|---|---|
| 461 | 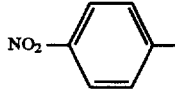 4-NO₂-C₆H₄- | Me | 4-MeO | S | CH | | |
| 462 | 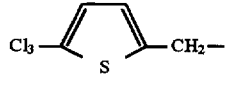 5-Cl₃-thienyl-CH₂- | Me | 4-MeO | O | N | | |
| 463 | 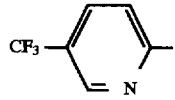 4-CF₃-pyridyl- | Me | 4-MeO | O | N | | |
| 464 | 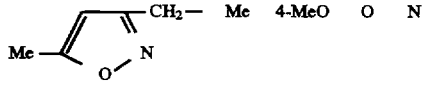 3-Me-isoxazol-5-yl-CH₂- | Me | 4-MeO | O | N | | |
| 465 | 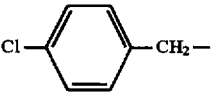 4-Cl-C₆H₄-CH₂- | Me | 4-MeO | O | N | | |
| 466 | 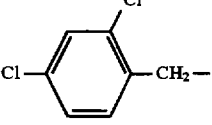 2,4-diCl-C₆H₃-CH₂- | Me | 4-MeO | O | N | | |

TABLE 65-continued
| No | R¹ | R² | R³ | X | Y | mp(°C.) | ¹H-NMR(CDCl₃) |
|---|---|---|---|---|---|---|---|
| 467 | 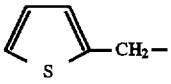 | Me | 4-MeO | O | CH | | |
| 468 | 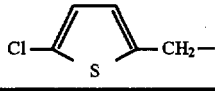 | Me | 4-MeO | O | CH | | |
TABLE 66
| No | R¹ | R² | R³ | X | Y | mp (°C.) | ¹H-NMR (CDCl₃) |
|---|---|---|---|---|---|---|---|
| 469 | 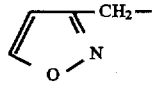 | Me | 4-MeO | O | CH | | |
| 470 | 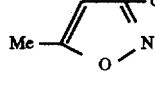 | Me | 4-MeO | O | CH | 98.5–99.5 | 2.38(3H, s), 3.84(3H, s), 4.02(3H, s), 4.95(2H, s), 5.58(1H, s), 6.57–6.61(2H, m), 7.04(1H, s),7.21–7.22(1H, m), 7.44(1H, d, J=8.5), 7.95(1H, s) |
| 471 | 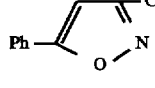 | Me | 4-MeO | O | CH | | |
| 472 | 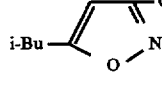 | Me | 4-MeO | O | CH | | |
| 473 | 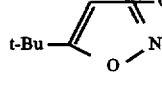 | Me | 4-MeO | O | CH | | |
| 474 | 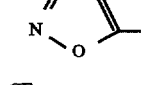 | Me | 4-MeO | O | CH | | |
| 475 | 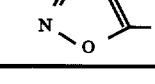 | Me | 4-MeO | O | CH | | |
TABLE 67
| No | R¹ | R² | R³ | X | Y | mp (°C.) | ¹H-NMR (CDCl₃) |
|---|---|---|---|---|---|---|---|
| 476 | 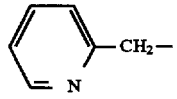 | Me | 4-MeO | O | CH | | |
| 477 | 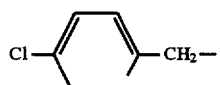 | Me | 4-MeO | O | CH | | |

TABLE 67-continued

| No | R¹ | R² | R³ | X | Y | mp (°C.) | ¹H-NMR (CDCl₃) |
|---|---|---|---|---|---|---|---|
| 478 | 2-pyridyl | Me | 4-MeO | O | CH | | |
| 479 | 5-Cl-2-pyridyl | Me | 4-MeO | O | CH | | |
| 480 | 3-Cl-2-pyridyl | Me | 4-MeO | O | CH | | |
| 481 | 3,5-diCl-2-pyridyl | Me | 4-MeO | O | CH | | 3.85(3H, s), 3.88(3H, s), 6.79(1H, d, J=2.4), 6.86(1H, dd, J=8.6, 2.5), 6.94(1H, s), 7.10(1H, s), 7.34(1H, d, J=9.2), 7.68(1H, dd, J=9.2, 1.8), 7.84–7.86(2H, m) |
| 482 | 3-CF₃-2-pyridyl | Me | 4-MeO | O | CH | | |

TABLE 68

| No | R¹ | R² | R³ | X | Y | mp (°C.) | ¹H-NMR (CDCl₃) |
|---|---|---|---|---|---|---|---|
| 483 | 5-CF₃-2-pyridyl | Me | 4-MeO | O | CH | | 3.86(6H, s), 6.76–6.92(4H, m), 7.08(1H, s), 7.42(1H, d, J=8.6), 7.79–7.84(2H, m), 8.33(1H, s) |
| 484 | 3-Cl-5-CF₃-2-pyridyl | Me | 4-MeO | O | CH | | |
| 485 | pyrimidinyl | Me | 4-MeO | O | CH | | |
| 486 | 4-Cl-pyrimidinyl | Me | 4-MeO | O | CH | | |
| 487 | benzoxazol-2-yl | Me | 4-MeO | O | CH | | |

TABLE 68-continued

| No | R¹ | R² | R³ | X | Y | mp (°C.) | ¹H-NMR (CDCl₃) |
|---|---|---|---|---|---|---|---|
| 488 | 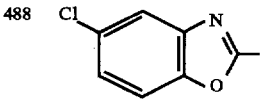 5-Cl-benzoxazol-2-yl | Me | 4-MeO | O | CH | | |
| 489 | 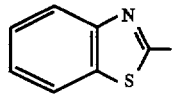 benzothiazol-2-yl | Me | 4-MeO | O | CH | | |
| 490 | 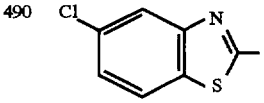 5-Cl-benzothiazol-2-yl | Me | 4-MeO | O | CH | | |

TABLE 69

| No | R¹ | R² | R³ | X | Y | mp (°C.) | ¹H-NMR (CDCl₃) |
|---|---|---|---|---|---|---|---|
| 491 | 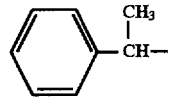 PhCH(CH₃)— | Me | H | O | CH | | 1.30(3H, d, J=6.1), 4.07(3H, s), 5.14(1H, q, J=6.1), 6.71(1H, d, J=8.6), 6.96(1H, t, J=6.7), 7.22–7.31(8H, m), 7.48(1H, dd, J=7.3, 1.8), 7.99(1H, s) |
| 492 | 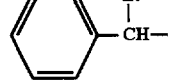 PhCH(Et)— | Me | H | O | CH | | 0.72(3H, t, J=7.3), 1.57–1.68(2H, m), 4.07(3H, s), 4.92(1H, t, J=6.7), 6.68(1H, d, J=7.9), 6.94(1H, t, J=7.3), 7.09–7.48(9H, m), 8.01(1H, s) |
| 493 | 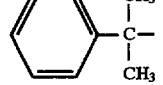 PhC(CH₃)₂— | Me | H | O | CH | | |
| 494 | 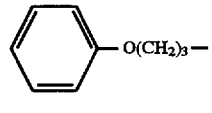 PhO(CH₂)₃— | Me | H | O | CH | | 1.94(2H, quint, J=6.1), 3.77(2H, t, J=6.1), 4.03(3H, s), 4.03(2H, t, J=6.1), 6.81–7.52(11H, m), 7.98(1H, s) |
| 495 | 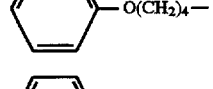 PhO(CH₂)₄— | Me | H | O | CH | | 1.62–1.70(4H, m), 3.88(4H, q, J=6.7), 4.04(3H, s), 6.85–7.52(11H, m), 7.92(1H, s) |
| 496 | 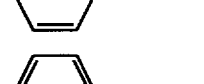 Ph(CH₂)₂— | Me | H | O | CH | | 2.75(2H, t, J=7.3), 4.03(2H, t, J=7.3), 4.04(3H, s), 6.90(1H, d, J=8.5), 7.00–7.17(4H, m), 7.19–7.50(6H, m), 7.96(1H, s) |
| 497 | 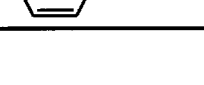 Ph(CH₂)₃— | Me | H | O | CH | | 1.77(2H, quint, J=6.1), 2.47(2H, t, J=6.1), 3.82(2H, t, J=6.1), 4.05(3H, s), 6.86(1H, d, J=8.6), 7.00–7.52(11H, m), 7.96(1H, s) |

TABLE 70
| No | R¹ | R² | R³ | X | Y | mp (°C.) | ¹H-NMR (CDCl₃) |
|---|---|---|---|---|---|---|---|
| 498 | 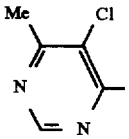 | Me | 4-MeO | O | CH | | |
| 498 | 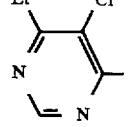 | Me | 4-MeO | O | CH | | |
| 500 | 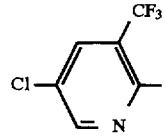 | Me | 4-MeO | O | CH | | |
TABLE 71
| No | R¹ | R² | R³ | X | Y | mp (°C.) | ¹H-NMR(CDCl₃) |
|---|---|---|---|---|---|---|---|
| 501 | 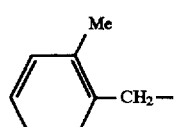 | Me | 5-Cl | O | CH | 107–108.5 | 2.16(3H, s), 4.02(3H, s), 6.94–6.99(3H, m), 7.09–7.24(4H, m), 7.42(1H, dd, J=8.6, 2.4), 7.49(1H, d, J=2.4), 7.95(1H, s) |
| 502 | 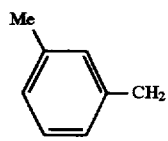 | Me | 5-Cl | O | CH | | |
| 503 | 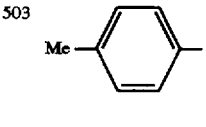 | Me | 5-Cl | O | CH | 112–113 | 2.32(3H, s), 4.03(3H, s), 4.88(2H, s), 6.88–7.18(7H, m), 7.40(1H, dd, J=8.5, 2.4), 7.49(1H, d, J=2.4), 7.97(1H, s) |
| 504 | 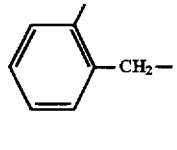 | Me | 5-Cl | O | CH | | |
| 505 | 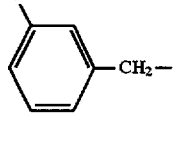 | Me | 5-Cl | O | CH | | |
| 506 |  | Me | 5-Cl | O | CH | 107–18 | 4.03(3H, s), 4.86(2H, s), 6.89–6.99(5H, m), 7.03(1H, s), 7.18(1H d, J=1.2), 7.42(1H, dd, J=8.6, 2.4), 7.51(1H, d, J=2.4), 7.93(1H, s) |

TABLE 71-continued

| No | R¹ | R² | R³ | X | Y | mp (°C.) | ¹H-NMR(CDCl₃) |
|---|---|---|---|---|---|---|---|
| 507 | 2-Cl-C₆H₄-CH₂- | Me | 5-Cl | O | CH | 126–127 | 4.06(3H, s), 5.04(2H, s), 6.85–6.97(2H, m), 7.02(1H, s), 7.15–7.34(4H, m), 7.44(1H, dd, J=8.6, 2.4), 7.52(1H, d, J=2.4), 8.02(1H, s) |

TABLE 72

| No | R¹ | R² | R³ | X | Y | Mp (°C.) | ¹H-NMR(CDCl₃) |
|---|---|---|---|---|---|---|---|
| 508 | 3-Cl-C₆H₄-CH₂- | Me | 5-Cl | O | CH | | |
| 509 | 4-Cl-C₆H₄-CH₂- | Me | 5-Cl | O | CH | 131.5–133 | 4.04(3H, s), 4.87(2H, s), 6.87–6.94(3H, m), 7.04(1H, s), 7.18–7.29(3H, m), 7.42(1H, dd, J=8.6, 2.4), 7.51(1H, d, J=2.4), 7.94(1H, s) |
| 510 | 2-Br-C₆H₄-CH₂- | Me | 5-Cl | O | CH | | |
| 511 | 3-Br-C₆H₄-CH₂- | Me | 5-Cl | O | CH | | |
| 512 | 4-Br-C₆H₄-CH₂- | Me | 5-Cl | O | CH | | |
| 513 | 2-MeO-C₆H₄-CH₂- | Me | 5-Cl | O | CH | | |
| 514 | 3-MeO-C₆H₄-CH₂- | Me | 5-Cl | O | CH | | |
| 515 | 4-MeO-C₆H₄-CH₂- | Me | 5-Cl | O | CH | 123–125 | 3.79(3H, s), 4.02(3H, s), 4.84(2H, s), 6.80–6.95(5H, m), 7.04(1H, s), 7.16–7.50(3H, m), 7.96(1H, s) |

TABLE 73

| No | R¹ | R² | R³ | X | Y | Mp (°C.) | ¹H-NMR(CDCl₃) |
|---|---|---|---|---|---|---|---|
| 516 | 2-I-benzyl (-CH₂-C₆H₄-I) | Me | 5-Cl | O | CH | | |
| 517 | 2-CN-benzyl | Me | 5-Cl | O | CH | | |
| 518 | 3-CN-benzyl | Me | 5-Cl | O | CH | | |
| 519 | 4-CN-benzyl | Me | 5-Cl | O | CH | | |
| 520 | 2-NO₂-benzyl | Me | 5-Cl | O | CH | | |
| 521 | 3-NO₂-benzyl | Me | 5-Cl | O | CH | | |
| 522 | 4-NO₂-benzyl | Me | 5-Cl | O | CH | | |

TABLE 74

| No | R¹ | R² | R³ | X | Y | mp (°C.) | ¹H-NMR(CDCl₃) |
|---|---|---|---|---|---|---|---|
| 523 | 4-i-Pr-benzyl | Me | 5-Cl | O | CH | | |
| 524 | 4-t-Bu-benzyl | Me | 5-Cl | O | CH | | |
| 525 | 2-CF₃-benzyl | Me | 5-Cl | O | CH | | |

TABLE 74-continued
| No | R¹ | R² | R³ | X | Y | mp (°C.) | ¹H-NMR(CDCl₃) |
|---|---|---|---|---|---|---|---|
| 526 | 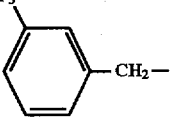 3-CF₃-C₆H₄-CH₂- | Me | 5-Cl | O | CH | 114–116 | 4.04(3H, s), 4.96(2H, s), 6.961(1H, d, J=9.2), 7.03(1H, s), 7.14–7.23(2H, m), 7.36–7.56(5H, m), 7.92(1H, s) |
| 527 | 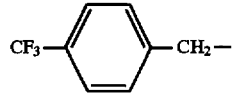 4-CF₃-C₆H₄-CH₂- | Me | 5-Cl | O | CH | | |
| 528 | 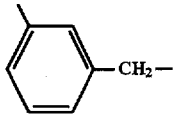 3-PhO-C₆H₄-CH₂- | Me | 5-Cl | O | CH | | |
| 529 | 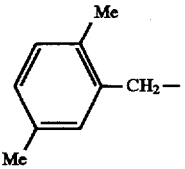 2,4-Me₂-C₆H₃-CH₂- | Me | 5-Cl | O | CH | | |
| 530 | 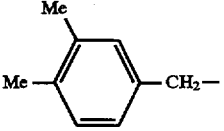 3,4-Me₂-C₆H₃-CH₂- | Me | 5-Cl | O | CH | | |
TABLE 75
| No | R¹ | R² | R³ | X | Y | mp (°C.) | ¹H-NMR(CDCl₃) |
|---|---|---|---|---|---|---|---|
| 531 | 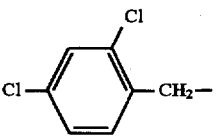 2,4-Cl₂-C₆H₃-CH₂- | Me | 5-Cl | O | CH | 103.5–105 | 4.06(3H, s), 4.98(2H, s), 6.74–6.95(2H, m), 7.03(1H, s), 7.16–7.21(2H, m), 7.35(1H, d, J=2.4), 7.45(1H, dd, J=8.5, 2.4), 7.53(1H, d, J=2.4), 8.00(1H, s) |
| 532 | 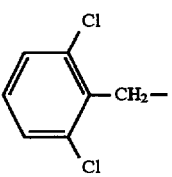 2,6-Cl₂-C₆H₃-CH₂- | Me | 5-Cl | O | CH | | |
| 533 | 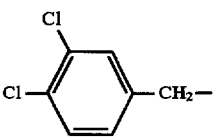 3,4-Cl₂-C₆H₃-CH₂- | Me | 5-Cl | O | CH | 130–132 | 4.05(3H, s), 4.85(2H, s), 6.80–6.90(2H, m), 7.08(1H, s), 7.13–7.53(5H, m), 793(1H, s) |
| 534 | 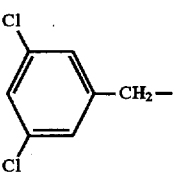 3,5-Cl₂-C₆H₃-CH₂- | Me | 5-Cl | O | CH | | |

TABLE 75-continued
| No | R¹ | R² | R³ | X | Y | mp (°C.) | ¹H-NMR(CDCl₃) |
|----|----|----|----|---|---|----------|----------------|
| 535 | 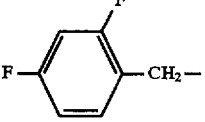 | Me | 5-Cl | O | CH | | |
| 536 | 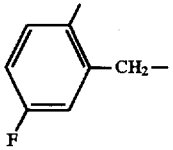 | Me | 5-Cl | O | CH | | |
| 537 | 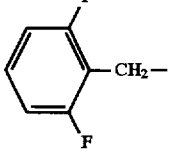 | Me | 5-Cl | O | CH | | |
TABLE 76
| No | R¹ | R² | R³ | X | Y | mp (°C.) | ¹H—NMR(CDCl₃) |
|----|----|----|----|---|---|----------|----------------|
| 538 | 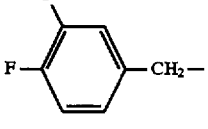 | Me | 5-Cl | O | CH | | |
| 539 | 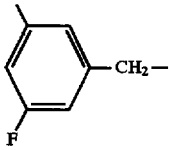 | Me | 5-Cl | O | CH | | |
| 540 | 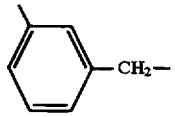 | Me | 5-Cl | O | CH | | |
| 541 | 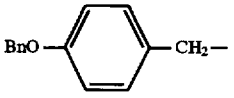 | Me | 5-Cl | O | CH | | |
| 542 | 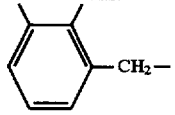 | Me | 5-Cl | O | CH | | |
| 543 | 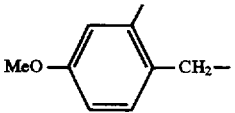 | Me | 5-Cl | O | CH | | |

TABLE 76-continued
| No | R¹ | R² | R³ | X | Y | mp (°C.) | ¹H—NMR(CDCl₃) |
|---|---|---|---|---|---|---|---|
| 544 | 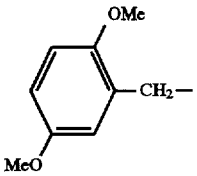 2-OMe, 5-MeO benzyl | Me | 5-Cl | O | CH | | |
| 545 | 2,3-(MeO)₂ benzyl | Me | 5-Cl | O | CH | | |
TABLE 77
| No | R¹ | R² | R³ | X | Y | mp (°C.) | ¹H—NMR(CDCl₃) |
|---|---|---|---|---|---|---|---|
| 546 | 3,5-(MeO)₂ benzyl | Me | 5-Cl | O | CH | | |
| 547 | 4-MeS-benzyl | Me | 5-Cl | O | CH | | |
| 548 | 4-CF₃O-benzyl | Me | 5-Cl | O | CH | | |
| 549 | 2,4,6-Me₃-benzyl | Me | 5-Cl | O | CH | | |
| 550 | 4-MeSO₂-benzyl | Me | 5-Cl | O | CH | | |
| 551 | 4-Ph-benzyl | Me | 5-Cl | O | CH | | |
| 552 | PhOCH₂CH₂— | Me | 5-Cl | O | CH | | 3.93(2H, t, J=5.5), 4.02(3H, s), 4.15(2H, t, J=5.5), 6.81–7.53(10H, m), 7.87(1H, s) |
TABLE 78
| No | R¹ | R² | R³ | X | Y | mp (°C.) | ¹H—NMR(CDCl₃) |
|---|---|---|---|---|---|---|---|
| 553 | MeOCOCH₂— | Me | 5-Cl | O | CH | | |
| 554 | PhCOCH₂— | Me | 5-Cl | O | CH | | |

TABLE 78-continued
| No | R¹ | R² | R³ | X | Y | mp (°C.) | ¹H—NMR(CDCl₃) |
|---|---|---|---|---|---|---|---|
| 555 | 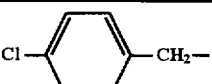 4-Cl-C₆H₄-CH₂— | Me | 5-Cl | S | CH | | |
| 556 | 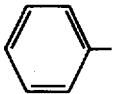 C₆H₅— | Me | 5-Cl | S | CH | | |
| 557 | 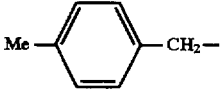 4-Me-C₆H₄-CH₂— | Me | 5-Cl | S | CH | | |
| 558 | 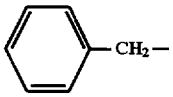 C₆H₅-CH₂— | Me | 5-Cl | S | CH | | |
| 559 | 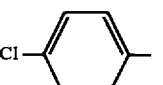 4-Cl-C₆H₄— | Me | 5-Cl | S | CH | | |
| 560 | 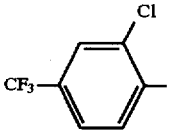 2-Cl-4-CF₃-C₆H₃— | Me | 5-Cl | S | CH | | |
TABLE 79
| No | R¹ | R² | R³ | X | Y | mp (°C.) | ¹H—NMR(CDCl₃) |
|---|---|---|---|---|---|---|---|
| 561 | 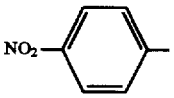 4-NO₂-C₆H₄— | Me | 5-Cl | S | CH | | |
| 562 | 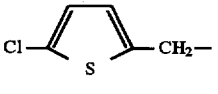 5-Cl-thiophene-2-CH₂— | Me | 5-Cl | O | N | | |
| 563 | 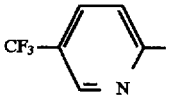 5-CF₃-pyridin-2-yl— | Me | 5-Cl | O | N | | 4.03(3H, s), 6.69(1H, d, J=8.5), 7.22(1H, d, J=8.5), 7.50–7.83(4H, m), 8.37(1H, d, J=1.8), 8.89(1H, s) |
| 564 | 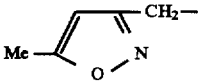 3-Me-isoxazol-5-CH₂— | Me | 5-Cl | O | N | | |
| 565 | 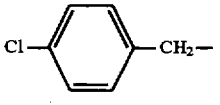 4-Cl-C₆H₄-CH₂— | Me | 5-Cl | O | N | 136–137.5 | 4.10(3H, s), 4.86(2H, s), 6.85–6.94(3H, m), 7.24–7.29(2H, m), 7.40(1H, dd, J=8.5, 2.4), 7.53(1H, d, J=2.4), 7.92(1H, s), 9.04(1H, s) |
| 566 | 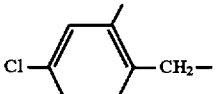 2,4-Cl₂-C₆H₃-CH₂— | Me | 5-Cl | O | N | | |

TABLE 79-continued
| No | R¹ | R² | R³ | X | Y | mp (°C.) | ¹H—NMR(CDCl₃) |
|---|---|---|---|---|---|---|---|
| 567 | 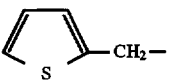 | Me | 5-Cl | O | CH | | |
| 568 | 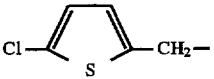 | Me | 5-Cl | O | CH | 104–105 | |
TABLE 80
| No | R¹ | R² | R³ | X | Y | mp (°C.) | ¹H—NMR(CDCl₃) |
|---|---|---|---|---|---|---|---|
| 569 | 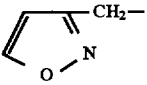 | Me | 5-Cl | O | CH | | |
| 570 | 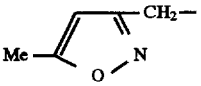 | Me | 5-Cl | O | CH | 88–90 | 2.38(3H, s), 4.05(3H, s), 4.96(2H, s), 5.58(1H, s), 6.98(1H, d, J=9.2), 7.05(1H, s), 7.18(1H, s), 7.43(1H, dd, J=9.2, 2.4), 7.51(1H, d, J=2.4), 7.98(1H, s) |
| 571 | 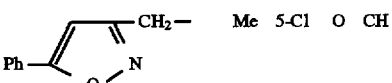 | Me | 5-Cl | O | CH | | |
| 572 | 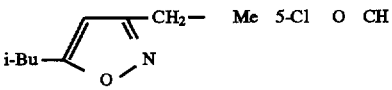 | Me | 5-Cl | O | CH | | |
| 573 | 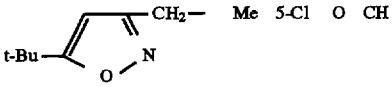 | Me | 5-Cl | O | CH | | |
| 574 | 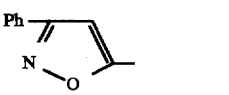 | Me | 5-Cl | O | CH | | |
| 575 | 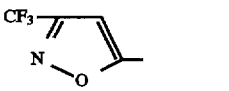 | Me | 5-Cl | O | CH | | |
TABLE 81
| No | R¹ | R² | R³ | X | Y | mp (°C.) | ¹H—NMR(CDCl₃) |
|---|---|---|---|---|---|---|---|
| 576 | 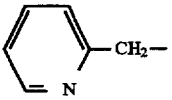 | Me | 5-Cl | O | CH | | |
| 577 | 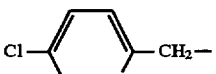 | Me | 5-Cl | O | CH | | |
| 578 | 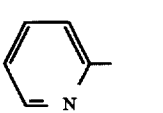 | Me | 5-Cl | O | CH | | |

TABLE 81-continued
| No | R¹ | R² | R³ | X | Y | mp (°C.) | ¹H—NMR(CDCl₃) |
|----|----|----|----|----|----|----|----|
| 579 | 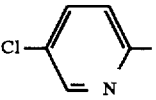 | Me | 5-Cl | O | CH | | |
| 580 | 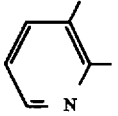 | Me | 5-Cl | O | CH | | |
| 581 | 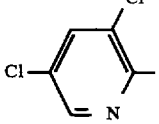 | Me | 5-Cl | O | CH | | 3.94(3H, s), 6.93(1H, s), 7.06(1H, s), 7.21(1H, d, J = 8.5), 7.48–7.54(2H, m), 7.67(1H, d, J = 2.4), 7.80–7.86(2H, m) |
| 582 | 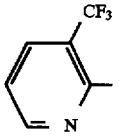 | Me | 5-Cl | O | CH | | |
TABLE 82
| No | R¹ | R² | R³ | X | Y | mp (°C.) | ¹H—NMR(CDCl₃) |
|----|----|----|----|----|----|----|----|
| 583 | 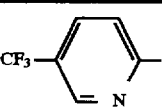 | Me | 5-Cl | O | CH | | 3.93(3H, s), 6.77(1H, d, J = 8.6), 6.91(1H, s) 7.05(1H, s), 7.22(1H, d, J = 8.6), 7.51–7.55(2H, m), 7.82(1H, dd, J = 8.6, 2.4), 7.87(1H, s), 8.30(1H, d, J = 1.8) |
| 584 | 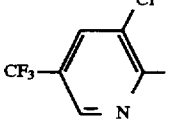 | Me | 5-Cl | O | CH | | |
| 585 | 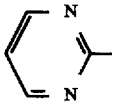 | Me | 5-Cl | O | CH | | |
| 586 | 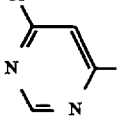 | Me | 5-Cl | O | CH | | |
| 587 | 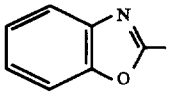 | Me | 5-Cl | O | CH | | |
| 588 | 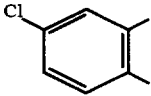 | Me | 5-Cl | O | CH | | |

TABLE 82-continued
| No | R¹ | R² | R³ | X | Y | mp (°C.) | ¹H—NMR(CDCl₃) |
|---|---|---|---|---|---|---|---|
| 589 | 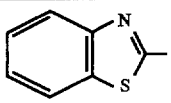 | Me | 5-Cl | O | CH | | |
| 590 | 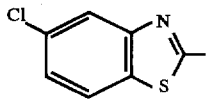 | Me | 5-Cl | O | ch | | |
TABLE 83
| No | R¹ | R² | R³ | X | Y | mp (°C.) | ¹H—NMR(CDCl₃) |
|---|---|---|---|---|---|---|---|
| 591 | 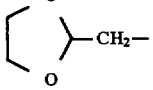 | Me | 5-Cl | O | CH | | |
| 592 | 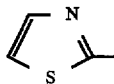 | Me | 5-Cl | O | CH | | 4.00(3H, s), 6.78(1H, d, J = 3.7), 6.99(1H, s), 7.10–7.11(2H, m), 7.41–7.53(3H, m), 7.96(1H, s) |
| 593 | 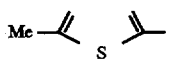 | Me | 5-Cl | O | CH | | |
| 594 | 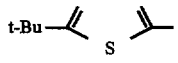 | Me | 5-Cl | O | CH | | |
| 595 | 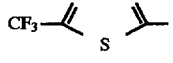 | Me | 5-Cl | O | CH | | |
| 596 | 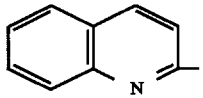 | Me | 5-Cl | O | CH | | |
| 597 | 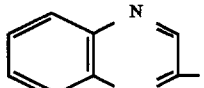 | Me | 5-Cl | O | CH | | |
TABLE 84
| No | R¹ | R² | R³ | X | Y | mp (°C.) | ¹H—NMR(CDCl₃) |
|---|---|---|---|---|---|---|---|
| 598 | 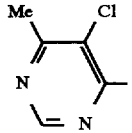 | Me | 5-Cl | O | CH | | |

TABLE 84-continued

| No | R¹ | R² | R³ | X | Y | mp (°C.) | ¹H—NMR(CDCl₃) |
|---|---|---|---|---|---|---|---|
| 599 | Et, Cl substituted pyrimidine (see structure) | | Me | 5-Cl | O | CH | |
| 600 | Cl, CF₃ substituted pyridine (see structure) | | Me | 5-Cl | O | CH | |

TABLE 85

| No | R¹ | R² | R³ | X | Y | mp (°C.) | ¹H—NMR(CDCl₃) |
|---|---|---|---|---|---|---|---|
| 601 | 2-Me-C₆H₄-CH₂— | n-Pr | H | O | CH | | |
| 602 | 3-Me-C₆H₄-CH₂— | n-Pr | H | O | CH | | |
| 603 | 4-Me-C₆H₄-CH₂— | n-Pr | H | O | CH | 78–80 | 0.98(3H, t, J = 7.3), 1.76(2H, sext, J = 7.3), 2.32(3H, s), 4.18(2H, t, J = 7.3), 4.91(2H, s), 6.91–7.50(10H, m), 8.04(1H, s) |
| 604 | 2-F-C₆H₄-CH₂— | n-Pr | H | O | CH | | |
| 605 | 3-F-C₆H₄-CH₂— | n-Pr | H | O | CH | | |
| 606 | 4-F-C₆H₄-CH₂— | n-Pr | H | O | CH | | 0.98(3H, t, J = 7.3), 1.76(2H, sext, J = 7.3), 4.18(2H, t, J = 7.3), 4.90(2H, s), 6.93–7.54(10H, m), 7.99(1H, s) |
| 607 | 2-Cl-C₆H₄-CH₂— | n-Pr | H | O | CH | | |

TABLE 86
| No | R¹ | R² | R³ | X | Y | mp (°C.) | ¹H—NMR(CDCl₃) |
|----|----|----|----|---|---|----------|---------------|
| 608 | 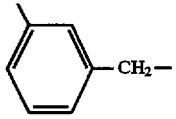 Cl | n-Pr | H | O | CH | | |
| 609 | 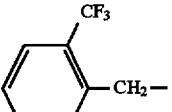 Cl | n-Pr | H | O | CH | 69–71 | 0.99(3H, t, J = 7.3), 1.77(2H, sept, J = 7.3), 4.19(3H, t, J = 7.3), 4.90(2H, s), 6.94–7.53 (10H, m), 8.00(1H, s) |
| 610 | 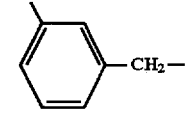 CF₃ | n-Pr | H | O | CH | | |
| 611 | 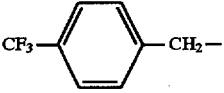 CF₃ | n-Pr | H | O | CH | | |
| 612 | 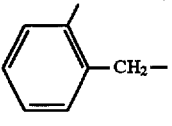 CF₃ | n-Pr | H | O | CH | | |
| 613 | 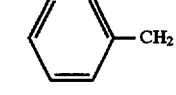 OMe | n-Pr | H | O | CH | | |
| 614 | MeO 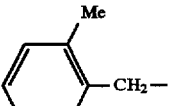 | n-Pr | H | O | CH | | |
| 615 | MeO 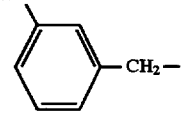 | n-Pr | H | O | CH | | 0.98(3H, t, J = 7.3), 1.76(2H, sext, J = 7.3), 3.79(3H, s), 4.18(2H, t, J = 7.3), 4.87(2H, s), 6.80–7.51 (10H, m), 8.02(1H, s) |
TABLE 87
| No | R¹ | R² | R³ | X | Y | mp (°C.) | ¹H—NMR(CDCl₃) |
|----|----|----|----|---|---|----------|---------------|
| 616 | Me | i-Pr | H | O | CH | | |
| 617 | Me | i-Pr | H | O | CH | | |

TABLE 87-continued
| No | R¹ | R² | R³ | X | Y | mp (°C.) | ¹H—NMR(CDCl₃) |
|---|---|---|---|---|---|---|---|
| 618 | 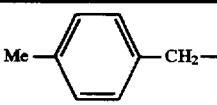 Me—⟨⟩—CH₂— | i-Pr | H | O | CH | | 1.33(6H, d, J = 6.7), 2.32(3H, s), 4.48(1H, sept, J = 6.7), 4.91(2H, s), 6.91–7.50(10H, m), 8.07(1H, s) |
| 619 | 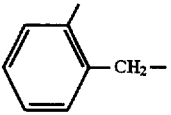 2-F-C₆H₄-CH₂— | i-Pr | H | O | CH | | |
| 620 | 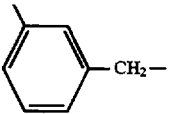 3-F-C₆H₄-CH₂— | i-Pr | H | O | CH | | |
| 621 |  F—⟨⟩—CH₂— | i-Pr | H | O | CH | 65–67 | 1.33(6H, d, J = 6.1), 4.48(1H, sept, J = 6.1), 4.90(2H, s), 6.93–7.52(10H, m), 8.02(1H, s) |
| 622 | 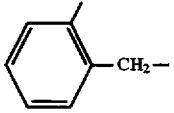 2-Cl-C₆H₄-CH₂— | i-Pr | H | O | CH | 65–67 | 1.35(6H, d, J = 6.1), 4.51 (1H, sept, J = 6.1) 5.07(2H, s), 6.90–7.53(10H, m), 8.13)1H, s) |
TABLE 88
| No | R¹ | R² | R³ | X | Y | mp (°C.) | ¹H—NMR(CDCl₃) |
|---|---|---|---|---|---|---|---|
| 623 | 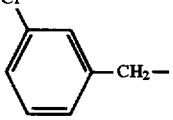 3-Cl-C₆H₄-CH₂— | i-Pr | H | O | CH | | |
| 624 | 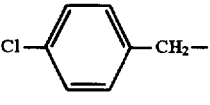 Cl—⟨⟩—CH₂— | i-Pr | H | O | CH | 86–87 | 1.34(6H, d, J = 6.1), 4.48(1H, sept, J = 6.1), 4.90(2H, s), 6.94–7.52(10H, m), 8.03(1H, s) |
| 625 | 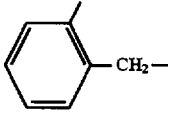 2-CF₃-C₆H₄-CH₂— | i-Pr | H | O | CH | | |
| 626 | 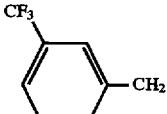 3-CF₃-C₆H₄-CH₂— | i-Pr | H | O | CH | | |
| 627 | 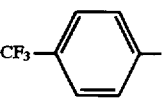 CF₃—⟨⟩—CH₂— | i-Pr | H | O | CH | | |

TABLE 88-continued
| No | R¹ | R² | R³ | X | Y | mp (°C.) | ¹H—NMR(CDCl₃) |
|---|---|---|---|---|---|---|---|
| 628 | 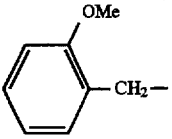 | i-Pr | H | O | CH | | |
| 629 | 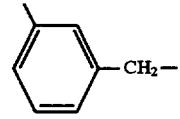 | i-Pr | H | O | CH | | |
| 630 |  | i-Pr | H | O | CH | | 1.33(6H, d, J = 6.1), 3.79(3H, s), 4.48(1H, sept, J = 6.1), 4.87(2H, s), 6.80–7.50(10H, m), 8.06(1H, s) |
TABLE 89
| No | R¹ | R² | R³ | X | Y | mp (°C.) | ¹H—NMR(CDCl₃) |
|---|---|---|---|---|---|---|---|
| 631 | 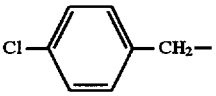 | n-Pr | H | O | N | | |
| 632 | 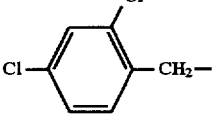 | n-Pr | H | O | CH | | |
| 633 | 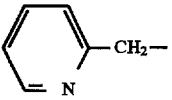 | n-Pr | H | O | CH | | |
| 634 | 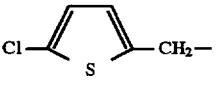 | n-Pr | H | O | CH | | 0.99(3H, t, J = 7.3), 1.78(2H, sext, J = 7.3), 4.19(2H, t, J = 7.3), 4.99(2H, s), 6.64(1H, d, J = 3.7), 6.74(1H, d, J = 3.7), 6.98–7.60(6H, m), 8.01 (1H, s) |
| 635 | 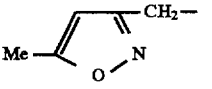 | n-Pr | H | O | CH | 70–71 | 1.00(3H, t, J = 7.3), 1.79(2H, sext, J = 7.3) 2.37(3H, s), 4.20(2H, t, J = 7.3), 4.98(2H, s), 5.58(1H, s), 7.01–7.52(6H, m), 8.04(1H, s) |
| 636 | 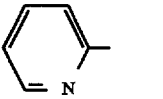 | n-Pr | H | O | CH | | |
| 637 | 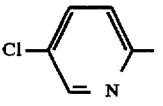 | n-Pr | H | O | CH | | |
| 638 | 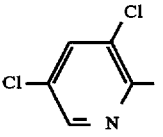 | n-Pr | H | O | CH | | |

TABLE 90

| No | R¹ | R² | R³ | X | Y | mp (°C.) | ¹H—NMR(CDCl₃) |
|---|---|---|---|---|---|---|---|
| 639 | 3-CF₃-pyridin-2-yl | n-Pr | H | O | CH | | |
| 640 | 5-CF₃-pyridin-2-yl | n-Pr | H | O | CH | | 0.86(3H, t, J = 7.3), 1.61(2H, sext, J = 7.3), 4.03(2H, t, J = 7.3), 6.79(1H, d, J = 8.6), 6.93(1H, s), 7.09(1H, s), 7.25–7.60(4H, m), 7.82(1H, dd, J = 9.2, 2.4), 7.93(1H, s), 8.31(1H, d, J = 2.4) |
| 641 | 4-Cl-pyrimidin-2-yl | n-Pr | H | O | CH | | |
| 642 | benzoxazol-2-yl | n-Pr | H | O | CH | | |
| 643 | benzothiazol-2-yl | n-Pr | H | O | CH | | |
| 644 | thiazol-2-yl | n-Pr | H | O | CH | | |
| 645 | pyrimidin-2-yl | n-Pr | H | O | CH | | |

TABLE 91

| No | R¹ | R² | R³ | X | Y | mp(°C.) | ¹H-NMR(CDCl₃) |
|---|---|---|---|---|---|---|---|
| 646 | 4-Cl-C₆H₄-CH₂— | i-Pr | H | O | N | | |
| 647 | 2,4-Cl₂-C₆H₃-CH₂— | i-Pr | H | O | CH | | |
| 648 | pyridin-2-yl-CH₂— | i-Pr | H | O | CH | | |
| 649 | 5-Cl-thiophen-2-yl-CH₂— | i-Pr | H | O | CH | | 1.35(6H, d, J=6.7), 4.49(1H, sept, J=6.1), 4.99(2H, s), 6.64(1H, d, J=4.3), 6.73(1H, d, J=3.7), 6.97–7.50(6H, m), 8.04(1H, s) |

TABLE 91-continued

| No | R¹ | R² | R³ | X | Y | mp(°C.) | ¹H-NMR(CDCl₃) |
|---|---|---|---|---|---|---|---|
| 650 | Me-[isoxazole]-CH₂— | i-Pr | H | O | CH | 69–70 | 1.35(6H, d, J=6.1), 2.38(3H, s), 4.50(1H, sept, J=6.1), 4.98(2H, s), 5.59(1H, s), 7.00–7.52(5H, m), 8.07(1H, s) |
| 651 | [pyridin-2-yl]- | i-Pr | H | O | CH | | |
| 652 | 5-Cl-[pyridin-2-yl]- | i-Pr | H | O | CH | | |

TABLE 92

| No | R¹ | R² | R³ | X | Y | mp(°C.) | ¹H-NMR(CDCl₃) |
|---|---|---|---|---|---|---|---|
| 653 | 3,5-diCl-[pyridin-2-yl]- | i-Pr | H | O | CH | | |
| 654 | 3-CF₃-[pyridin-2-yl]- | i-Pr | H | O | CH | | |
| 655 | 4-CF₃-[pyridin-2-yl]- | i-Pr | H | O | CH | | 1.20(6H, d, J=6.1), 4.35(1H, sept, J=6.1), 6.79(1H, d, J=8.6), 6.92(1H, s), 7.08(1H, s), 7.25–7.60(4H, m), 7.81(1H, dd, J=9.2, 2.4), 7.96(1H, s), 8.31(1H, d, J=1.8) |
| 656 | 4-Cl-[pyrimidin-2-yl]- | i-Pr | H | O | CH | | |
| 657 | benzoxazol-2-yl | i-Pr | H | O | CH | | |
| 658 | benzothiazol-2-yl | i-Pr | H | O | CH | | |
| 659 | thiazol-2-yl | i-Pr | H | O | CH | | |
| 660 | pyrimidin-2-yl | i-Pr | H | O | CH | | |

TABLE 93
| No | R¹ | R² | R³ | X | Y | mp(°C.) | ¹H-NMR(CDCl₃) |
|---|---|---|---|---|---|---|---|
| 661 | 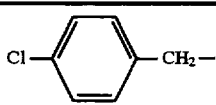 | Benzyl | H | O | CH | 94–95.5 | 4.89(2H, s), 5.25(2H, s), 6.95–6.97(4H, m), 7.01(1H, s), 7.06(1H, t, J=6.7), 7.23–7.48(9H, m), 7.99(1H, s) |
| 662 | 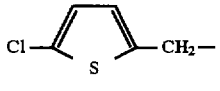 | Benzyl | H | O | CH | | |
| 663 | 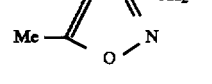 | Benzyl | H | O | CH | | |
| 664 | 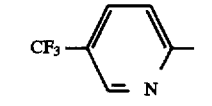 | Benzyl | H | O | CH | | |
| 665 | 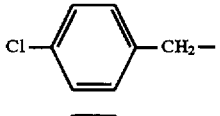 | FCH₂CH₂— | H | O | CH | 106–107.5 | 4.40(1H, t, J=4.0), 4.51(1H, t, J=4.0), 4.62 (1H, t, J=4.0), 4.80(1H, t, J=4.0), 4.90(2H, s), 6.94–7.53(10H, m), 7.96(1H, s) |
| 666 | 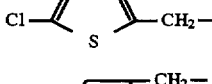 | FCH₂CH₂— | H | O | CH | | |
| 667 | 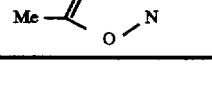 | FCH₂CH₂— | H | O | CH | | |
TABLE 94
| No | R¹ | R² | R³ | X | Y | mp(°C.) | ¹H-NMR(CDCl₃) |
|---|---|---|---|---|---|---|---|
| 668 | 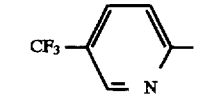 | FCH₂CH₂— | H | O | CH | | |
| 669 |  | CH≡CCH₂— | H | O | CH | 75–78 | 2.52(1H, t, J=2.4), 4.81(2H, d, J=2.4), 4.90(2H, s), 6.94–7.55(10H, m), 7.95(1H, s) |
| 670 | 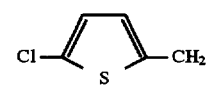 | CH≡CCH₂— | H | O | CH | | |
| 671 | 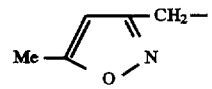 | CH≡CCH₂— | H | O | CH | | |
| 672 | 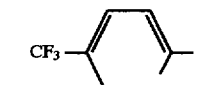 | CH≡CCH₂— | H | O | CH | | |
| 673 | 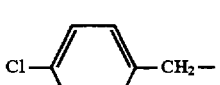 | 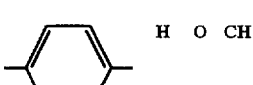 | H | O | CH | | 4.93(2H, s), 6.95(1H, s), 6.99(1H, s), 7.03(1H, d, J=7.9), 7.11–7.27(4H, m), 7.42(1H, d, J=8.6), 7.49(1H, s), 7.53–7.64(2H, m), 7.95(1H, dd, J=8.6, 2.4), 7.97(1H, s), 8.59(1H, s) |

TABLE 94-continued

| No | R¹ | R² | R³ | X | Y | mp(°C.) | ¹H-NMR(CDCl₃) |
|---|---|---|---|---|---|---|---|
| 674 | Cl-[thiophene]-CH₂- | CF₃-[pyridine]- | H | O | CH | | |
| 675 | CF₃-[pyridine]- | CF₃-[pyridine]- | H | O | CH | | |

TABLE 95

| No | R¹ | R² | R³ | X | Y | mp(°C.) | ¹H-NMR(CDCl₃) |
|---|---|---|---|---|---|---|---|
| 676 | Cl-[phenyl]-CH₂- | [cyclopentyl]- | H | O | CH | 100.5–101.5 | 1.60–1.97(8H, m), 4.80–4.86(1H, m), 4.91(2H, s), 6.95–7.52(10H, m), 8.02(1H, s) |
| 677 | Cl-[thiophene]-CH₂- | [cyclopentyl]- | H | O | CH | | |
| 678 | Me-[isoxazole]-CH₂- | [cyclopentyl]- | H | O | CH | | |
| 679 | CF₃-[pyridine]- | [cyclopentyl]- | H | O | CH | | |
| 680 | Cl-[phenyl]-CH₂- | O₂N-[phenyl]- | H | O | CH | 159.5–160.5 | 4.93(2H, s), 6.95(1H, s), 6.98(1H, s), 7.04(1H, d, J=7.9), 7.13–7.65(9H, m), 8.00(1H, s), 8.23(1H, s), 8.27(1H, s) |
| 681 | Cl-[thiophene]-CH₂- | O₂N-[phenyl]- | H | O | CH | | |
| 682 | Me-[isoxazole]-CH₂- | O₂N-[phenyl]- | H | O | CH | | |

TABLE 96

| No | R¹ | R² | R³ | X | Y | mp(°C.) | ¹H-NMR(CDCl₃) |
|---|---|---|---|---|---|---|---|
| 683 | CF₃-[pyridine]- | O₂N-[phenyl]- | H | O | CH | | |
| 684 | Cl-[phenyl]-CH₂- | ClCH=CHCH₂- | H | O | CH | | 4.67–4.70(1H, m), 4.90(2H, s), 4.92–4.94(1H, m), 6.06–6.37(1H, m), 6.94–7.52(10H, m), 7.95(1H, d, J=4.9) |

TABLE 96-continued
| No | R¹ | R² | R³ | X | Y | mp(°C.) | ¹H-NMR(CDCl₃) |
|---|---|---|---|---|---|---|---|
| 685 | 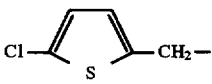 | ClCH=CHCH₂— | H | O | CH | | |
| 686 | 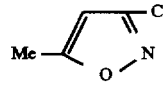 | ClCH=CHCH₂— | H | O | CH | | |
| 687 | 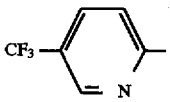 | ClCH=CHCH₂— | H | O | CH | | |
| 688 | 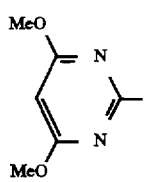 | Me | H | O | CH | | 3.79(6H, s), 3.93(3H, s), 5.73(1H, s), 6.91(1H, s), 7.06(1H, s), 7.28–7.57(4H, m), 7.85(1H, s) |
| 689 | 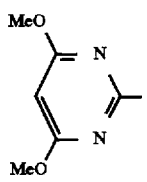 | Et | H | O | CH | | |
| 690 | 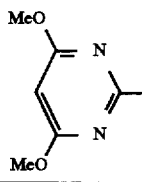 | i-Bu | H | O | CH | | 0.89(6H, d, J=6.7), 1.98(1H, sept, J=6.7), 3.78(6H, s), 3.88(2H, d, J=6.7), 5.72(1H, s), 6.92(1H, s), 7.07(1H, d, J=1.2), 7.27–7.56(4H, m), 7.89(1H, s) |
TABLE 97
| No | R¹ | R² | R³ | X | Y | mp(°C.) | ¹H-NMR(CDCl₃) |
|---|---|---|---|---|---|---|---|
| 691 | 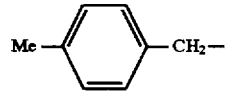 | Me | 5-Me | O | CH | 109.5–110.5 | |
| 692 | 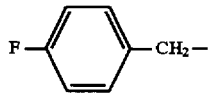 | Me | 5-Me | O | CH | 101–102 | |
| 693 | 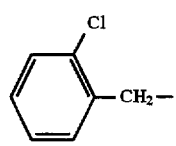 | Me | 5-Me | O | CH | | |
| 694 | 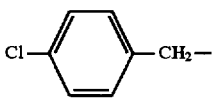 | Me | 5-Me | O | CH | 125–126 | |

TABLE 97-continued
| No | R¹ | R² | R³ | X | Y | mp(°C.) | ¹H-NMR(CDCl₃) |
|---|---|---|---|---|---|---|---|
| 695 |  | Me | 5-Me | O | CH | | |
| 696 | 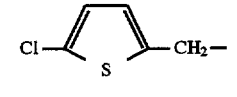 | Me | 5-Me | O | CH | 112.5–113.5 | |
| 697 | 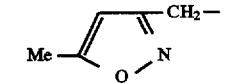 | Me | 5-Me | O | CH | | |
TABLE 98
| No | R¹ | R² | R³ | X | Y | mp(°C.) | ¹H-NMR(CDCl₃) |
|---|---|---|---|---|---|---|---|
| 698 | 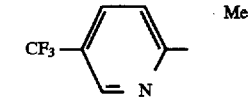 | Me | 5-Me | O | CH | | 2.41(3H, s), 3.89(3H, s), 6.77(1H, d, J=8.6), 6.91(1H, d, J=1.2), 7.08–7.39(4H, m), 7.80(1H, dd, J=9.2, 3.0), 7.88(1H, s), 8.31(1H, d, J=2.4) |
| 699 | 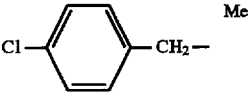 | Me | 5-Me | O | N | | |
| 700 | 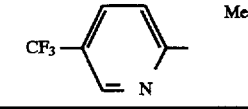 | Me | 5-Me | O | N | | |
TABLE 99
| No | R¹ | R² | R³ | X | Y | mp(°C.) | ¹H-NMR(CDCl₃) |
|---|---|---|---|---|---|---|---|
| 701 | 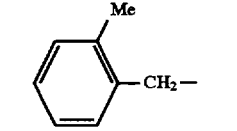 | Me | 5-F | O | CH | 65.5–68 | 2.17(3H, s), 4.02(3H, s), 4.90(2H, s), 6.94–6.99(3H, m), 7.10–7.25(6H, m), 7.95(1H, s) |
| 702 | 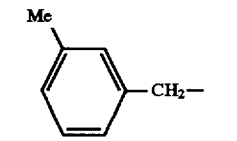 | Me | 5-F | O | CH | | |
| 703 | 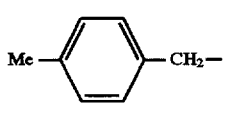 | Me | 5-F | O | CH | 89–90 | 2.32(3H, s), 4.03(3H, s), 4.86(2H, s), 6.87–6.95(3H, m), 7.04–7.26(6H, m), 7.98(1H, s) |
| 704 | 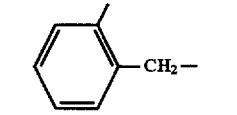 | Me | 5-F | O | CH | | |

TABLE 99-continued
| No | R¹ | R² | R³ | X | Y | mp(°C.) | ¹H-NMR(CDCl₃) |
|---|---|---|---|---|---|---|---|
| 705 | 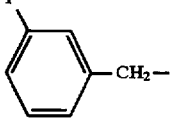 | Me | 5-F | O | CH | | |
| 706 | 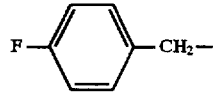 | Me | 5-F | O | CH | 104–105 | 4.03(3H, s), 4.85(2H, s), 6.89–6.99(4H, m), 7.04(1H, s), 7.13–7.20(2H, m), 7.25–7.30(2H, m), 7.94(1H, s) |
| 707 | 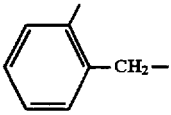 | Me | 5-F | O | CH | 104–105 | 4.05(3H, s), 5.20(2H, s), 6.87–6.99(2H, m), 7.20(1H, s), 7.14–7.36(6H, m), 8.02(1H, s) |
TABLE 100
| No | R¹ | R² | R³ | X | Y | mp(°C.) | ¹H-NMR(CDCl₃) |
|---|---|---|---|---|---|---|---|
| 708 | 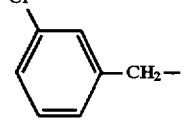 | Me | 5-F | O | CH | | |
| 709 | 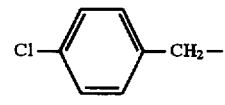 | Me | 5-F | O | CH | 114–116.5 | 4.03(3H, s), 4.86(2H, s), 6.88–6.95(3H, m), 7.04(1H, s), 7.13–7.29(5H, m), 7.95(1H, s) |
| 710 | 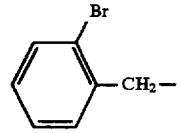 | Me | 5-F | O | CH | | |
| 711 | 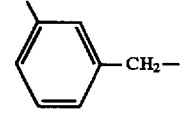 | Me | 5-F | O | CH | | |
| 712 | 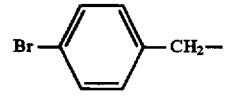 | Me | 5-F | O | CH | | |
| 713 | 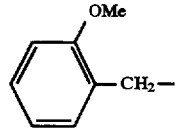 | Me | 5-F | O | CH | | |
| 714 | 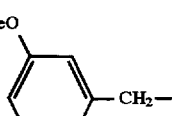 | Me | 5-F | O | CH | | |

TABLE 100-continued

| No | R¹ | R² | R³ | X | Y | mp(°C.) | ¹H-NMR(CDCl₃) |
|---|---|---|---|---|---|---|---|
| 715 | MeO-C₆H₄-CH₂- | Me | 5-F | O | CH | 91–92.5 | 3.79(3H, s), 4.02(3H, s), 4.83(2H, s), 6.80–6.96(5H, m), 7.04(1H, s), 7.12–7.26(3H, m), 7.96(1H, s) |

TABLE 101

| No | R¹ | R² | R³ | X | Y | mp(°C.) | ¹H-NMR(CDCl₃) |
|---|---|---|---|---|---|---|---|
| 716 | 2-I-C₆H₄-CH₂- | Me | 5-F | O | CH | | |
| 717 | 2-CN-C₆H₄-CH₂- | Me | 5-F | O | CH | | |
| 718 | 3-CN-C₆H₄-CH₂- | Me | 5-F | O | CH | | |
| 719 | 4-CN-C₆H₄-CH₂- | Me | 5-F | O | CH | | |
| 720 | 2-NO₂-C₆H₄-CH₂- | Me | 5-F | O | CH | | |
| 721 | 3-NO₂-C₆H₄-CH₂- | Me | 5-F | O | CH | | |
| 722 | 4-NO₂-C₆H₄-CH₂- | Me | 5-F | O | CH | | |

TABLE 102

| No | R¹ | R² | R³ | X | Y | mp(°C.) | ¹H-NMR(CDCl₃) |
|---|---|---|---|---|---|---|---|
| 723 | 4-i-Pr-C₆H₄-CH₂- | Me | 5-F | O | CH | | |

TABLE 102-continued

| No | R¹ | R² | R³ | X | Y | mp(°C.) | ¹H-NMR(CDCl₃) |
|---|---|---|---|---|---|---|---|
| 724 | 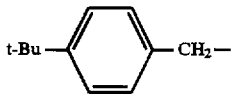 t-Bu—⟨⟩—CH₂— | Me | 5-F | O | CH | | |
| 725 | 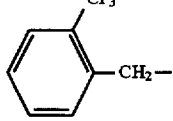 CF₃ substituted benzyl (2-CF₃) —CH₂— | Me | 5-F | O | CH | | |
| 726 | 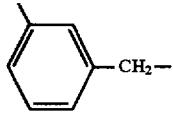 CF₃ substituted benzyl (3-CF₃) —CH₂— | Me | 5-F | O | CH | 88–90 | 4.04(3H, s), 4.95(2H, s), 6.93(1H, dd, J=9.2, 4.3), 7.03(1H, s), 7.15–7.31(4H, m), 7.37–7.56(3H, m), 7.92(1H, s) |
| 727 | 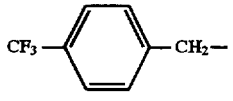 CF₃—⟨⟩—CH₂— | Me | 5-F | O | CH | | |
| 728 | 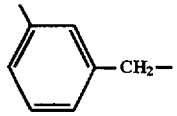 PhO substituted benzyl —CH₂— | Me | 5-F | O | CH | | |
| 729 | 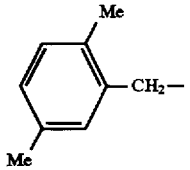 2,4-diMe benzyl —CH₂— | Me | 5-F | O | CH | | |
| 730 | 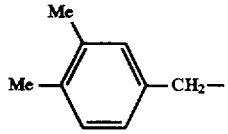 2,3-diMe benzyl —CH₂— | Me | 5-F | O | CH | | |

TABLE 103

| No | R¹ | R² | R³ | X | Y | mp(°C.) | ¹H-NMR(CDCl₃) |
|---|---|---|---|---|---|---|---|
| 731 | 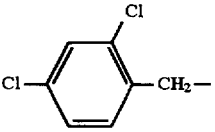 2,4-diCl benzyl —CH₂— | Me | 5-F | O | CH | 94.5–96 | 4.06(3H, s), 4.97(2H, s), 6.78(1H, d, J=8.6), 6.95(1H, dd, J=9.2, 4.3), 7.03(1H, s), 7.16–7.30(4H, m), 7.36(1H, d, J=1.8), 8.00(1H, s) |
| 732 | 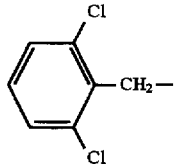 2,6-diCl benzyl —CH₂— | Me | 5-F | O | CH | | |

TABLE 103-continued
| No | R¹ | R² | R³ | X | Y | mp(°C.) | ¹H-NMR(CDCl₃) |
|---|---|---|---|---|---|---|---|
| 733 | 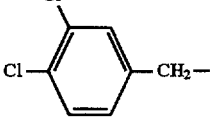 | Me | 5-F | O | CH | 103–104 | 4.05(3H, s), 4.84(2H, s), 6.83(1H, dd, J=8.5, 2.4), 6.89(1H, dd, J=9.2, 4.3), 7.07(1H, s), 7.14–7.30(5H, m), 7.93(1H, s) |
| 734 | 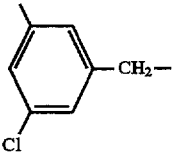 | Me | 5-F | O | CH | | |
| 735 | 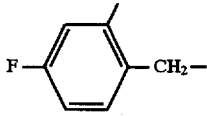 | Me | 5-F | O | CH | | |
| 736 | 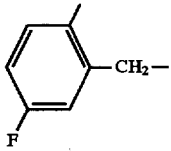 | Me | 5-F | O | CH | | |
| 737 | 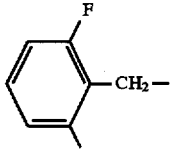 | Me | 5-F | O | CH | | |
TABLE 104
| No | R¹ | R² | R³ | X | Y | mp(°C.) | ¹H-NMR(CDCl₃) |
|---|---|---|---|---|---|---|---|
| 738 | 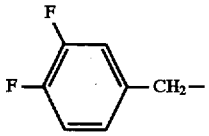 | Me | 5-F | O | CH | | |
| 739 | 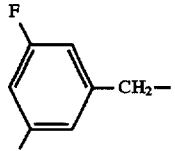 | Me | 5-F | O | CH | | |
| 740 | 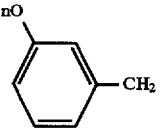 | Me | 5-F | O | CH | | |

TABLE 104-continued
| No | R¹ | R² | R³ | X | Y | mp(°C.) | ¹H-NMR(CDCl₃) |
|---|---|---|---|---|---|---|---|
| 741 | 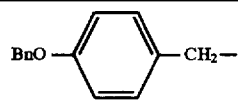 | Me | 5-F | O | CH | | |
| 742 | 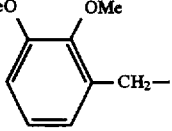 | Me | 5-F | O | CH | | |
| 743 | 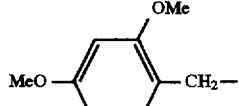 | Me | 5-F | O | CH | | |
| 744 | 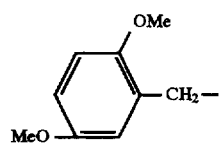 | Me | 5-F | O | CH | | |
| 745 | 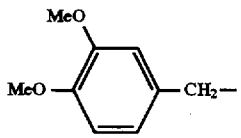 | Me | 5-F | O | CH | | |
TABLE 105
| No | R¹ | R² | R³ | X | Y | mp(°C.) | ¹H-NMR(CDCl₃) |
|---|---|---|---|---|---|---|---|
| 746 | 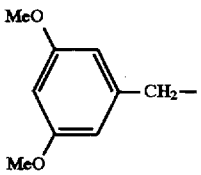 | Me | 5-F | O | CH | | |
| 747 |  | Me | 5-F | O | CH | | |
| 748 | 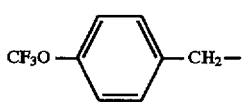 | Me | 5-F | O | CH | | |
| 749 | 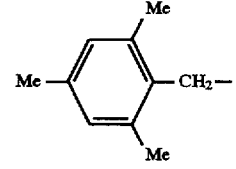 | Me | 5-F | O | CH | | |
| 750 | 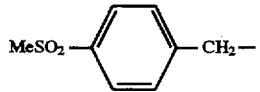 | Me | 5-F | O | CH | | |

TABLE 105-continued
| No | R¹ | R² | R³ | X | Y | mp(°C.) | ¹H-NMR(CDCl₃) |
|---|---|---|---|---|---|---|---|
| 751 | 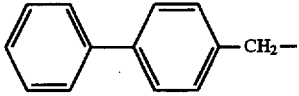 | Me | 5-F | O | CH | | |
| 752 | PhOCH₂CH₂— | Me | 5-F | O | CH | 75–76 | 3.92(2H, t, J=4.9), 4.02(3H, s), 4.14(2H, t, J=4.9), 6.81–7.36(10H, m), 7.88(1H, s) |
TABLE 106
| No | R¹ | R² | R³ | X | Y | mp(°C.) | ¹H-NMR(CDCl₃) |
|---|---|---|---|---|---|---|---|
| 753 | MeOCOCH₂— | Me | 5-F | O | CH | | |
| 754 | PhCOCH₂— | Me | 5-F | O | CH | | |
| 755 | 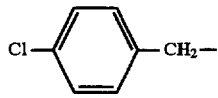 | Me | 5-F | S | CH | | |
| 756 | 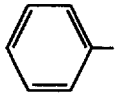 | Me | 5-F | S | CH | | |
| 757 | 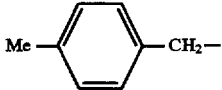 | Me | 5-F | S | CH | | |
| 758 | 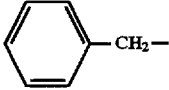 | Me | 5-F | S | CH | | |
| 759 | 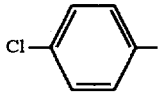 | Me | 5-F | S | CH | | |
| 760 | 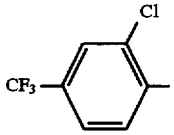 | Me | 5-F | S | CH | | |
TABLE 107
| No | R¹ | R² | R³ | X | Y | mp(°C.) | ¹H-NMR(CDCl₃) |
|---|---|---|---|---|---|---|---|
| 761 | 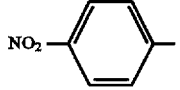 | Me | 5-F | S | CH | | |
| 762 | 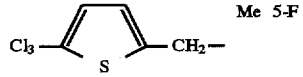 | Me | 5-F | O | N | | |
| 763 | 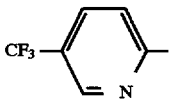 | Me | 5-F | O | N | | 4.02(3H, s), 6.69(1H, d, J=8.6), 7.21–7.38(3H, m), 7.77(1H, s), 7.81(1H, dd, J=8.6, 2.4), 8.37(1H, br-s), 8.88(1H, s) |

TABLE 107-continued
| No | R¹ | R² | R³ | X | Y | mp(°C.) | ¹H-NMR(CDCl₃) |
|---|---|---|---|---|---|---|---|
| 764 | 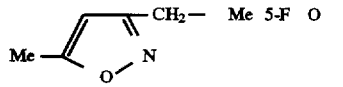 | Me | 5-F | O | N | | |
| 765 | 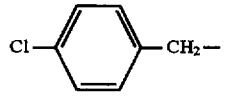 | Me | 5-F | O | N | 85.5–87 | 4.10(3H, s), 4.85(2H, s), 6.85–6.95(3H, m), 7.11–7.31(4H, m), 7.92(1H, s), 9.04(1H, s) |
| 766 | 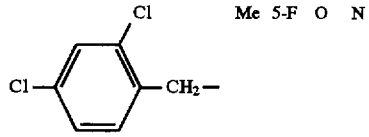 | Me | 5-F | O | N | | |
| 767 | 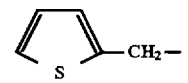 | Me | 5-F | O | CH | | |
| 768 | 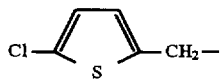 | Me | 5-F | O | CH | 89–90 | |
TABLE 108
| No | R¹ | R² | R³ | X | Y | mp(°C.) | ¹H-NMR(CDCl₃) |
|---|---|---|---|---|---|---|---|
| 769 | 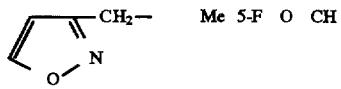 | Me | 5-F | O | CH | | |
| 770 | 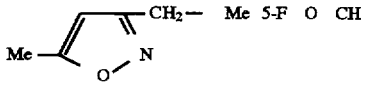 | Me | 5-F | O | CH | 78–81 | 2.38(3H, s), 4.05(3H, s), 4.94(2H, s), 5.59(1H, s), 6.99(1H, dd, J=9.2, 4.3), 7.05(1H, s), 7.17–7.29(3H, m), 7.99(1H, s) |
| 771 | 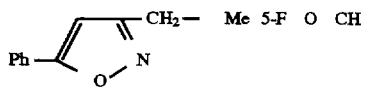 | Me | 5-F | O | CH | | |
| 772 | 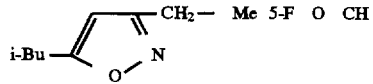 | Me | 5-F | O | CH | | |
| 773 | 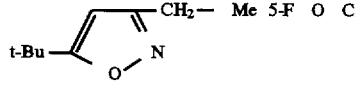 | Me | 5-F | O | CH | | |
| 774 | 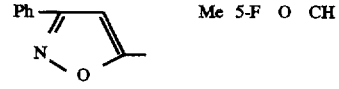 | Me | 5-F | O | CH | | |
| 775 | 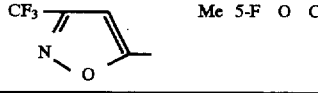 | Me | 5-F | O | CH | | |

TABLE 109

| No | R¹ | R² | R³ | X | Y | mp(°C.) ¹H-NMR(CDCl₃) |
|---|---|---|---|---|---|---|
| 776 | 2-pyridyl-CH₂— | Me | 5-F | O | CH | |
| 777 | 5-Cl-2-pyridyl-CH₂— | Me | 5-F | O | CH | |
| 778 | 2-pyridyl— | Me | 5-F | O | CH | |
| 779 | 5-Cl-2-pyridyl— | Me | 5-F | O | CH | 3.94(3H, s), 6.63(1H, d, J=9.2), 6.93(1H, s), 7.07(1H, s), 7.18–7.29(3H, m), 7.55(1H, dd, J=8.5, 3.1), 7.88(1H, s), 7.96(1H, d, J=2.4) |
| 780 | 3-Cl-2-pyridyl— | Me | 5-F | O | CH | |
| 781 | 3,5-diCl-2-pyridyl— | Me | 5-F | O | CH | 3.93(3H, s), 6.93(1H, s), 7.06(1H, s), 7.18–7.31(3H, m), 7.67(1H, d, J=2.4), 7.83(1H, d, J=2.4), 7.86(1H, s) |
| 782 | 3-CF₃-2-pyridyl— | Me | 5-F | O | CH | |

TABLE 110

| No | R¹ | R² | R³ | X | Y | mp(°C.) ¹H-NMR(CDCl₃) |
|---|---|---|---|---|---|---|
| 783 | 5-CF₃-2-pyridyl— | Me | 5-F | O | CH | 3.91(3H, s), 6.77(1H, d, J=8.6), 6.92(1H, s), 7.05(1H, s), 7.21–7.32(3H, m), 7.82(1H, dd, J=8.6, 2.4), 7.87(1H, s), 8.30(1H, s) |
| 784 | 3-Cl-5-CF₃-2-pyridyl— | Me | 5-F | O | CH | |
| 785 | pyrimidin-2-yl— | Me | 5-F | O | CH | |

TABLE 110-continued
| No | R¹ | R² | R³ | X | Y | mp(°C.) ¹H-NMR(CDCl₃) |
|---|---|---|---|---|---|---|
| 786 | 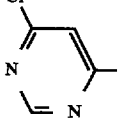 | Me | 5-F | O | CH | |
| 787 | 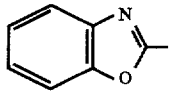 | Me | 5-F | O | CH | |
| 788 | 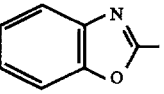 | Me | 5-F | O | CH | |
| 789 | 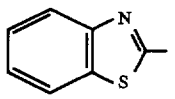 | Me | 5-F | O | CH | |
| 790 | 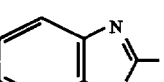 | Me | 5-F | O | CH | |
TABLE 111
| No | R¹ | R² | R³ | X | Y | mp (°C.) | ¹H-NMR (CDCl₃) |
|---|---|---|---|---|---|---|---|
| 791 | 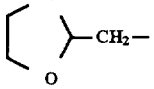 | Me | 5-F | O | CH | | |
| 792 | 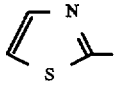 | Me | 5-F | O | CH | | 3.99(3H, s), 6.76(1H, d, J=3.7), 6.99(1H, s), 7.08–7.12(2H, m), 7.21–7.30(2H, m), 7.45(1H, dd, J=8.5, 4.3), 7.95(1H, s) |
| 793 | 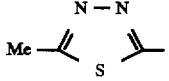 | Me | 5-F | O | CH | | |
| 794 | 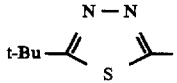 | Me | 5-F | O | CH | | |
| 795 | 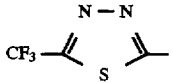 | Me | 5-F | O | CH | | |
| 796 | 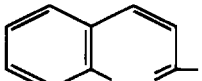 | Me | 5-F | O | CH | | |
| 797 | 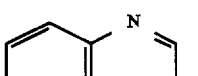 | Me | 5-F | O | CH | | |

TABLE 112

| No | R¹ | R² | R³ | X | Y | mp (°C.) | ¹H-NMR (CDCl₃) |
|----|----|----|----|----|----|----|----|
| 798 | 4-Me, 5-Cl, 6-Me pyrimidin-yl (Me, Cl, Me on pyrimidine) | Me | 5-F | O | CH | | |
| 799 | 4-Et, 5-Cl, 6-Me pyrimidin-yl | Me | 5-F | O | CH | | |
| 800 | 5-Cl, 3-CF₃, 6-Me pyridin-yl | Me | 5-F | O | CH | | |

TABLE 113

| No | R¹ | R² | R³ | X | Y | mp (°C.) | ¹H-NMR (CDCl₃) |
|----|----|----|----|----|----|----|----|
| 801 | 2-Me-C₆H₄-CH₂— | Me | 3-Me | O | CH | | 2.18(3H, s), 2.28(3H, s), 3.98(3H, s), 4.82(2H, s), 6.98(1H, s), 7.11–7.37(8H, m), 7.96(1H, s) |
| 802 | 3-Me-C₆H₄-CH₂— | Me | 3-Me | O | CH | | |
| 803 | 4-Me-C₆H₄-CH₂— | Me | 3-Me | O | CH | | 2.28(3H, s), 2.34(3H, s), 4.00(3H, s), 4.73(2H, s), 7.01–7.36(9H, m), 8.00(1H, s) |
| 804 | 2-F-C₆H₄-CH₂— | Me | 3-Me | O | CH | | |
| 805 | 3-F-C₆H₄-CH₂— | Me | 3-Me | O | CH | | |
| 806 | 4-F-C₆H₄-CH₂— | Me | 3-Me | O | CH | | 2.28(3H, s), 4.00(3H, s), 4.73(2H, s), 6.97–7.37(9H, m), 7.99(1H, s) |
| 807 | 2-Cl-C₆H₄-CH₂— | Me | 3-Me | O | CH | | 2.32(3H, s), 3.96(3H, s), 4.93(2H, s), 7.00(1H, s), 7.12–7.38(8H, m), 7.98(1H, s) |

TABLE 114
| No | R¹ | R² | R³ | X | Y | mp (°C.) | ¹H-NMR (CDCl₃) |
|----|----|----|----|---|---|----------|-----------------|
| 808 | 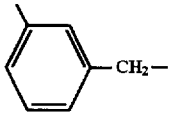 | Me | 3-Me | O | CH | | |
| 809 | 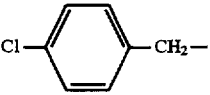 | Me | 3-Me | O | CH | 96–97 | |
| 810 | 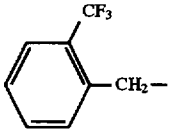 | Me | 3-Me | O | CH | | |
| 811 | 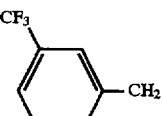 | Me | 3-Me | O | CH | | 2.32(3H, s), 3.98(3H, s), 4.83(2H, s), 7.01(1H, s), 7.13–7.58(8H, m), 7.93(1H, s) |
| 812 | 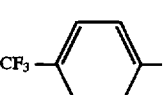 | Me | 3-Me | O | CH | | |
| 813 | 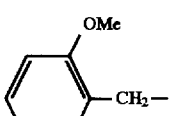 | Me | 3-Me | O | CH | | |
| 814 | 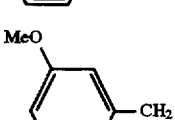 | Me | 3-Me | O | CH | | |
| 815 | 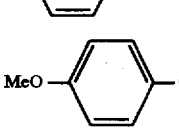 | Me | 3-Me | O | CH | | 2.27(3H, s), 3.80(3H, s), 4.01(3H, s), 4.70(2H, s), 6.82–7.36(9H, m), 8.02(1H, s) |
TABLE 115
| No | R¹ | R² | R³ | X | Y | mp (°C.) | ¹H-NMR (CDCl₃) |
|----|----|----|----|---|---|----------|-----------------|
| 816 | 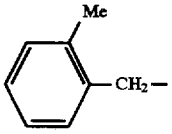 | Me | 4-Me | O | CH | 96–97 | 2.18(3H, s), 2.41(3H, s), 4.00(3H, s), 4.91(2H, s), 6.85–7.37(9H, m), 7.93(1H, s) |
| 817 | 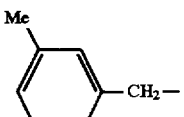 | Me | 4-Me | O | CH | | |

TABLE 115-continued

| No | R¹ | R² | R³ | X | Y | mp (°C.) | ¹H-NMR (CDCl₃) |
|---|---|---|---|---|---|---|---|
| 818 | Me-C₆H₄-CH₂- | Me | 4-Me | O | CH | 117–118 | 2.32(3H, s), 2,39(3H, s), 4.00(3H, s), 4.88(2H, s), 6.80–7.39(9H, m), 7.97(1H, s) |
| 819 | 2-F-C₆H₄-CH₂- | Me | 4-Me | O | CH | | |
| 820 | 3-F-C₆H₄-CH₂- | Me | 4-Me | O | CH | | |
| 821 | 4-F-C₆H₄-CH₂- | Me | 4-Me | O | CH | 90–91 | 2.40(3H, s), 4.01(3H, s), 4.86(2H, s), 6.79(1H, s), 6.88(1H, d, J=7.9), 6.96–7.04(5H, m), 7.22(1H, d, J=1.2), 7.39(1H, d, J=7.9), 7.93(1H, s) |
| 822 | 2-Cl-C₆H₄-CH₂- | Me | 4-Me | O | CH | 103–104 | 2.41(3H, s), 4.03(3H, s), 5.03(2H, s), 6.83(1H, s), 6.88(1H, s), 6.91(1H, s), 7.01(1H, s), 7.14–7.41(5H, m), 8.02(1H, s) |

TABLE 116

| No | R¹ | R² | R³ | X | Y | mp (°C.) | ¹H-NMR (CDCl₃) |
|---|---|---|---|---|---|---|---|
| 823 | 3-Cl-C₆H₄-CH₂- | Me | 4-Me | O | CH | | |
| 824 | 4-Cl-C₆H₄-CH₂- | Me | 4-Me | O | CH | 126–127 | |
| 825 | 2-CF₃-C₆H₄-CH₂- | Me | 4-Me | O | CH | | |
| 826 | 3-CF₃-C₆H₄-CH₂- | Me | 4-Me | O | C | 86–87 | 2.41(3H, s), 4.02(3H, s), 4.96(2H, s), 6.80(1H, s), 6.91(1H, d, J=7.9), 7.01(1H, s), 7.16(1H, d, J=7.9), 7.27–7.44(4H, m), 7.54(1H, d, J=7.9), 7.90(1H, s) |
| 827 | 4-CF₃-C₆H₄-CH₂- | Me | 4-Me | O | CH | | |

TABLE 116-continued

| No | R¹ | R² | R³ | X | Y | mp (°C.) | ¹H-NMR (CDCl₃) |
|---|---|---|---|---|---|---|---|
| 828 | 2-MeO-C₆H₄-CH₂— | Me | 4-Me | O | CH | | |
| 829 | 3-MeO-C₆H₄-CH₂— | Me | 4-Me | O | CH | | |
| 830 | 4-MeO-C₆H₄-CH₂— | Me | 4-Me | O | CH | | 2.39(3H, s), 3.79(3H, s), 4.00(3H, s), 4.84(2H, s), 6.80–6.95(6H, m), 7.02(1H, s), 7.20(1H, t, J=1.2), 7.37(1H, d, J=7.9), 7.95(1H, s) |

TABLE 117

| No | R¹ | R² | R³ | X | Y | mp (°C.) | ¹H-NMR(CDCl₃) |
|---|---|---|---|---|---|---|---|
| 831 | 4-Cl-C₆H₄-CH₂— | Me | 3-Me | O | N | | 2.30(3H, s), 4.03(3H, s), 4.73(2H, s), 7.05–7.40(7H, s), 7.92(1H, s), 8.94(1H, s) |
| 832 | 2,4-diCl-C₆H₃-CH₂— | Me | 3-Me | O | CH | | 2.31(3H, s), 3.96(3H, s), 4.88(2H, s), 7.01(1H, s), 7.13–7.39(7H, m), 7.96(1H, s) |
| 833 | (2-pyridyl)-CH₂— | Me | 3-Me | O | CH | | |
| 834 | (5-Cl-2-thienyl)-CH₂— | Me | 3-Me | O | CH | | |
| 835 | (3-Me-isoxazol-5-yl)-CH₂— | Me | 3-Me | O | CH | | 2.32(3H, s), 2.39(3H, s), 4.04(3H, s), 4.84(2H, s), 5.81(1H, s), 7.03(1H, s)7.13–7.38(4H, s), 8.04(1H, s) |
| 836 | (5-CF₃-2-pyridyl)- | Me | 3-Me | O | CH | | 2.31(3H, s), 3.90(3H, s), 6.72(1H, d, J=8.6), 7.28–7.46(3H, m), 7.81(1H, dd, J=8.6, 2.4), 7.83(1H, s), 8.35(1H, s), 8.80(1H, s) |
| 837 | (5-Cl-2-pyridyl)- | Me | 3-Me | O | CH | | |

TABLE 118

| No | R¹ | R² | R³ | X | Y | mp (°C.) | ¹H-NMR(CDCl₃) |
|---|---|---|---|---|---|---|---|
| 838 | 3-Cl, 5-CF₃-pyridin-2-yl | Me | 3-Me | O | CH | | 2.18(3H, s), 3.87(3H, s), 6.92(1H, t, J=1.2), 7.09(1H, t, J=1.2), 7.22–7.44(3H, m), 7.67(1H, d, J=2.4), 7.80(1H, d, J=1.8), 7.84(1H, s) |
| 839 | 3-CF₃-pyridin-2-yl | Me | 3-Me | O | CH | | |
| 840 | 5-CF₃-pyridin-2-yl | Me | 3-Me | O | CH | | 2.17(3H, s), 3.83(3H, s), 6.83(1H, d, J=8.6), 6.93(1H, s), 7.08(1H, s), 7.25–7.46(3H, m), 7.81(1H, d, J=2.4), 7.84(1H, s), 8.29(1H, s) |
| 841 | 2,3-dichlorobenzyl | Me | 3-Me | O | CH | | 2.30(3H, s), 3.99(3H, s), 4.72(2H, s), 6.96(1H, dd, J=7.9, 1.8), 7.03(1H, s), 7.13–7.46(6H, m), 7.94(1H, s) |
| 842 | PhO(CH₂)₂— | Me | 3-Me | O | CH | | 2.34(3H, s), 3.99(3H, s), 4.01–4.16(4H, m), 6.84(1H, s), 6.86(1H, s), 6.95(1H, t, J=7.3), 7.03(1H, s), 7.09–7.36(6H, m), 8.03(1H, s) |
| 843 | benzothiazol-2-yl | Me | 3-Me | O | CH | | |
| 844 | thiazol-2-yl | Me | 3-Me | O | CH | | |
| 845 | pyrimidin-2-yl | Me | 3-Me | O | CH | | |

TABLE 119

| No | R¹ | R² | R³ | X | Y | mp (°C.) | ¹H-NMR(CDCl₃) |
|---|---|---|---|---|---|---|---|
| 846 | 4-Cl-benzyl | Me | 4-Me | O | N | 155–156 | |
| 847 | 2,4-dichlorobenzyl | Me | 4-Me | O | CH | 129–130 | |
| 848 | pyridin-2-ylmethyl | Me | 4-Me | O | CH | | |

TABLE 119-continued

| No | R¹ | R² | R³ | X | Y | mp (°C.) | ¹H-NMR(CDCl₃) |
|---|---|---|---|---|---|---|---|
| 849 | Cl-[thiophene]-CH₂— | Me | 4-Me | O | CH | | |
| 850 | Me-[isoxazole]-CH₂— | Me | 4-Me | O | CH | 124–125 | |
| 851 | CF₃-[pyridine]- | Me | 4-Me | O | N | 104–105 | |
| 852 | Cl-[pyridine]- | Me | 4-Me | O | CH | | |

TABLE 120

| No | R¹ | R² | R³ | X | Y | mp (°C.) | ¹H-NMR(CDCl₃) |
|---|---|---|---|---|---|---|---|
| 853 | CF₃-[pyridine]-Cl | Me | 4-Me | O | CH | | 2.43(3H, s), 3.89(3H, s), 6.93(1H, s), 7.07–7.34(4H, m), 7.66(1H, d, J=2.4), 7.84(1H, s), 7.85(1H, s) |
| 854 | CF₃-[pyridine]- | Me | 4-Me | O | CH | | |
| 855 | CF₃-[pyridine]- | Me | 4-Me | O | CH | | 2.53(3H, s). 3.87(3H, s), 6.78(1H, d, J=8.6), 6.92(1H, s), 7.06–7.41(4H, m), 7.81(1H, dd, J=9.2, 3.1), 7.86(1H, s), 8.32(1H, s) |
| 856 | Cl,Cl-[phenyl]-CH₂— | Me | 4-Me | O | CH | 130–131 | |
| 857 | [phenyl]-O(CH₂)₂— | Me | 4-Me | O | CH | | 2.40(3H, s), 3.93(2H, t, J=4.9), 4.00(3H, s), 4.15(2H, t, J=4.9), 6.78–7.41(10H, m), 7.86(1H, s) |
| 858 | [benzothiazole]- | Me | 4-Me | O | CH | | |
| 859 | [thiazole]- | Me | 4-Me | O | CH | | |

TABLE 120-continued

| No | R¹ | R² | R³ | X | Y | mp (°C.) | ¹H-NMR(CDCl₃) |
|----|-----|-----|------|---|----|----------|---------------|
| 860 | pyrazinyl | Me | 4-Me | O | CH | | |

TABLE 121

| No | R¹ | R² | R³ | X | Y | mp (°C.) | ¹H—NMR(CDCl₃) |
|----|-----|-----|-----|---|----|----------|---------------|
| 861 | 2-Cl-C₆H₄-OCH₂CH₂— | Me | H | O | CH | | |
| 862 | 3-Cl-C₆H₄-OCH₂CH₂— | Me | H | O | CH | | |
| 863 | 4-Cl-C₆H₄-OCH₂CH₂— | Me | H | O | CH | 103–104 | |
| 864 | 2-Me-C₆H₄-OCH₂CH₂— | Me | H | O | CH | | |
| 865 | 3-Me-C₆H₄-OCH₂CH₂— | Me | H | O | CH | | |
| 866 | 4-Me-C₆H₄-OCH₂CH₂— | Me | H | O | CH | 83–84 | |
| 867 | 2-Cl-C₆H₄-OCH₂CH₂— | Me | H | O | CH | | |

TABLE 122

| No | R¹ | R² | R³ | X | Y | mp (°C.) | ¹H—NMR(CDCl₃) |
|----|-----|-----|-----|---|----|----------|---------------|
| 868 | 3-Cl-C₆H₄-OCH₂CH₂— | Et | H | O | CH | | |

TABLE 122-continued
| No | R¹ | R² | R³ | X | Y | mp (°C.) | ¹H—NMR(CDCl₃) |
|---|---|---|---|---|---|---|---|
| 869 | 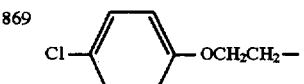 Cl—⟨⟩—OCH₂CH₂— | Et | H | O | CH | 50–54 | |
| 870 | 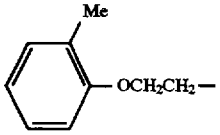 Me / ⟨⟩—OCH₂CH₂— | Et | H | O | CH | | |
| 871 | 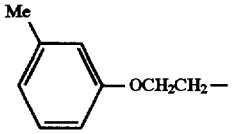 Me—⟨⟩—OCH₂CH₂— | Et | H | O | CH | | |
| 872 | 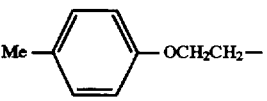 Me—⟨⟩—OCH₂CH₂— | Et | H | O | CH | | 1.35(3H, t, J=7.3), 2.28(3H, s), 3.92(2H, t, J=4.9), 4.16(2H, t, J=4.9), 4.27(2H, q, J=7.3), 6.70–7.53(10H, m), 7.93(1H, s) |
| 873 | 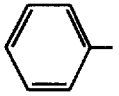 ⟨⟩— | Me | H | S | N | | |
| 874 | 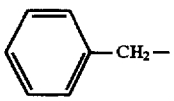 ⟨⟩—CH₂— | Me | H | S | N | | 3.94(2H, s), 4.08(3H, s), 7.11–7.52(9H, m), 9.17(1H, s) |
| 875 | 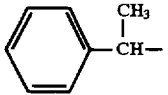 ⟨⟩—CH(CH₃)— | Me | H | S | N | | |
TABLE 123
| No | R¹ | R² | R³ | X | Y | mp (°C.) | ¹H—NMR(CDCl₃) |
|---|---|---|---|---|---|---|---|
| 876 | 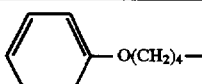 ⟨⟩—O(CH₂)₄— | Et | H | O | CH | | 1.35(3H, t, J=7.3), 1.58–1.71(4H, m), 3.85–3.92(4H, m), 4.29(2H, q, J=7.3), 6.84–7.51(11H, m), 7.97(1H, s) |
| 877 | 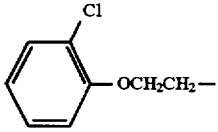 Cl / ⟨⟩—OCH₂CH₂— | Me | 5-Cl | O | CH | | |
| 878 | 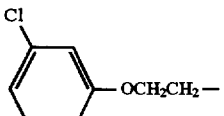 Cl / ⟨⟩—OCH₂CH₂— | Me | 5-Cl | O | CH | | |
| 879 | 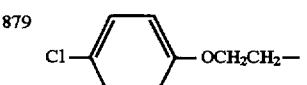 Cl—⟨⟩—OCH₂CH₂— | Me | 5-Cl | O | CH | | |

TABLE 123-continued

| No | R¹ | R² | R³ | X | Y | mp (°C.) | ¹H—NMR(CDCl₃) |
|---|---|---|---|---|---|---|---|
| 880 | 2-Me-C₆H₄-OCH₂CH₂— | Me | 5-Cl | O | CH | | |
| 881 | 3-Me-C₆H₄-OCH₂CH₂— | Me | 5-Cl | O | CH | | |
| 882 | 4-Me-C₆H₄-OCH₂CH₂— | Me | 5-Cl | O | CH | | |

TABLE 124

| No | R¹ | R² | R³ | X | Y | mp (°C.) | ¹H—NMR(CDCl₃) |
|---|---|---|---|---|---|---|---|
| 883 | 2-Cl-C₆H₄-OCH₂CH₂— | Me | 5-F | O | CH | | |
| 884 | 3-Cl-C₆H₄-OCH₂CH₂— | Me | 5-F | O | CH | | |
| 885 | 4-Cl-C₆H₄-OCH₂CH₂— | Me | 5-F | O | CH | 104–106 | |
| 886 | 2-Me-C₆H₄-OCH₂CH₂— | Me | 5-F | O | CH | | |
| 887 | 3-Me-C₆H₄-OCH₂CH₂— | Me | 5-F | O | CH | | |
| 888 | 4-Me-C₆H₄-OCH₂CH₂— | Me | 5-F | O | CH | 103.5–104.5 | |
| 889 | C₆H₅-O(CH₂)₄— | Me | 5-F | O | CH | 66.5–68 | |

TABLE 124-continued

| No | R¹ | R² | R³ | X | Y | mp (°C.) | ¹H—NMR(CDCl₃) |
|---|---|---|---|---|---|---|---|
| 890 | ⌬—(CH₂)₃— | Me | 5-F | O | CH | | |

TABLE 125

| No | R¹ | R² | R³ | X | Y | mp (°C.) | ¹H—NMR(CDCl₃) |
|---|---|---|---|---|---|---|---|
| 891 | 2-Cl-C₆H₄—OCH₂CH₂— | Me | 5-Me | O | CH | | |
| 892 | 3-Cl-C₆H₄—OCH₂CH₂— | Me | 5-Me | O | CH | | |
| 893 | 4-Cl-C₆H₄—OCH₂CH₂— | Me | 5-Me | O | CH | | |
| 894 | 2-Me-C₆H₄—OCH₂CH₂— | Me | 5-Me | O | CH | | |
| 895 | 3-Me-C₆H₄—OCH₂CH₂— | Me | 5-Me | O | CH | | |
| 896 | 4-Me-C₆H₄—OCH₂CH₂— | Me | 5-Me | O | CH | | |
| 897 | C₆H₅—O(CH₂)₂— | Me | 5-Me | O | CH | | 2.35(3H, s), 3.93(2H, t, J=4.9), 4.01(3H, s), 4.14(2H, t, J=4.9), 6.82–7.32(10H, m), 7.88(1H, s) |

TABLE 126

| No | R¹ | R² | R³ | X | Y | mp (°C.) | ¹H—NMR(CDCl₃) |
|---|---|---|---|---|---|---|---|
| 898 | C₆H₅—O(CH₂)₃— | Me | 5-Me | O | CH | | |

TABLE 126-continued

| No | R¹ | R² | R³ | X | Y | mp (°C.) | ¹H—NMR(CDCl₃) |
|----|-----|-----|------|---|----|----------|---------------|
| 899 | (phenyl)-O(CH₂)₄— | Me | 5-Me | O | CH | | |
| 900 | Me-(phenyl)-CH₂— | Me | 6-Me | O | CH | | |
| 901 | F-(phenyl)-CH₂— | Me | 6-Me | O | CH | | |
| 902 | Cl-(phenyl)-CH₂— | Me | 6-Me | O | CH | | 2.30(3H, s), 4.04(3H, s), 4.95(2H, s), 6.77–7.34(9H, m), 8.08(1H, s) |
| 903 | (phenyl)-CH(CH₃)— | Me | 6-Me | O | CH | | |
| 904 | CF₃-(pyridyl)— | Me | 6-Me | O | CH | | |
| 905 | Cl-(pyridyl)— | Me | 6-Me | O | CH | | |

TABLE 127

| No | R¹ | R² | R³ | X | Y | mp (°C.) | ¹H—NMR(CDCl₃) |
|----|-----|-----|------|---|----|----------|---------------|
| 906 | Cl-(pyridyl)— | Me | H | O | CH | | 3.92(3H, s), 6.62(1H, d, J = 7.9), 6.94(1H, d, J = 7.9), 6.97(1H, d, 7.3), 7.12(1H, s), 7.29–7.57(5H, m), 7.94(1H, s) |
| 907 | Cl-(pyridyl)— | Me | 5-Cl | O | CH | | |
| 908 | Cl-(pyridyl)— | Me | 5-F | O | CH | | |
| 909 | Cl-(pyridyl)— | Me | 5-Me | O | CH | | |

TABLE 127-continued

| No  | R¹ | R² | R³ | X | Y | mp (°C.) | ¹H—NMR(CDCl₃) |
|-----|----|----|----|---|---|----------|----------------|
| 910 | 6-chloro-3-pyridyl | Et | H | O | CH | | 1.27(3H, t, J = 7.3), 4.17(2H, q, J = 7.3), 6.61(1H, d, J = 8.5), 6.92–7.57(8H, m), 7.98(1H, s) |
| 911 | 6-chloro-3-pyridyl | n-Pr | H | O | CH | | |
| 912 | 6-chloro-3-pyridyl | i-Pr | H | O | CH | | |

TABLE 128

| No  | R¹ | R² | R³ | X | Y | mp (°C.) | ¹H—NMR(CDCl₃) |
|-----|----|----|----|---|---|----------|----------------|
| 913 | Ph-CH(CH₃)– | Me | 5-Me | O | CH | | 1.29(3H, d, J = 6.7), 2.28(3H, s), 4.06(3H, s), 5.10(1H, q, J = 6.7), 6.60(1H, d, J = 8.5), 7.05–7.31(9H, m), 7.98(1H, s) |
| 914 | Ph-CH(Et)– | Me | 5-Me | O | CH | | 0.71(3H, t, J = 7.3), 1.53–1.67(2H, m), 2.26(3H, s), 4.07(3H, s), 4.87(1H, t, J = 7.3), 6.56(1H, d, J = 8.5), 7.01–7.30(9H, m), 8.01(1H, s) |
| 915 | Ph-O(CH₂)₃– | Me | 5-F | O | CH | | |
| 916 | Ph-CH(CH₃)– | Me | 5-Cl | O | CH | | 1.30(3H, d, J = 6.1), 4.07(3H, s), 5.09(1H, q, J = 6.7), 6.64(1H, d, J = 9.2), 7.03–7.36 (8H, m), 7.48(1H, d, J = 3.1), 8.03(1H, s) |
| 917 | Ph-CH(Et)– | Me | 5-Cl | O | CH | | 0.71(3H, t, J = 7.9), 1.57–1.67(2H, m), 4.08(3H, s), 4.87(1H, t, J = 6.1), 6.61(1H, d, J = 8.5), 7.06–7.32(8H, m), 7.46(1H, d, J = 3.1), 8.01(1H, s) |
| 918 | Ph-CH₂CH₂– | Me | 5-Me | O | CH | | |
| 919 | Ph-O(CH₂)₃– | Me | 5-Me | O | CH | | |
| 920 | 5-chloro-2-pyridyl | Me | 5-Me | O | CH | | 2.40(3H, s), 3.92(3H, s), 6.63(1H, d, J = 8.5), 6.92(1H, s), 7.10–7.55(5H, m), 7.88(1H, s), 7.97(1H, d, J = 2.4) |

TABLE 129
| No | R¹ | R² | R³ | X | Y | mp (°C.) | ¹H—NMR(CDCl₃) |
|---|---|---|---|---|---|---|---|
| 921 | 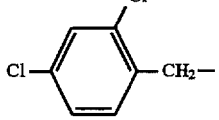 | Me | 5-MeO | O | CH | 120.0–121.0 | |
| 922 | 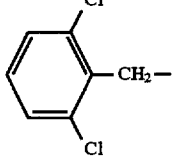 | Me | 5-MeO | O | CH | | |
| 923 | 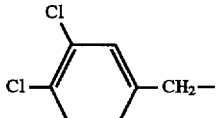 | Me | 5-MeO | O | CH | | |
| 924 | 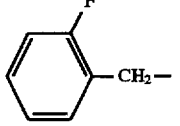 | Me | 5-MeO | O | CH | | |
| 925 | 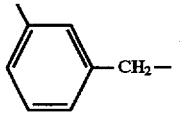 | Me | 5-MeO | O | CH | | |
| 926 | 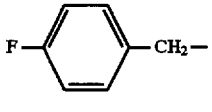 | Me | 5-MeO | O | CH | 102.5–103.5 | |
| 927 | 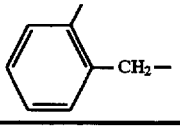 | Me | 5-MeO | O | CH | | |
TABLE 130
| No | R¹ | R² | R³ | X | Y | mp (°C.) | ¹H—NMR(CDCl₃) |
|---|---|---|---|---|---|---|---|
| 928 | 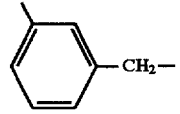 | Me | 5-MeO | O | CH | | |
| 929 | 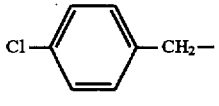 | Me | 5-MeO | O | CH | 104–105 | |

TABLE 130-continued

| No | R¹ | R² | R³ | X | Y | mp (°C.) | ¹H—NMR(CDCl₃) |
|---|---|---|---|---|---|---|---|
| 930 | 2-MeO-C₆H₄-CH₂— | Me | 5-MeO | O | CH | | |
| 931 | 3-MeO-C₆H₄-CH₂— | Me | 5-MeO | O | CH | | |
| 932 | 4-MeO-C₆H₄-CH₂— | Me | 5-MeO | O | CH | | |
| 933 | 2-Me-C₆H₄-CH₂— | Me | 5-MeO | O | CH | | |
| 934 | 3-Me-C₆H₄-CH₂— | Me | 5-MeO | O | CH | | |
| 935 | 4-Me-C₆H₄-CH₂— | Me | 5-MeO | O | CH | 101–102 | |

TABLE 131

| No | R¹ | R² | R³ | X | Y | mp (°C.) | ¹H—NMR(CDCl₃) |
|---|---|---|---|---|---|---|---|
| 936 | 2-Cl-pyridin-6-yl— | Me | 5-MeO | O | CH | | |
| 937 | 5-Cl-pyridin-2-yl— | Me | 5-MeO | O | CH | | 3.84(3H, s), 3.92(3H, s), 6.61(1H, d, J = 8.5), 6.92–7.23(5H, m), 7.53(1H, dd, J = 3.0, 9.2), 7.89(1H, s), 7.97(1H, d, J = 2.4) |
| 938 | 5-CF₃-pyridin-2-yl— | Me | 5-MeO | O | CH | | 3.85(3H, s), 3.89(3H, s), 6.76(1H, d, J = 8.5), 6.91(1H, s), 7.02–7.91(4H, s), 7.79(1H, dd, J = 2.4, 8.5), 8.31(1H, s) |
| 939 | thiophen-2-yl-CH₂— | Me | 5-MeO | O | CH | | |
| 940 | 5-Cl-thiophen-2-yl-CH₂— | Me | 5-MeO | O | CH | | 3.81(3H, s), 4.04(3H, s), 4.91(2H, s), 6.62(1H, d, J = 3.7), 6.73(1H, d, J = 7.3), 6.91–7.03(4H, m), 7.18(1H, s), 7.98(1H, s) |

TABLE 131-continued
| No | R¹ | R² | R³ | X | Y | mp (°C.) | ¹H—NMR(CDCl₃) |
|---|---|---|---|---|---|---|---|
| 941 |  | Me | 5-MeO | O | CH | | |
| 642 | 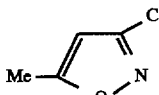 | M3 | 5-MeO | O | CH | | |
TABLE 132
| No | R¹ | R² | R³ | X | Y | mp (°C.) | ¹H—NMR(CDCl₃) |
|---|---|---|---|---|---|---|---|
| 943 | 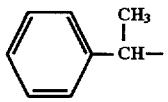 | Me | 5-MeO | O | CH | 76.5–77.5 | |
| 944 | 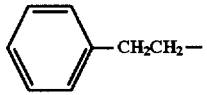 | Me | 5-MeO | O | CH | | |
| 945 | 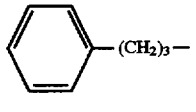 | Me | 5-MeO | O | CH | | |
| 946 | 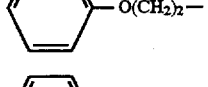 | Me | 5-MeO | O | CH | 60.5–61.5 | |
| 947 | 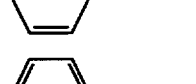 | Me | 5-MeO | O | CH | | |
| 948 |  | Me | 5-MeO | O | CH | | |
| 949 | 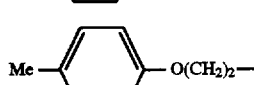 | Me | 5-MeO | O | CH | | |
| 950 |  | Me | 5-MeO | O | CH | | |

TABLE 133
| No | R¹ | R² | R³ | X | Y | mp (°C.) | ¹H—NMR(CDCl₃) |
|----|----|----|----|----|----|----------|----------------|
| 951 | 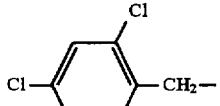 2,4-dichlorobenzyl | Et | 5-MeO | O | CH | 100.5–101.5 | |
| 952 | 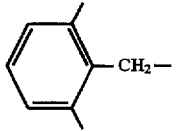 2,6-dichlorobenzyl | Et | 5-MeO | O | CH | | |
| 953 | 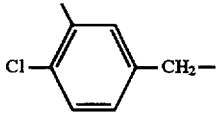 3,4-dichlorobenzyl | Et | 5-MeO | O | CH | | |
| 954 | 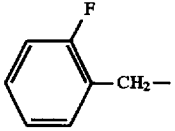 2-fluorobenzyl | Et | 5-MeO | O | CH | | |
| 955 | 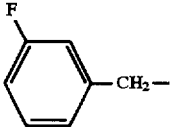 3-fluorobenzyl | Et | 5-MeO | O | CH | | |
| 956 | 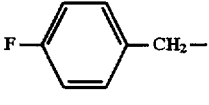 4-fluorobenzyl | Et | 5-MeO | O | CH | 67–68 | |
| 957 | 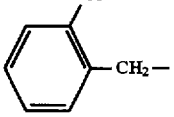 2-chlorobenzyl | Et | 5-MeO | O | CH | | |
TABLE 134
| No | R¹ | R² | R³ | X | Y | mp (°C.) | ¹H—NMR(CDCl₃) |
|----|----|----|----|----|----|----------|----------------|
| 958 | 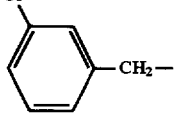 3-chlorobenzyl | Et | 5-MeO | O | CH | | |
| 959 | 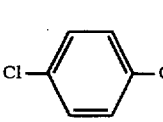 4-chlorobenzyl | Et | 5-MeO | O | CH | 87–88 | |

TABLE 134-continued
| No | R¹ | R² | R³ | X | Y | mp (°C.) | ¹H—NMR(CDCl₃) |
|---|---|---|---|---|---|---|---|
| 960 | 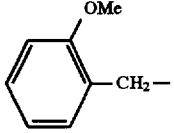 (2-OMe-benzyl) | Et | 5-MeO | O | CH | | |
| 961 | 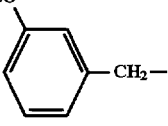 (3-MeO-benzyl) | Et | 5-MeO | O | CH | | |
| 962 |  (4-MeO-benzyl) | Et | 5-MeO | O | CH | | |
| 963 | 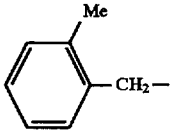 (2-Me-benzyl) | Et | 5-MeO | O | CH | | |
| 964 | 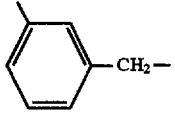 (3-Me-benzyl) | Et | 5-MeO | O | CH | | |
| 965 | 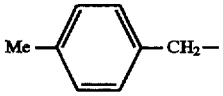 (4-Me-benzyl) | Et | 5-MeO | O | CH | 60–62 | |
TABLE 135
| No | R¹ | R² | R³ | X | Y | mp (°C.) | ¹H—NMR(CDCl₃) |
|---|---|---|---|---|---|---|---|
| 966 | 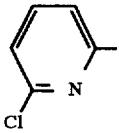 | Et | 5-MeO | O | CH | | |
| 967 | 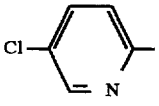 | Et | 5-MeO | O | CH | | 1.25(3H, t, J = 7.3), 3.84(3H, s), 4.16(2H, q, J = 7.3), 6.62(1H, d, J = 8.5), 6.92(1H, s), 7.00–7.16(4H, m), 7.53(1H, dd, J = 3.1, 9.2), 7.94(1H, s), 7.97(1H, d, J = 2.4) |
| 968 | 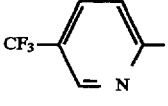 | Et | 5-MeO | O | CH | | 1.21(3H, t, J = 7.3), 3.85(3H, s), 4.13(2H, q, J = 7.3), 6.76(1H, d, J = 8.5), 6.91(1H, s), 7.00–7.19(4H, m), 7.78(1H, dd, J = 2.4, 6.1), 7.94(1H, s), 7.97(1H, d, J = 2.4) |
| 969 | 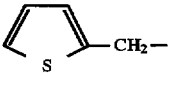 | Et | 5-MeO | O | CH | | |
| 970 | 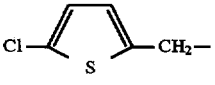 | Et | 5-MeO | O | CH | | 1.37(3H, t, J = 6.7), 3.81(3H, s), 4.29(2H, q, J = 6.7), 4.92(2H, s), 6.62(1H, d, J = 3.7), 6.73(1H, d, J = 3.7), 6.91–6.98(4H, m), 7.18(1H, d, J = 1.2), 8.02(1H, s) |

TABLE 135-continued
| No | R¹ | R² | R³ | X | Y | mp (°C.) | ¹H—NMR(CDCl₃) |
|----|-----|-----|------|---|----|----------|----------------|
| 971 | 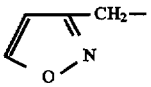 | Et | 5-MeO | O | CH | | |
| 972 | 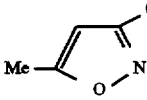 | Et | 5-MeO | O | CH | | |
TABLE 136
| No | R¹ | R² | R³ | X | Y | mp(°C.) | ¹H-NMR(CDCl₃) |
|----|-----|-----|------|---|----|---------|----------------|
| 973 | 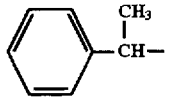 | Et | 5-MeO | O | CH | 73–74 | |
| 974 | 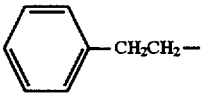 | Et | 5-MeO | O | CH | | |
| 975 | 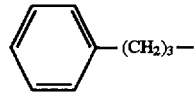 | Et | 5-MeO | O | CH | | |
| 976 | 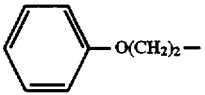 | Et | 5-MeO | O | CH | | 1.37(3H, t, J=7.3), 3.82(3H, s), 3.93(2H, t, J=4.3), 4.11(2H, t, J=4.3), 4.27(2H, q, J=7.3), 6.80–7.31(10H, m), 7.95(1H, s) |
| 977 | 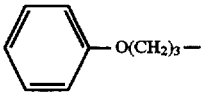 | Et | 5-MeO | O | CH | | |
| 978 | 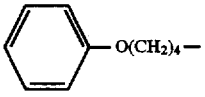 | Et | 5-MeO | O | CH | | |
| 979 | 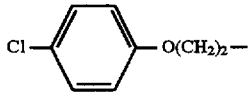 | Et | 5-MeO | O | CH | | |
| 980 | 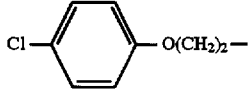 | Et | 5-MeO | O | CH | | |

TABLE 137
| No | R¹ | R² | R³ | X | Y | mp(°C.) | ¹H-NMR(CDCl₃) |
|----|----|----|----|----|----|---------|---------------|
| 981 | 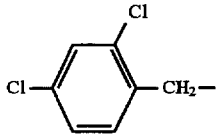 | Et | 5-Me | O | CH | | |
| 982 | 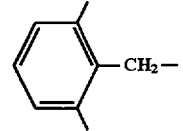 | Et | 5-Me | O | CH | | |
| 983 | 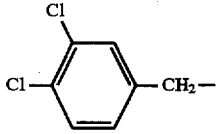 | Et | 5-Me | O | CH | | |
| 984 | 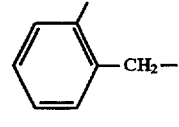 | Et | 5-Me | O | CH | | |
| 985 | 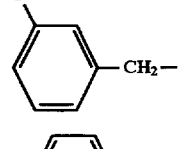 | Et | 5-Me | O | CH | | |
| 986 | 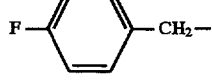 | Et | 5-Me | O | CH | 109–110 | |
| 987 | 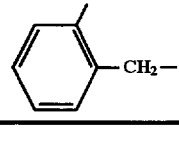 | Et | 5-Me | O | CH | | |
TABLE 138
| No | R¹ | R² | R³ | X | Y | mp(°C.) | ¹H-NMR(CDCl₃) |
|----|----|----|----|----|----|---------|---------------|
| 988 | 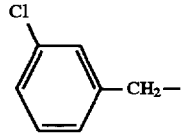 | Et | 5-Me | O | CH | | |
| 989 | 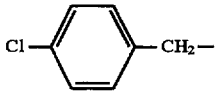 | Et | 5-Me | O | CH | 112–113 | |

TABLE 138-continued

| No | R¹ | R² | R³ | X | Y | mp(°C.) | ¹H-NMR(CDCl₃) |
|---|---|---|---|---|---|---|---|
| 990 | 2-OMe-C₆H₄-CH₂- | Et | 5-Me | O | CH | | |
| 991 | 3-MeO-C₆H₄-CH₂- | Et | 5-Me | O | CH | | |
| 992 | 4-MeO-C₆H₄-CH₂- | Et | 5-Me | O | CH | | |
| 993 | 2-Me-C₆H₄-CH₂- | Et | 5-Me | O | CH | | |
| 994 | 3-Me-C₆H₄-CH₂- | Et | 5-Me | O | CH | | |
| 995 | 4-Me-C₆H₄-CH₂- | Et | 5-Me | O | CH | 105.5–107 | |

TABLE 139

| No | R¹ | R² | R³ | X | Y | mp(°C.) | ¹H-NMR(CDCl₃) |
|---|---|---|---|---|---|---|---|
| 996 | 2-Cl-pyridin-6-yl | Et | 5-Me | O | CH | | |
| 997 | 4-Cl-pyridin-6-yl | Et | 5-Me | O | CH | | 1.25(3H, t, J=6.7), 2.39(3H, s), 4.17(2H, q, J=6.7), 6.62(1H, d, J=8.5), 6.91 (1H, s), 7.09–7.35(4H, m), 7.53(1H, dd, J=2.4, 8.5), 7.93(1H, s, 7.98(1H, d, J=2.4) |
| 998 | 4-CH₃-pyridin-6-yl | Et | 5-Me | O | CH | | 1.22(3H, t, J=6.7), 2.41(3H, s), 4.13(2H, q, J=6.7), 6.74–7.37(6H, m), 7.91 (1H, s), 8.31(1H, s) |
| 999 | thiophen-2-yl-CH₂- | Et | 5-Me | O | CH | | |
| 1000 | 5-Cl-thiophen-2-yl-CH₂- | Et | 5-Me | O | CH | 88–89 | |

TABLE 139-continued
| No | R¹ | R² | R³ | X | Y | mp(°C.) | ¹H-NMR(CDCl₃) |
|---|---|---|---|---|---|---|---|
| 1001 | 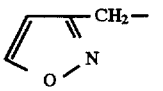—CH₂— | Et | 5-Me | O | CH | | |
| 1002 | 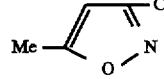—CH₂— | Et | 5-Me | O | CH | | |
TABLE 140
| No | R¹ | R² | R³ | X | Y | mp(°C.) | ¹H-NMR(CDCl₃) |
|---|---|---|---|---|---|---|---|
| 1003 | 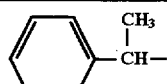 | Et | 5-Me | O | CH | | 1.29(3H, d, J=6.7), 1.39(3H, t, J=6.7), 2.27(3H, s), 4.32(2H, q, J=6.7), 5.08(1H, q, J=6.7), 6.61(1H, d, J=8.5), 7.04–7.34(9H, m), 8.03(1H, s) |
| 1004 | 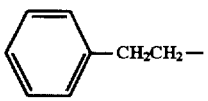—CH₂CH₂— | Et | 5-Me | O | CH | | |
| 1005 | 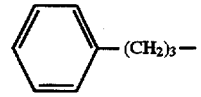—(CH₂)₃— | Et | 5-Me | O | CH | | |
| 1006 | 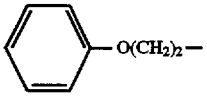—O(CH₂)₂— | Et | 5-Me | O | CH | 63–64.5 | |
| 1007 | 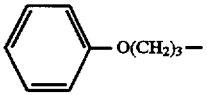—O(CH₂)₃— | Et | 5-Me | O | CH | | |
| 1008 | 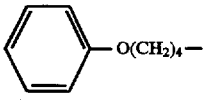—O(CH₂)₄— | Et | 5-Me | O | CH | | |
| 1009 | 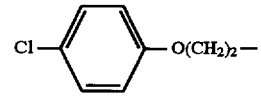—O(CH₂)₂— | Et | 5-Me | O | CH | | |
| 1010 | 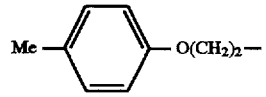—O(CH₂)₂— | Et | 5-Me | O | CH | | |
TABLE 141
| No | R¹ | R² | R³ | X | Y | mp(°C.) | ¹H-NMR(CDCl₃) |
|---|---|---|---|---|---|---|---|
| 1011 | 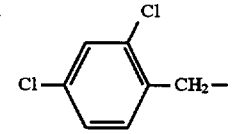 | Et | 5-F | O | CH | | |

TABLE 141-continued
| No | R¹ | R² | R³ | X | Y | mp(°C.) | ¹H-NMR(CDCl₃) |
|---|---|---|---|---|---|---|---|
| 1012 | 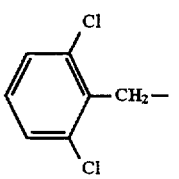 2,6-diCl-benzyl | Et | 5-F | O | CH | | |
| 1013 | 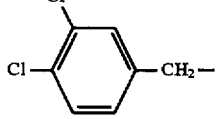 3,4-diCl-benzyl | Et | 5-F | O | CH | | |
| 1014 | 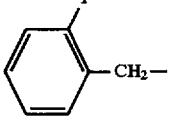 2-F-benzyl | Et | 5-F | O | CH | | |
| 1015 | 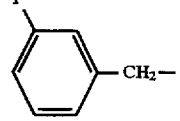 3-F-benzyl | Et | 5-F | O | CH | | |
| 1016 | 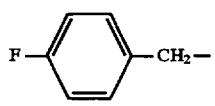 4-F-benzyl | Et | 5-F | O | CH | | 1.36(3H, t, J=6.7), 4.28(2H, q, J=6.7), 4.85(2H, s), 6.89–7.28(9H, m), 7.99(1H, s) |
| 1017 | 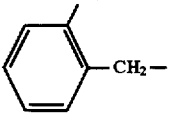 2-Cl-benzyl | Et | 5-F | O | CH | | |
TABLE 142
| No | R¹ | R² | R³ | X | Y | mp(°C.) | ¹H-NMR(CDCl₃) |
|---|---|---|---|---|---|---|---|
| 1018 | 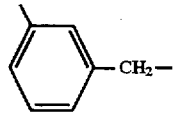 3-Cl-benzyl | Et | 5-F | O | CH | | |
| 1019 | 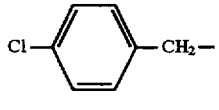 4-Cl-benzyl | Et | 5-F | O | CH | | 1.36(3H, t, J=6.7), 4.28(2H, q, J=6.7), 4.86(2H, s), 6.88–7.65(9H, m), 8.00(1H, s) |
| 1020 | 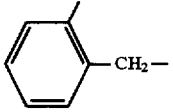 2-OMe-benzyl | Et | 5-F | O | CH | | |

TABLE 142-continued

| No | R¹ | R² | R³ | X | Y | mp(°C.) | ¹H-NMR(CDCl₃) |
|---|---|---|---|---|---|---|---|
| 1021 | 4-MeO-C₆H₄-CH₂- | Et | 5-F | O | CH | | |
| 1022 | 4-MeO-C₆H₄-CH₂- | Et | 5-F | O | CH | | |
| 1023 | 2-Me-C₆H₄-CH₂- | Et | 5-F | O | CH | | |
| 1024 | 3-Me-C₆H₄-CH₂- | Et | 5-F | O | CH | | |
| 1025 | 4-Me-C₆H₄-CH₂- | Et | 5-F | O | CH | | 1.36(3H, t, J=6.7), 2.32(3H, s), 4.28(2H, q, J=6.7), 4.86(2H, s), 6.90–7.25(9H, m), 8.03(1H, s) |

TABLE 143

| No | R¹ | R² | R³ | X | Y | mp(°C.) | ¹H-NMR(CDCl₃) |
|---|---|---|---|---|---|---|---|
| 1026 | 2-Cl-pyridin-6-yl | Et | 5-F | O | CH | | |
| 1027 | 4-Cl-pyridin-2-yl | Et | 5-F | O | CH | | 1.26(3H, t, J=6.7), 4.18(2H, q, J=6.7), 6.62(1H, d, J=8.5), 6.93(1H, s), 7.07(1H, s), 7.21–7.28(3H, m), 7.55(1H, dd, J=8.6, 2.4), 7.91(1H, s), 7.96(1H, d, J=3.1) |
| 1028 | 4-CF₃-pyridin-2-yl | Et | 5-F | O | CH | | 1.23(3H, t, J=6.7), 4.15(2H, q, J=6.7), 6.77(1H, d, J=8.6), 6.92(1H, s), 7.06(1H, s), 7.24–7.27(3H, m), 7.81(1H, dd, J=8.6, 2.4), 7.90(1H, s), 8.30(1H, s) |
| 1029 | thiophen-2-yl-CH₂- | Et | 5-F | O | CH | | |
| 1030 | 5-Cl-thiophen-2-yl-CH₂- | Et | 5-F | O | CH | | 1.37(3H, t, J=6.7), 4.29(2H, q, J=6.7), 4.94(2H, s), 6.62–7.26(7H, m), 8.00(1H, s) |
| 1031 | isoxazol-3-yl-CH₂- | Et | 5-F | O | CH | | |

TABLE 143-continued

| No | R¹ | R² | R³ | X | Y | mp(°C.) | ¹H-NMR(CDCl₃) |
|---|---|---|---|---|---|---|---|
| 1032 | Me-[isoxazole]-CH₂— | Et | 5-F | O | CH | | |

TABLE 144

| No | R¹ | R² | R³ | X | Y | mp(°C.) | ¹H-NMR(CDCl₃) |
|---|---|---|---|---|---|---|---|
| 1033 | Ph-CH(CH₃)— | Et | 5-F | O | CH | | 1.29(3H, d, J=6.1), 1.40(3H, t, J=6.7), 4.32(2H, q, J=6.7), 5.07(1H, J=6.1), 6.64(1H, dd, J=9.2, 4.3), 6.94–7.33(9H, m), 8.03(1H, s) |
| 1034 | Ph-CH₂CH₂— | Et | 5-F | O | CH | | |
| 1035 | Ph-(CH₂)₃— | Et | 5-F | O | CH | | |
| 1036 | Ph-O(CH₂)₂— | Et | 5-F | O | CH | | 1.35(3H, t, J=7.3), 3.91–3.94(2H, m), 4.12–4.15(2H, m), 4.27(2H, q, J=7.3) 6.81–7.31(10H, m), 7.92(1H, s) |
| 1037 | Ph-O(CH₂)₃— | Et | 5-F | O | CH | | |
| 1038 | Ph-O(CH₂)₄— | Et | 5-F | O | CH | | |
| 1039 | Cl-C₆H₄-O(CH₂)₂— | Et | 5-F | O | CH | | |
| 1040 | Me-C₆H₄-O(CH₂)₂— | Et | 5-F | O | CH | | |

TABLE 145

| No | R¹ | R² | R³ | X | Y | mp(°C.) | ¹H-NMR(CDCl₃) |
|---|---|---|---|---|---|---|---|
| 1041 | 2-Cl,4-Cl-C₆H₃-CH₂— | Et | 5-Cl | O | CH | 117–118 | |

TABLE 145-continued
| No | R¹ | R² | R³ | X | Y | mp(°C.) | ¹H-NMR(CDCl₃) |
|---|---|---|---|---|---|---|---|
| 1042 | 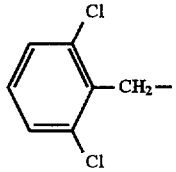 | Et | 5-Cl | O | CH | | |
| 1043 | 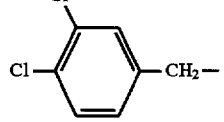 | Et | 5-Cl | O | CH | | |
| 1044 | 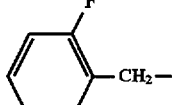 | Et | 5-Cl | O | CH | | |
| 1045 | 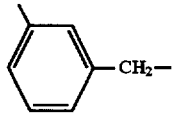 | Et | 5-Cl | O | CH | | |
| 1046 | 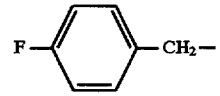 | Et | 5-Cl | O | CH | 102.5–103.5 | |
| 1047 | 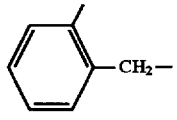 | Et | 5-Cl | O | CH | | |
TABLE 146
| No | R¹ | R² | R³ | X | Y | mp(°C.) | ¹H-NMR(CDCl₃) |
|---|---|---|---|---|---|---|---|
| 1048 | 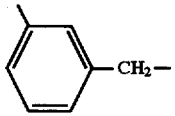 | Et | 5-Cl | O | CH | | |
| 1049 | 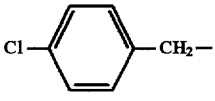 | Et | 5-Cl | O | CH | 131–132 | |
| 1050 | 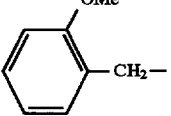 | Et | 5-Cl | O | CH | | |

TABLE 146-continued

| No | R¹ | R² | R³ | X | Y | mp(°C.) | ¹H-NMR(CDCl₃) |
|---|---|---|---|---|---|---|---|
| 1051 | 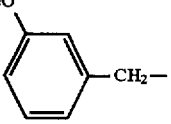 MeO—⟨phenyl⟩—CH₂— (3-MeO benzyl) | Et | 5-Cl | O | CH | | |
| 1052 | 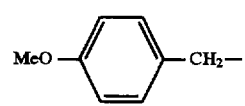 MeO—⟨phenyl⟩—CH₂— (4-MeO benzyl) | Et | 5-Cl | O | CH | | |
| 1053 | 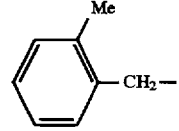 2-Me-benzyl | Et | 5-Cl | O | CH | | |
| 1054 | 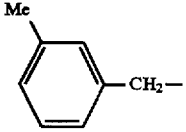 3-Me-benzyl | Et | 5-Cl | O | CH | | |
| 1055 | 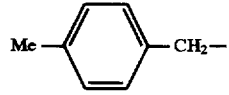 4-Me-benzyl | Et | 5-Cl | O | CH | 116.5–117.5 | |

TABLE 147

| No | R¹ | R² | R³ | X | Y | mp(°C.) | ¹H-NMR(CDCl₃) |
|---|---|---|---|---|---|---|---|
| 1056 | 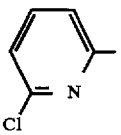 2-Cl-pyridyl | Et | 5-Cl | O | CH | | |
| 1057 | 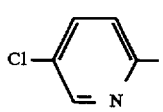 4-Cl-pyridyl | Et | 5-Cl | O | CH | | 1.27(3H, t, J=7.3), 4.19(2H, q, J=7.3), 6.62(1H, d, J=8.5), 6.93(1H, s), 7.08(1H, s), 7.18(1H, d, J=8.5), 7.47–7.58(3H, m), 7.92(1H, s), 7.97(1H, d, J=2.4) |
| 1058 | 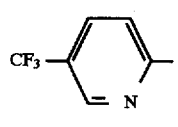 4-CF₃-pyridyl | Et | 5-Cl | O | CH | | 1.24(3H, t, J=6.7), 4.17(2H, q, J=6.7), 6.77(1H, d, J=8.6), 6.92(1H, s), 7.06(1H, s), 7.20–7.54(3H, m), 7.82(1H, dd, J=8.6, 2.4), 7.91 (1H, s), 8.30(1H, d, J=2.4) |
| 1059 | 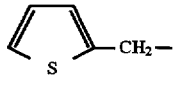 thienyl-CH₂— | Et | 5-Cl | O | CH | | |
| 1060 | 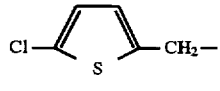 Cl-thienyl-CH₂— | Et | 5-Cl | O | CH | 98–99 | |
| 1061 | 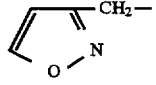 isoxazolyl-CH₂— | Et | 5-Cl | O | CH | | |

TABLE 147-continued

| No | R¹ | R² | R³ | X | Y | mp(°C.) | ¹H-NMR(CDCl₃) |
|---|---|---|---|---|---|---|---|
| 1062 | Me-[isoxazole]-CH₂— | Et | 5-Cl | O | CH | | |

TABLE 148

| No | R¹ | R² | R³ | X | Y | mp(°C.) | ¹H-NMR(CDCl₃) |
|---|---|---|---|---|---|---|---|
| 1063 | Ph-CH(CH₃)— | Me | 5-Cl | O | CH | | 1.30(3H, d, J=6.7), 1.40(3H, t, J=7.3), 4.32(2H, q, J=7.3), 5.10(1H, q, J=6.7), 6.64(1H, d, J=8.6), 7.07–7.65(9H, m), 8.03(1H, s) |
| 1064 | Ph-CH₂CH₂— | Me | 5-Cl | O | CH | | |
| 1065 | Ph-(CH₂)₃— | Me | 5-Cl | O | CH | | |
| 1066 | Ph-O(CH₂)₂— | Me | 5-Cl | O | CH | | 1.35(3H, t. J=6.7), 3.93(2H, 5, J=4.9), 4.15(2H, t, J=4.9), 4.27(2H, J=6.7), 6.80–7.51 (10H, m), 7 91 (1H, |
| 1067 | Ph-O(CH₂)₃— | Me | 5-Cl | O | CH | | |
| 1068 | Ph-O(CH₂)₄— | Me | 5-Cl | O | CH | | |
| 1069 | Cl-Ph-O(CH₂)₂— | Me | 5-Cl | O | CH | | |
| 1070 | Me-Ph-O(CH₂)₂— | Me | 5-Cl | O | CH | | |

TABLE 149

| No | R¹ | R² | R³ | X | Y | mp(°C.) | ¹H-NMR(CDCl₃) |
|---|---|---|---|---|---|---|---|
| 1071 | Me-Ph-CH₂— | Allyl | 5-Cl | O | CH | | |
| 1072 | F-Ph-CH₂— | Allyl | 5-Cl | O | CH | | |

TABLE 149-continued
| No | R¹ | R² | R³ | X | Y | mp(°C.) | ¹H-NMR(CDCl₃) |
|---|---|---|---|---|---|---|---|
| 1073 | 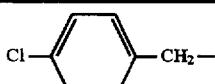 Cl—⟨⟩—CH₂— | Allyl | 5-Cl | O | CH | | |
| 1074 | 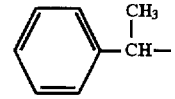 Ph-CH(CH₃)— | Allyl | 5-Cl | O | CH | | |
| 1075 | 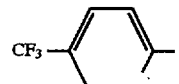 CF₃-pyridyl- | Allyl | 5-Cl | O | CH | | |
| 1076 | 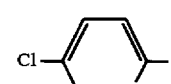 Cl-pyridyl- | Allyl | 5-Cl | O | CH | | |
| 1077 | 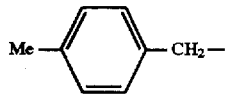 Me—⟨⟩—CH₂— | Allyl | 5-F | O | CH | | |
TABLE 150
| No | R¹ | R² | R³ | X | Y | mp(°C.) | ¹H-NMR(CDCl₃) |
|---|---|---|---|---|---|---|---|
| 1078 | 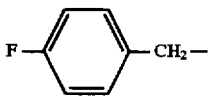 F—⟨⟩—CH₂— | Allyl | 5-F | O | CH | | |
| 1079 | 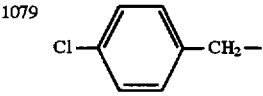 Cl—⟨⟩—CH₂— | Allyl | 5-F | O | CH | | |
| 1080 | 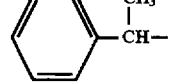 Ph-CH(CH₃)— | Allyl | 5-F | O | CH | | |
| 1081 | 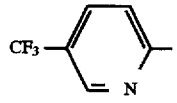 CF₃-pyridyl- | Allyl | 5-F | O | CH | | |
| 1082 | 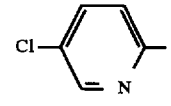 Cl-pyridyl- | Allyl | 5-F | O | CH | | |
| 1083 |  Me—⟨⟩—CH₂— | Allyl | 5-Me | O | CH | | |
| 1084 | 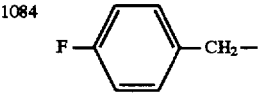 F—⟨⟩—CH₂— | Allyl | 5-Me | O | CH | | |

TABLE 150-continued

| No | R¹ | R² | R³ | X | Y | mp(°C.) | ¹H-NMR(CDCl₃) |
|---|---|---|---|---|---|---|---|
| 1085 | Cl—⟨C₆H₄⟩—CH₂— | Allyl | 5-Me | O | CH | | |

TABLE 151

| No | R¹ | R² | R³ | X | Y | mp(°C.) | ¹H-NMR(CDCl₃) |
|---|---|---|---|---|---|---|---|
| 1086 | Ph—CH(CH₃)— | Allyl | 5-Me | O | CH | | |
| 1087 | CF₃-pyridyl | Allyl | 5-Me | O | CH | | |
| 1088 | Cl-pyridyl | Allyl | 5-Me | O | CH | | |
| 1089 | Me—⟨C₆H₄⟩—CH₂— | Allyl | 5-MeO | O | CH | | |
| 1090 | F—⟨C₆H₄⟩—CH₂— | Allyl | 5-MeO | O | CH | | |
| 1091 | Cl—⟨C₆H₄⟩—CH₂— | Allyl | 5-MeO | O | CH | | |
| 1092 | Ph—CH(CH₃)— | Allyl | 5-MeO | O | CH | | |

TABLE 152

| No | R¹ | R² | R³ | X | Y | mp(°C.) | ¹H-NMR(CDCl₃) |
|---|---|---|---|---|---|---|---|
| 1093 | CF₃-pyridyl | Allyl | 5-MeO | O | CH | | |
| 1094 | Cl-pyridyl | Allyl | 5-MeO | O | CH | | |
| 1095 | Me—⟨C₆H₄⟩—CH₂— | i-Bu | 5-Cl | O | CH | | |

TABLE 152-continued
| No | R¹ | R² | R³ | X | Y | mp(°C.) | ¹H-NMR(CDCl₃) |
|---|---|---|---|---|---|---|---|
| 1096 | 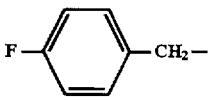 | i-Bu | 5-Cl | O | CH | | |
| 1097 | 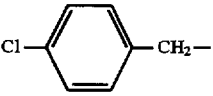 | i-Bu | 5-Cl | O | CH | | |
| 1098 | 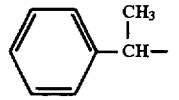 | i-Bu | 5-Cl | O | CH | | |
| 1099 | 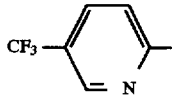 | i-Bu | 5-Cl | O | CH | | |
| 1100 | 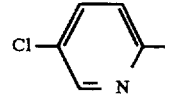 | i-Bu | 5-Cl | O | CH | | |
TABLE 153
| No | R¹ | R² | R³ | X | Y | mp(°C.) | ¹H-NMR(CDCl₃) |
|---|---|---|---|---|---|---|---|
| 1101 | 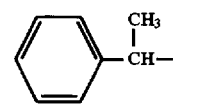 | Me | 5-F | O | CH | | 1.29(3H, d, J=6.1), 4.07(3H, s), 5.06(1H, q, J=6.1), 6.65(1H, dd, J=4.3, 9.2), 6.94–7.35(9H, m), 7.98(1H, s) |
| 1102 | 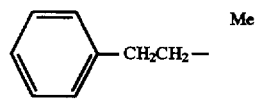 | Me | 5-Cl | O | CH | | |
| 1103 | 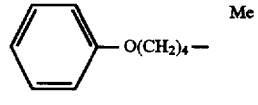 | Me | 5-Cl | O | CH | | |
| 1104 | 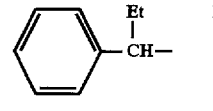 | Me | 5-MeO | O | CH | | 0.71(3H, t, J=7.3), 1.53–1.69(2H, m), 3.75(3H, s), 4.07(3H, s), 4.82(1H, t, J=6.1), 6.60(1H, d), J=9.2), 6.79(1H, dd, J=3.1, 9.2), 7.01(1H, d, J=3.1), 7.09–7.31(7H, m), 8.02(1H, s) |
| 1105 | 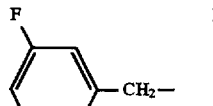 | Me | 5-Me | O | CH | | |
| 1106 |  | Me | 5-Me | O | CH | | |

TABLE 153-continued

| No | R¹ | R² | R³ | X | Y | mp(°C.) ¹H-NMR(CDCl₃) |
|---|---|---|---|---|---|---|
| 1107 | 2-OMe-C₆H₄-CH₂- | Me | 5-Me | O | CH | |

TABLE 154

| No | R¹ | R² | R³ | X | Y | mp(°C.) ¹H-NMR(CDCl₃) |
|---|---|---|---|---|---|---|
| 1108 | 2-Me-C₆H₄-CH₂- | Me | 5-Me | O | CH | |
| 1109 | 3-Me-C₆H₄-CH₂- | Me | 5-Me | O | CH | |
| 1110 | 4-Cl-C₆H₄-CH(CH₃)- | Me | H | O | CH | |
| 1111 | 4-Cl-C₆H₄-CH(CH₃)- | Me | 5-F | O | CH | |
| 1112 | 4-Cl-C₆H₄-CH(CH₃)- | Me | 5-Cl | O | CH | |
| 1113 | 4-Cl-C₆H₄-CH(CH₃)- | Me | 5-Me | O | CH | |
| 1114 | 4-Cl-C₆H₄-CH(CH₃)- | Me | 5-MeO | O | CH | |
| 1115 | 4-Cl-C₆H₄-CH(CH₃)- | Et | H | O | CH | |

TABLE 155

| No | R¹ | R² | R³ | X | Y | mp(°C.) ¹H-NMR(CDCl₃) |
|---|---|---|---|---|---|---|
| 1116 | C₆H₅-CH(Et)- | Me | 5-F | O | CH | |

TABLE 155-continued

| No | R¹ | R² | R³ | X | Y | mp(°C.) ¹H-NMR(CDCl₃) |
|---|---|---|---|---|---|---|
| 1117 | Ph-(CH₂)₄— | Me | 5-Cl | O | CH | |
| 1118 | Ph-(CH₂)₄— | Me | 5-F | O | CH | |
| 1119 | Ph-(CH₂)₄— | Me | 5-Me | O | CH | |
| 1120 | Ph-O(CH₂)₃— | Me | 5-Cl | O | CH | |
| 1121 | 4,6-diMeO-2-pyrimidinyl | Allyl | H | O | CH | |
| 1122 | 2,4-diCl-C₆H₃-CH₂— | Me | 5-Me | O | CH | |
| 1123 | 2,6-diCl-C₆H₃-CH₂— | Me | 5-Me | O | CH | |
| 1124 | 3,4-diCl-C₆H₃-CH₂— | Me | 5-Me | O | CH | |

TABLE 156

| No | R¹ | R² | R³ | X | Y | mp (°C.) | ¹H-NMR (CDCl₃) |
|---|---|---|---|---|---|---|---|
| 1125 | 2-F-C₆H₄-CH₂— | Me | 5-Me | O | CH | | |
| 1126 | Ph-CH(Et)— | Et | H | O | CH | | 0.73(3H, t, J=7.9), 1.43(3H, t, J=7.3), 1.57–1.74(2H, m), 4.33(2H, q, J=7.3), 4.92(1H, t, J=6.7), 6.69(1H, d, J=7.9), 6.94(1H, t, J=7.3), 7.09–7.31(8H, m), 7.45(1H, dd, J=1.8, 7.3), 8.07(1H, s) |

TABLE 156-continued

| No | R¹ | R² | R³ | X | Y | mp (°C.) | ¹H-NMR (CDCl₃) |
|---|---|---|---|---|---|---|---|
| 1127 | Ph-CH(Et)- | Et | 5-F | O | CH | | |
| 1128 | Ph-CH(Et)- | Et | 5-Cl | O | CH | | 0.71(3H, t, J=7.3), 1.40(3H, t, J=6.7), 1.54–1.73(2H, m), 4.33(2H, q, J=7.3), 4.87(1H, t, J=6.1), 6.61(1H, d, J=8.5), 7.05–7.32(8H, m), 7.44(1H, d, J=2.4), 8.06(1H, s) |
| 1129 | Ph-CH(Et)- | Et | 5-Me | O | CH | | 0.72(3H, t, J=7.3), 1.40(3H, t, J=7.3), 1.59–1.70(2H, m), 2.26(3H, s), 4.32(2H, q, J=7.3), 4.88(1H, t, J=6.7), 6.57(1H, d, J=8.5), 7.01–7.32(9H, m), 8.06(1H, s) |
| 1130 | Ph-CH(Et)- | Et | 5-MeO | O | CH | | 0.72(3H, t, J=7.3), 1.40(3H, t, J=6.7), 1.54–1.72(2H, m), 3.75(3H, s), 4.32(2H, q, J=7.3), 4.83(1H, t, J=6.7), 6.56(1H, d, J=9.2), 6.79(1H, dd, J=3.1, 9.2), 6.99–7.35(8H, m), 8.07(1H, s) |

The following examples illustrate the production of the fungicidal compositions of the present invention.

EXAMPLE 14

A mixture of 2 parts of the Compound No. 9 and 98 parts of talc was pulverized to obtain a powder.

EXAMPLE 15

A suspension was prepared by mixing 40 parts of Compound No. 9, 10 parts of sodium lignin sulfonate and 50 parts of water.

EXAMPLE 16

A solution was prepared by mixing 10 parts of Compound No. 9, 1 part of Tween 20 (trade mark) and 89 parts of isopropyl alcohol.

EXAMPLE 17

A wettable powder was prepared by mixing 50 parts of Compound No. 83, 6 parts of sodium alkylbenzenesulfonate, 4 parts of sodium lignin sulfonate and 40 parts of clay and pulverizing the mixture.

EXAMPLE 18

Granules were prepared by mixing 5 parts of Compound No. 83, 90 parts of a mixture of equal amounts of bentonite and talc and 5 parts of sodium alkylbenzene sulfonate, pulverizing the mixture and granulating the pulverized mixture.

EXAMPLE 19

An emulsion was prepared by mixing and dispersing 25 parts of Compound No. 83, 8 parts of polyoxyethylene alkylphenyl ether, 2 parts of sodium alkylbenzene sulfonate and 65 parts of xylene.

The following examples illustrate the production of the herbicidal and growth regulating compositions.

EXAMPLE 20

| | Parts by weight |
|---|---|
| Compound No.9 | 50 |
| Clay | 45 |
| Emal (trade mark, spreader manufactured by Kao Corp.) | 5 |

The above ingredients were mixed to give a wetable powder.

EXAMPLE 21

| | Parts by weight |
|---|---|
| Compound No.9 | 20 |
| Xylene | 65 |
| Sorpol 3005X (trade mark, spreader manufactured by Tohoh Kagaku Kogyo K.K.) | 15 |

Compound No. 9 was dissolved in xylene and Sorpol was added to give an emulsifiable concentrate.

EXAMPLE 22

| | Parts by weight |
|---|---|
| Compound No. 83 | 3 |
| Sorpol 5060 (trade mark, spreader manufactured by Tohoh Kagaku Kogyo K.K.) | 3 |
| Bentonite | 40 |
| Talc | 20 |
| Clay | 34 |

The above ingredients were mixed homogeneously and binded by adding water and subjected to extrusion to give granules.

EXAMPLE 23

| | Parts by weight |
|---|---|
| Compound No. 83 | 3 |
| Emulgen 910 (trade mark, nonionic surfactant manufactured by Kao Corp.) | 1 |
| Solvent naphtha | 5 |
| Granular bentonite | 91 |

Compound No. 83 and Emulgen were dissolved in solvent naphtha. The granular bentonite was spray-coated with this solution to obtain granules.

TEST EXAMPLES

The following pot experiments show controlling effect of the various compounds of the present invention on plant diseases by foliar treatment.

Experimental Method

In experiments for deteriments of preventive effect, a liquid sample to be tested was sprayed to test plants and opathogens were inoculated after 24 hours. In experiments for determination of curative effect, the test plants were inoculated with each pathogen, and when slight lesions were observed (24 to 48 hours after the inoculation), a liquid sample to be tested was sprayed to the test plants.

The liquid sample was prepared by dissolving the test compound in a small amount of N,N-dimethylformamide and diluting the solution with distilled water containing a spreader to a given concentration.

The precent control was calculated according to the following equation:

$$\text{Percent control (\%)} = \frac{\text{severity or number of lesions in untreated plot} - \text{severity or number of lesions in treated plot}}{\text{severity or number of lesions in untreated plot}} \times 100$$

TEST EXAMPLE 1

Controlling effect on *Pyricularia oryzae*

Two-week rice seedlings (var.: AICHIASAHI) were transplanted in plastic cups (each 9 cmϕ) and cultivated another 2 weeks. The test compound in the form of a solution or a suspension was sprayed to the foliage of the rice seedlings, to which a conidia suspension of *Pyricularia oryzae* cultured in an oatmeal medium was inoculated by spraying. The test plant was kept in a moist chamber (28° C., 100% R.H.) for 24 hours, followed by cultivation in a greenhouse for 5 days. As the control, fthalide (4,5,6,7-tetrachlorophthalide) was used. Six days after inoculation, the number of lesions of the plant was measured and the preventive effect was calculated. The results are shown in Tables 157 to 159.

In the following Tables 157 to 164, P.o. means *Pyricularia oryzae*, S.f. means *Sphaerotheca fuliginea*, B.c. means *Botrytis cinerea*, E.g. means *Erysiphe graminis* f. sp. *frifici*, pre means preventive treatment, and sup means curative treatment.

TABLE 157

| Compound No. | P.o. (%) | |
|---|---|---|
| (125 ppm) | pre | sup |
| 3 | 90 | 97 |
| 7 | 90 | 97 |
| 9 | 70 | 97 |
| 55 | 90 | 97 |
| 58 | 95 | 97 |
| 68 | 90 | 97 |
| 70 | 90 | 97 |
| 83 | 97 | 97 |
| 103 | 90 | 97 |
| 106 | 90 | 97 |
| 109 | 90 | 97 |
| 115 | 90 | 97 |
| 131 | 70 | 90 |
| 152 | | 100 |
| 155 | 97 | 97 |
| 168 | 90 | 97 |
| 170 | 90 | 97 |
| 183 | 97 | 97 |
| 184 | 93 | 90 |
| 189 | 90 | 90 |
| 196 | 97 | 70 |
| 203 | 90 | 90 |
| 233 | 90 | 90 |
| 270 | 90 | 90 |

TABLE 158

| Compound No. | P.o. (%) | |
|---|---|---|
| (125 ppm) | pre | sup |
| 283 | 90 | 90 |
| 306 | 90 | 90 |
| 315 | 90 | 90 |
| 492 | 90 | 97 |
| 494 | 90 | 97 |
| 495 | 95 | 97 |
| 552 | 95 | 97 |
| 581 | 95 | 95 |
| 583 | 95 | 95 |
| 609 | 90 | 90 |
| 624 | 95 | 90 |
| 640 | 93 | 95 |
| 655 | 90 | 90 |
| 665 | 90 | 95 |
| 669 | 95 | 95 |
| 698 | 90 | 90 |
| 703 | 95 | 90 |
| 731 | 95 | 90 |
| 803 | 90 | 90 |
| 866 | 90 | 90 |
| 869 | 90 | 90 |
| 872 | 90 | 90 |
| 876 | 97 | 97 |
| 885 | 90 | 97 |

TABLE 159

| Compound No. | P.o. (%) | |
|---|---|---|
| (125 ppm) | pre | sup |
| 888 | 90 | 90 |
| 889 | 97 | 90 |
| 937 | 90 | 90 |
| 940 | 97 | 97 |
| 946 | 90 | 90 |
| 959 | 95 | 97 |
| 970 | 90 | 90 |
| 986 | 90 | 90 |

TABLE 159-continued

| Compound No. | P.o. (%) | |
|---|---|---|
| (125 ppm) | pre | sup |
| 1016 | 93 | 97 |
| 1030 | 93 | 97 |
| 1046 | 95 | 90 |
| 1066 | 95 | 97 |
| Control | 90 | 97 |

TEST EXAMPLE 2

Controlling effect on cucumber powdery mildew (*Sphaerotheca fuliginea*)

Seeds of cucumber (var.: TSUKUBASHIROIBO) were sown in plastic cups (each 9 cm in diameter), followed by cultivation for 2 to 3 weeks. A liquid test sample in the form of a solution or suspension was sprayed on the surface of their first leaves. The pathogen was inoculated by spraying to the leaves a conidia suspension of *Sphaerotheca fuliginea* which had been cultured on the cucumber leaves. The plants were kept in a greenhouse at 20° C. for 10 days. The infected area on the leaf was observed, and the percent control was calculated. As the control, fenarimol {2,4'-dichloro-2-(pyrimidin-5-yl)benzhydryl alcohol} was used. The results are shown in Table 160.

TABLE 160

| Compound No. | S. f. (%) | |
|---|---|---|
| (125 ppm) | pre | sup |
| 1 | 100 | 100 |
| 3 | 100 | 100 |
| 7 | 100 | 100 |
| 9 | 100 | 100 |
| 15 | 100 | 100 |
| 51 | 100 | 100 |
| 52 | 100 | 100 |
| 55 | 85 | 95 |
| 65 | 85 | 90 |
| 68 | 100 | 100 |
| 70 | 100 | 100 |
| 83 | 100 | 100 |
| 107 | 100 | 100 |
| 109 | 100 | 100 |
| 131 | 100 | 100 |
| 152 | 100 | |
| 155 | 100 | 100 |
| 165 | 95 | 100 |
| 168 | 100 | 100 |
| 170 | 100 | 100 |
| 183 | 100 | 100 |
| Control | 100 | 100 |

TEST EXAMPLE 3

Contolling effect on *Botrytis cinerea*

The seeds of cucumber (var.: TSUKUBASHIROIBO) were sown in plastic cups (9 cmφ), followed by cultivation for 2 to 3 weeks. The test compound in the form of a solution or suspension was sprayed to the surface of their first leaves, and the cucumber seedlings were inoculated with mycelial disks (4 mmφ) of *Botrytis cinerea* cultured on the potato sucrose agar medium by putting the disks on the leaf surfaces. The plants were kept in a moist chamber at 20° C. for 2 days. The diameter of the lesions on the leaves was measured and the percent control was calculated. As the control, iprodione {3-(3,5-dichlorophenyl)-N-isopropyl-2,4-dioxoimidazolidine-1-carboxamide} was used. The results are shown in Table 161.

TABLE 161

| Compound No. | B.c. | |
|---|---|---|
| (125 ppm) | pre | sup |
| 1 | 100 | 70 |
| 3 | 100 | 70 |
| 7 | 100 | 50 |
| 15 | 100 | 70 |
| 68 | 90 | 50 |
| 106 | 100 | 50 |
| 109 | 70 | 30 |
| 152 | 70 | 50 |
| 501 | 100 | 30 |
| 503 | 100 | 30 |
| 526 | 70 | 30 |
| 691 | 100 | 30 |
| 694 | 70 | 30 |
| 701 | 90 | 70 |
| 707 | 100 | 30 |
| 715 | 90 | 50 |
| 726 | 100 | 30 |
| 926 | 90 | 50 |
| 935 | 100 | 30 |
| 940 | 90 | 70 |
| 965 | 70 | 30 |
| 995 | 70 | 30 |
| Control | 90 | 87 |

Text Example 4

Controlling effect on *Erysiphe graminis* f. sp. *frifici*

The seeds of wheat (var.: NORIN No. 61) were sown in plastic cups (9 cmφ), followed by cultivation for 2 to 3 weeks. The test compound in the form of a solution or suspension was sprayed to the seedlings, and the seedlings were inoculated with conidia of *Erysiphe graminis* f. sp. *frifici* cultured on the wheat leaves by putting the conidia on the test plants. The plants were kept in a greenhouse at 20° C. for 10 days. The infected area on the leaf was observed, and the percent control was calculated. As the control, fenarimol was used. The results are shown in Tables 162 to 164.

TABLE 162

| Compound No. | E.g. | |
|---|---|---|
| (125 ppm) | pre | sup |
| 62 | 90 | 90 |
| 63 | 90 | 90 |
| 209 | 97 | 97 |
| 253 | 97 | 97 |
| 483 | 97 | 97 |
| 491 | 97 | 97 |
| 492 | 100 | 97 |
| 494 | 90 | 97 |
| 496 | 90 | 97 |
| 497 | 97 | 97 |
| 531 | 90 | 97 |
| 563 | 97 | 90 |
| 568 | 97 | 90 |
| 581 | 97 | 90 |
| 592 | 90 | 70 |
| 603 | 90 | 90 |
| 606 | 97 | 90 |
| 621 | 97 | 97 |
| 622 | 97 | 90 |
| 635 | 90 | 90 |
| 649 | 97 | 90 |
| 650 | 97 | 90 |

TABLE 163

| Compound No. (125 ppm) | E.g. pre | E.g. sup |
|---|---|---|
| 692 | 90 | 90 |
| 706 | 97 | 97 |
| 707 | 90 | 90 |
| 752 | 90 | 97 |
| 765 | 90 | 90 |
| 768 | 97 | 97 |
| 770 | 97 | 97 |
| 779 | 97 | 97 |
| 781 | 97 | 90 |
| 783 | 90 | 90 |
| 831 | 97 | 90 |
| 838 | 97 | 70 |
| 855 | 97 | 90 |
| 889 | 90 | 97 |
| 902 | 90 | 97 |
| 913 | 90 | 90 |
| 914 | 90 | 97 |
| 916 | 97 | 97 |
| 929 | 97 | 90 |
| 938 | 97 | 97 |
| 943 | 90 | 97 |
| 956 | 70 | 97 |

TABLE 164

| Compound No. (125 ppm) | E.g. pre | E.g. sup |
|---|---|---|
| 967 | 90 | 97 |
| 968 | 90 | 97 |
| 973 | 90 | 97 |
| 976 | 70 | 97 |
| 997 | 97 | 97 |
| 998 | 97 | 70 |
| 1000 | 97 | 70 |
| 1003 | 97 | 97 |
| 1025 | 97 | 97 |
| 1027 | 97 | 97 |
| 1028 | 97 | 97 |
| 1033 | 97 | 97 |
| 1036 | 97 | 90 |
| 1057 | 97 | 97 |
| 1058 | 90 | 97 |
| 1063 | 90 | 97 |
| 1101 | 97 | 97 |
| 1104 | 90 | 90 |
| 1126 | 90 | 97 |
| 1128 | 70 | 97 |
| 1129 | 97 | 97 |
| Control | 97 | 97 |

The following experiment shows herbicidal and growth regulating activities of the compounds of the present invention.

TEST EXAMPLE 5

(herbicidal activity)

As the test plants, *Echinochloa oryzicola*, *Monochoria vaginalis* and *Scirpus juncoides* were used.

A square-shaped pot (7.1×7.1 cm) was charged with paddy soil. The seeds (10 seeds/pot) of the above plants were sown in the soil and submerged in water (2 cm). Immediately after that, the test compound (40 g ai/a) was diluted with water (0.7 ml/pot) and treated on the water surface of each pot.

Three weeks after the treatment, the effects of the compound (inhibition of germination and growth, deformation, leaf drying, withering, etc.) were observed. The criteria for the evaluation were grouped into the following six grades: 0 (harmless) to 5 (withering).

The second screening was carried out when the maximum activity (5) was observed in the gramineous plant, broad-leaved plant and cyperaceous plant.

The results are shown in Tables 165 and 166. In the tables, E.o. means *Echinochloa oryzicola*, M.v. means *Monochoria vaginalis*, and S.J. means *Scirpus juncoides*.

TABLE 165

| Compound No. | E.o. | M.v. | S.j. |
|---|---|---|---|
| 3 | 5 | 5 | 4 |
| 9 | 5 | 5 | 3 |
| 15 | 4 | 5 | 3 |
| 52 | 4 | 5 | 5 |
| 55 | 5 | 5 | 5 |
| 68 | 4 | 5 | 3 |
| 72 | 5 | 5 | 4 |
| 83 | 4 | 4 | 4 |
| 109 | 5 | 5 | 4 |
| 152 | 4 | 5 | 4 |
| 698 | 5 | 5 | 5 |
| 706 | 5 | 5 | 5 |
| 709 | 5 | 5 | 4 |
| 783 | 5 | 5 | 5 |
| 806 | 5 | 5 | 5 |
| 842 | 5 | 5 | 5 |
| 866 | 5 | 5 | 2 |
| 872 | 5 | 5 | 5 |
| 885 | 5 | 5 | 4 |
| 888 | 5 | 5 | 5 |
| 897 | 5 | 5 | 3 |
| 902 | 5 | 5 | 5 |
| 920 | 5 | 5 | 4 |
| 921 | 5 | 5 | 3 |
| 938 | 5 | 5 | 5 |

TABLE 166

| Compound No. | E.o. | M.v. | S.j. |
|---|---|---|---|
| 951 | 5 | 5 | 4 |
| 956 | 5 | 5 | 4 |
| 968 | 5 | 5 | 4 |
| 986 | 5 | 5 | 2 |
| 998 | 5 | 5 | 4 |
| 1006 | 5 | 5 | 3 |
| 1016 | 5 | 5 | 4 |
| 1025 | 5 | 5 | 4 |
| 1028 | 5 | 5 | 5 |
| 1030 | 5 | 5 | 5 |
| 1036 | 5 | 5 | 4 |
| 1046 | 5 | 5 | 4 |
| 1057 | 5 | 5 | 5 |
| 1058 | 5 | 5 | 5 |
| 1060 | 5 | 5 | 3 |
| 1066 | 5 | 5 | 5 |

TEST EXAMPLE 6

Growth inhibiting effect on weeds

As the test plants, *Polygonum lapathifolium* and *Amaranthus viridis* were used.

A square-shaped pot (7.1×7.1 cm) was charged with upland soil. The seeds (10 seeds/pot) of the above plants were sown on the soil and grown in a greenhouse for 7 days. Seven days after sowning, the test compound (20 g ai/a) was sprayed on the plant using a pressure-type sprayer.

Three weeks after spraying, the height of the plant was measured, and the growth inhibiting ratio was calculated according to the following equation:

Growth inhibiting ratio (%) =

$$\frac{\text{the height of the plant in untreated plot} - \text{the height of the plant in treated plot}}{\text{the height of the plant in untreated plot}} \times 100$$

The results are shown in Table 167. In the table, P.l. means *Polygonum lapathifolium* and A.v. means *Amaranthus viridis*.

TABLE 167

| Compound No. | P.l. | A.v. |
|---|---|---|
| 127 | 63 | 48 |
| 863 | 52 | 66 |
| 968 | 54 | 34 |
| 970 | 57 | 48 |
| 976 | 64 | 55 |
| 1036 | 67 | 67 |
| 1066 | 66 | 57 |

What is claimed is:

1. A compound of the formula (I):

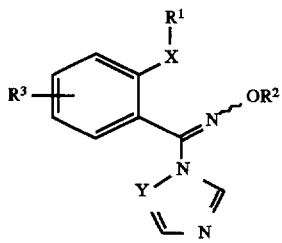

wherein $R^1$ is selected from the group consisting of alkoxycarbonylalkyl, optionally substituted acylalkyl, optionally substituted phenylalkyl, optionally substituted phenoxyalkyl, and wherein the alkyl group contains 1 to 4 carbon atoms; $R^2$ is selected from the group consisting of hydrogen, $C_{1-6}$ alkyl, $C_{2-6}$ alkenyl, $C_{2-6}$ alkynyl, halogenated $C_{1-6}$ alkyl, halogenated $C_{2-6}$ alkenyl, halogenated $C_{2-6}$ alkynyl, $C_{3-8}$ cycloalkyl, phenyl, substituted phenyl, benzyl, substituted benzyl; $R^3$ is selected from the group consisting of hydrogen, $C_{1-4}$ alkyl, $C_{1-4}$ alkoxy and halogen; X is O or S; Y is CH or N; and ~ represents any configuration of the E-isomer, Z-isomer or a mixture of E- and Z-isomers; provided that, when X is O, $R^1$ is not unsubstituted benzyl; wherein the substituted acylalkyl, substituted phenylalkyl, substituted phenoxyalkyl, substituted phenyl, substituted benzyl and have 1 to 5 substituents selected from the group consisting of $C_{1-5}$ alkyl, $C_{1-4}$ alkoxy, phenyl, penoxy, benzyloxy, $C_{1-4}$ alkylthio, $C_{1-3}$ alkylsulfonyl, cyano, nitro, halogen, halogenated $C_{1-3}$ alkyl, and halogenated $C_{1-3}$ alkoxy; or a salt thereof.

2. A compound according to claim 1, wherein $R^1$ is optionally substituted phenylalkyl or optionally substituted phenoxyalkyl; $R^2$ is $C_{1-6}$ alkyl; $R^3$ is hydrogen, $C_{1-4}$ alkyl, $C_{1-4}$ alkoxy or halogen; X is O; and Y is CH; or a salt thereof.

3. A compound according to claim 1, wherein $R^1$ is optionally substituted phenylalkyl, or optionally substituted phenoxyalkyl, or a salt thereof.

4. A compound according to claim 1, wherein $R^1$ is substituted benzyl, or a salt thereof.

5. A compound according to claim 4, wherein $R^1$ is benzyl substituted with 1 to 5 substituents selected from alkyl, alkoxy, halogen, halogenated alkyl and halogenated alkoxy, or a salt thereof.

6. A compound according to claim 1, wherein $R^1$ is optionally substituted 1-phenylalkyl, or a salt thereof.

7. A compound according to 1, wherein $R^1$ is optionally substituted 1-phenylethyl or optionally substituted 1-phenylpropyl, or a salt thereof.

8. A compound according to 1, wherein $R^1$ is optionally substituted phenethyl or optionally substituted 3-phenylpropyl, or a salt thereof.

9. A compound according to claim 1, wherein $R^1$ is 2-phenyoxyethyl, 3-phenoxypropyl or 4-phenoxybutyl each of which may optionally be substituted, or a salt thereof.

10. A compound according to claim 1, wherein $R^2$ is $C_{1-6}$ alkyl or $C_{2-6}$ alkenyl, or a salt thereof.

11. A compound according to claim 1, wherein $R^2$ is methyl, ethyl or allyl, or a salt thereof.

12. A compound according to claim 1, wherein $R^3$ is hydrogen, methyl, methoxy, fluorine or chlorine, or a salt thereof.

13. A compound according to claim 1, wherein X is O, or a salt thereof.

14. A compound according to claim 1, wherein Y is CH, or a salt thereof.

15. A compound according to claim 1, wherein $R^1$ is 4-methylphenylmethyl, $R^2$ is methyl, $R^3$ is hydrogen, X is O, and Y is CH (Compound No. 3), or a salt thereof.

16. A compound according to claim 1, wherein $R^1$ is 2-chlorophenylmethyl, $R^2$ is methyl, $R^3$ is hydrogen, X is O, and Y is CH (Compound No. 7), or a salt thereof.

17. A compound according to claim 1, wherein $R^1$ is 4-methylphenylmethyl, $R^2$ is ethyl, $R^3$ is 5-methyl, X is O, and Y is CH (Compound No. 995), or a salt thereof.

18. A compound according to claim 1, wherein $R^1$ is 1-phenylethyl, $R^2$ is methyl, $R^3$ is hydrogen, X is O, Y is CH (Compound No. 491), or a salt thereof.

19. A compound according to claim 1, wherein $R^1$ is 1-phenylethyl, $R^2$ is methyl, $R^3$ is fluoro, X is O, and Y is CH (Compound No. 1101), or a salt thereof.

20. A compound according to claim 1, wherein $R^1$ is 3-phenylpropyl, $R^2$ is methyl, $R^3$ is hydrogen, X is O, and Y is CH (Compound No. 497), or a salt thereof.

21. A compound according to claim 1, wherein $R^1$ is 2-phenoxyethyl, $R^2$ is methyl, $R^3$ is 5-chloro, X is O, and Y is CH (Compound No. 552), or a salt thereof.

22. A compound according to claim 1, wherein $R^1$ is 2-(4-chlorophenoxy)ethyl, $R^2$ is methyl, $R^3$ is hydrogen, X is O, and Y is CH (Compound No. 863), or a salt thereof.

23. A compound according to claim 1, wherein $R^1$ is 4-phenoxybutyl, $R^2$ is methyl, $R^3$ is hydrogen, X is O, and Y is CH (Compound No. 495), or a salt thereof.

24. A compound according to claim 1, wherein $R^1$ is 4-phenoxybutyl, $R^2$ is methyl, $R^3$ is hydrogen, X is O, and Y is CH (Compound No. 876), or a salt thereof.

* * * * *

UNITED STATES PATENT AND TRADEMARK OFFICE
CERTIFICATE OF CORRECTION

PATENT NO. : 5,677,465
DATED : October 14, 1997
INVENTOR(S) : Akira TAKASE et al.

It is certified that error appears in the above-identified patent and that said Letters Patent is hereby corrected as shown below:

Title page: Item [30]  , under Foreign Application Priority Data, correct the number of the Japanese application to read -- 5-170235 --.

Signed and Sealed this

Third Day of February, 1998

Attest:

BRUCE LEHMAN

Attesting Officer

Commissioner of Patents and Trademarks